(12) United States Patent
Overfield et al.

(10) Patent No.: US 9,364,619 B2
(45) Date of Patent: Jun. 14, 2016

(54) INTERACTIVE APPARATUS AND METHOD FOR REAL-TIME PROFILING OF INHALATION EFFORTS

(75) Inventors: Dennis Overfield, Fairfield, CT (US);
Carl R. Sahi, Coventry, CT (US);
Benoit Adamo, Mount Kisco, NY (US);
P. Spencer Kinsey, Sandy Hook, CT (US); Scott McLean, Waterbury, CT (US); John M. Polidoro, Coventry, CT (US); Chad C. Smutney, Watertown, CT (US)

(73) Assignee: MannKind Corporation, Valencia, CA (US)

(*) Notice: Subject to any disclaimer, the term of this patent is extended or adjusted under 35 U.S.C. 154(b) by 919 days.

(21) Appl. No.: 12/488,469

(22) Filed: Jun. 19, 2009

(65) Prior Publication Data

US 2009/0314292 A1   Dec. 24, 2009

Related U.S. Application Data

(60) Provisional application No. 61/074,487, filed on Jun. 20, 2008, provisional application No. 61/159,052, filed on Mar. 10, 2009.

(51) Int. Cl.
*A61M 15/00* (2006.01)
*A61B 5/087* (2006.01)
*A61M 16/00* (2006.01)

(52) U.S. Cl.
CPC ............ *A61M 15/0065* (2013.01); *A61B 5/087* (2013.01); *A61M 15/0021* (2014.02);

(Continued)

(58) Field of Classification Search
CPC ................. A61M 13/0001; A61M 13/0065
USPC ............ 128/202.22, 203.15, 204.22, 204.23, 128/205.23
See application file for complete search history.

(56) References Cited

U.S. PATENT DOCUMENTS 2,549,303 A   4/1951   Friden
2,754,276 A   7/1956   Joseph et al.

(Continued)

FOREIGN PATENT DOCUMENTS

CA   2551182 C   8/2010
CN   101851213   10/2010

(Continued)

OTHER PUBLICATIONS

Shimada et al, Translocation Pathway of the Intertracheally Instilled Ultrafine Particles from the Lung into the Blood Circulation in the Mouse, Journal, Toxicologic Pathology, 2006, pp. 949-957, Society of Toxicologic Pathology.

(Continued)

*Primary Examiner* — Lynne Anderson
(74) *Attorney, Agent, or Firm* — K&L Gates LLP; Louis C. Cullman; Robert W. Winn

(57) ABSTRACT

Described herein are interactive apparatus and methods for sensing and measuring real-time characteristic patterns of a subject's use of a dry powder inhalation system. The devices can be used in a wired or wireless communication mode to communicate with a display to assess the subject's usage of the inhalation system, to evaluate the performance of the inhalation system and/or to detect the characteristics profile of a dry powder formulation emitted from the inhalation system in use.

25 Claims, 17 Drawing Sheets

(52) U.S. Cl.
CPC ..... *A61M15/0025* (2014.02); *A61M 2016/003* (2013.01); *A61M 2016/0027* (2013.01); *A61M 2202/064* (2013.01); *A61M 2205/502* (2013.01); *A61M 2205/52* (2013.01); *A61M 2206/10* (2013.01)

(56) References Cited

U.S. PATENT DOCUMENTS

| | | |
|---|---|---|
| D189,076 S | 10/1960 | Altman |
| 3,337,740 A | 8/1967 | Gray et al. |
| 3,407,203 A | 10/1968 | Buijle |
| 3,518,340 A | 6/1970 | Raper |
| 3,622,053 A | 11/1971 | Ryden |
| 3,669,113 A | 6/1972 | Altounyan et al. |
| 3,823,816 A | 7/1974 | Controulis et al. |
| 3,823,843 A | 7/1974 | Stephens et al. |
| 3,856,142 A | 12/1974 | Vessalo |
| 3,906,950 A | 9/1975 | Cocozza |
| 3,921,637 A | 11/1975 | Bennie et al. |
| 3,976,773 A | 8/1976 | Curran et al. |
| 3,980,074 A | 9/1976 | Watt et al. |
| 3,998,226 A | 12/1976 | Harris |
| 4,013,075 A | 3/1977 | Cocozza |
| 4,018,619 A | 4/1977 | Webster et al. |
| 4,022,749 A | 5/1977 | Kuechler |
| 4,040,536 A | 8/1977 | Schwarz |
| 4,047,525 A | 9/1977 | Kulessa et al. |
| 4,078,128 A | 3/1978 | Hoyt et al. |
| 4,091,077 A | 5/1978 | Smith et al. |
| 4,098,273 A | 7/1978 | Glenn |
| 4,102,953 A | 7/1978 | Johnson et al. |
| 4,110,240 A | 8/1978 | Leo et al. |
| 4,148,308 A | 4/1979 | Sayer |
| 4,153,689 A | 5/1979 | Hirai |
| D252,707 S | 8/1979 | Besnard |
| 4,175,556 A | 11/1979 | Freezer |
| 4,187,129 A | 2/1980 | Bost et al. |
| 4,196,196 A | 4/1980 | Tiholiz |
| 4,206,758 A | 6/1980 | Hallworth et al. |
| 4,210,140 A | 7/1980 | James et al. |
| 4,211,769 A | 7/1980 | Okada |
| 4,268,460 A | 5/1981 | Boiarski et al. |
| 4,272,398 A | 6/1981 | Jaffe |
| 4,275,820 A | 6/1981 | LeBlond |
| 4,289,759 A | 9/1981 | Heavner et al. |
| 4,294,829 A | 10/1981 | Suzuki et al. |
| 4,300,546 A | 11/1981 | Kruber |
| 4,356,167 A | 10/1982 | Kelly |
| D269,463 S | 6/1983 | Young |
| 4,407,525 A | 10/1983 | Hoppe |
| 4,456,007 A | 6/1984 | Nakao et al. |
| 4,483,922 A | 11/1984 | Carpenter |
| D276,654 S | 12/1984 | Snellman-Wasenius et al. |
| 4,487,327 A | 12/1984 | Grayson |
| 4,524,769 A | 6/1985 | Wetterlin |
| 4,526,804 A | 7/1985 | Escallon |
| 4,534,345 A | 8/1985 | Wetterlin |
| D282,209 S | 1/1986 | Newell et al. |
| 4,581,020 A | 4/1986 | Mittleman |
| 4,592,348 A | 6/1986 | Waters, IV et al. |
| 4,613,500 A | 9/1986 | Suzuki |
| 4,615,817 A | 10/1986 | McCoy |
| 4,624,861 A | 11/1986 | Yale et al. |
| 4,637,996 A | 1/1987 | Konishi |
| D288,852 S | 3/1987 | Miyoshi |
| 4,659,696 A | 4/1987 | Hirai |
| 4,668,218 A | 5/1987 | Virtanen |
| 4,681,752 A | 7/1987 | Melillo |
| D295,321 S | 4/1988 | Hallworth |
| 4,757,066 A | 7/1988 | Shiokari et al. |
| 4,792,451 A | 12/1988 | Kim |
| 4,811,731 A | 3/1989 | Newell et al. |
| D301,273 S | 5/1989 | Leonard |
| 4,835,312 A | 5/1989 | Itoh et al. |
| 4,841,964 A | 6/1989 | Hurka et al. |
| 4,849,227 A | 7/1989 | Cho |
| 4,861,627 A | 8/1989 | Mathiowitz |
| 4,866,051 A | 9/1989 | Hunt et al. |
| 4,873,087 A | 10/1989 | Morishita et al. |
| 4,887,722 A | 12/1989 | Greenward, Sr. |
| 4,900,730 A | 2/1990 | Miyauchi |
| 4,907,583 A | 3/1990 | Wetterlin et al. |
| 4,925,673 A | 5/1990 | Steiner |
| 4,926,852 A | 5/1990 | Zoltan et al. |
| 4,927,555 A | 5/1990 | Colarusso, Jr. |
| 4,927,928 A | 5/1990 | Shroot et al. |
| 4,946,828 A | 8/1990 | Markussen |
| 4,981,295 A | 1/1991 | Belman et al. |
| 4,983,402 A | 1/1991 | Steiner et al. |
| 4,984,158 A | 1/1991 | Hillsman |
| 4,991,605 A | 2/1991 | Keritsis |
| 4,998,624 A | 3/1991 | Capes et al. |
| 5,006,343 A | 4/1991 | Benson |
| D316,902 S | 5/1991 | Hoefling |
| 5,021,376 A | 6/1991 | Nienburg et al. |
| 5,027,806 A | 7/1991 | Zoltan et al. |
| 5,042,975 A | 8/1991 | Chien |
| D321,570 S | 11/1991 | Blasdell et al. |
| 5,067,500 A | 11/1991 | Keritsis |
| 5,069,204 A | 12/1991 | Smith et al. |
| 5,074,418 A | 12/1991 | Buan et al. |
| 5,075,027 A | 12/1991 | Dixit et al. |
| 5,098,590 A | 3/1992 | Dixit et al. |
| 5,105,291 A | 4/1992 | Matsumoto et al. |
| D326,517 S | 5/1992 | Funai et al. |
| 5,110,823 A | 5/1992 | Hamaguchi et al. |
| 5,118,666 A | 6/1992 | Habener |
| 5,120,712 A | 6/1992 | Habener |
| 5,124,291 A | 6/1992 | Bremer et al. |
| 5,131,539 A | 7/1992 | Karita et al. |
| 5,145,684 A | 9/1992 | Liversidge et al. |
| 5,152,284 A | 10/1992 | Valentini et al. |
| D331,106 S | 11/1992 | Fuchs |
| 5,167,506 A | 12/1992 | Kilis et al. |
| 5,170,801 A | 12/1992 | Casper et al. |
| 5,188,837 A | 2/1993 | Domb |
| 5,201,308 A | 4/1993 | Newhouse |
| 5,203,768 A | 4/1993 | Haak et al. |
| 5,204,108 A | 4/1993 | Illum |
| D337,636 S | 7/1993 | Kocinski |
| D338,062 S | 8/1993 | Yair |
| D338,268 S | 8/1993 | Kobayashi et al. |
| 5,239,992 A | 8/1993 | Bougamont et al. |
| 5,244,653 A | 9/1993 | Berke et al. |
| 5,250,287 A | 10/1993 | Cocozza |
| D340,975 S | 11/1993 | Sladek |
| 5,260,306 A | 11/1993 | Boardman et al. |
| 5,270,305 A | 12/1993 | Palmer |
| 5,287,850 A | 2/1994 | Haber et al. |
| D344,796 S | 3/1994 | Sochon et al. |
| D344,797 S | 3/1994 | Sochon et al. |
| D345,013 S | 3/1994 | Huck et al. |
| 5,301,666 A | 4/1994 | Lerk et al. |
| 5,306,453 A | 4/1994 | Shulman |
| D347,057 S | 5/1994 | Yair |
| D348,100 S | 6/1994 | Clarke |
| 5,320,094 A | 6/1994 | Laube et al. |
| D348,928 S | 7/1994 | Ashley et al. |
| D348,929 S | 7/1994 | Paton |
| 5,327,883 A | 7/1994 | Williams et al. |
| 5,328,464 A | 7/1994 | Kriesel et al. |
| 5,331,953 A * | 7/1994 | Andersson et al. ...... 128/200.14 |
| 5,333,106 A * | 7/1994 | Lanpher et al. ............... 600/538 |
| D349,572 S | 8/1994 | Jagnandan et al. |
| D350,193 S | 8/1994 | Huck et al. |
| 5,337,740 A | 8/1994 | Armstrong et al. |
| D350,602 S | 9/1994 | Hobbs |
| D350,821 S | 9/1994 | Wright et al. |
| 5,351,683 A | 10/1994 | Chiesi et al. |
| 5,352,461 A | 10/1994 | Feldstein et al. |
| 5,354,562 A | 10/1994 | Platz |
| 5,358,734 A | 10/1994 | Lenox et al. |
| D352,107 S | 11/1994 | Meier et al. |
| 5,360,614 A | 11/1994 | Fox et al. |

(56) References Cited

U.S. PATENT DOCUMENTS

| | | |
|---|---|---|
| 5,363,842 A * | 11/1994 | Mishelevich et al. .... 128/200.14 |
| 5,364,838 A | 11/1994 | Rubsamen |
| 5,372,128 A | 12/1994 | Haber et al. |
| D355,029 S | 1/1995 | Kinneir et al. |
| 5,385,904 A | 1/1995 | Andersson et al. |
| 5,394,868 A | 3/1995 | Ambrosio et al. |
| 5,401,516 A | 3/1995 | Milstein et al. |
| D357,603 S | 4/1995 | Wolff |
| 5,404,871 A | 4/1995 | Goodman et al. |
| D358,880 S | 5/1995 | Mulhauser et al. |
| 5,413,804 A | 5/1995 | Rhodes |
| 5,415,162 A | 5/1995 | Casper et al. |
| D359,153 S | 6/1995 | Viggiano |
| D359,555 S | 6/1995 | Funai et al. |
| 5,424,286 A | 6/1995 | Eng |
| 5,437,271 A | 8/1995 | Hodson et al. |
| 5,443,841 A | 8/1995 | Milstein et al. |
| D362,500 S | 9/1995 | Cook et al. |
| 5,447,150 A | 9/1995 | Bacon |
| 5,447,151 A | 9/1995 | Bruna et al. |
| 5,447,728 A | 9/1995 | Milstein et al. |
| 5,451,410 A | 9/1995 | Milstein et al. |
| D363,775 S | 10/1995 | Hobbs |
| 5,454,871 A | 10/1995 | Liaw et al. |
| 5,455,335 A | 10/1995 | Kahne et al. |
| 5,458,135 A | 10/1995 | Patton et al. |
| 5,466,971 A | 11/1995 | Higuchi |
| 5,469,750 A | 11/1995 | Lloyd et al. |
| 5,476,093 A | 12/1995 | Lankinen |
| 5,477,285 A | 12/1995 | Riddle et al. |
| D365,876 S | 1/1996 | Chawla |
| 5,482,032 A | 1/1996 | Smith et al. |
| 5,482,927 A | 1/1996 | Maniar |
| 5,483,954 A | 1/1996 | Mecikalski |
| 5,484,606 A | 1/1996 | Dhaber et al. |
| 5,487,378 A | 1/1996 | Robertson et al. |
| 5,492,112 A | 2/1996 | Mecikalski et al. |
| D368,364 S | 4/1996 | Reitano et al. |
| 5,503,144 A | 4/1996 | Bacon |
| 5,503,852 A | 4/1996 | Steiner et al. |
| 5,505,194 A | 4/1996 | Adjei et al. |
| 5,506,203 A | 4/1996 | Backstrom et al. |
| D370,255 S | 5/1996 | Yamamoto et al. |
| 5,514,646 A | 5/1996 | Chance et al. |
| 5,518,998 A | 5/1996 | Backstrom et al. |
| 5,524,613 A | 6/1996 | Haber et al. |
| 5,532,461 A | 7/1996 | Crummenauer et al. |
| 5,533,502 A | 7/1996 | Piper |
| 5,533,505 A | 7/1996 | Kallstrand et al. |
| 5,542,411 A | 8/1996 | Rex |
| 5,542,539 A | 8/1996 | Early |
| 5,545,618 A | 8/1996 | Buckley et al. |
| 5,547,929 A | 8/1996 | Anderson, Jr. et al. |
| 5,562,909 A | 10/1996 | Allcock et al. |
| 5,562,918 A | 10/1996 | Stimpson |
| 5,568,884 A | 10/1996 | Bruna |
| 5,570,810 A | 11/1996 | Lambelet, Jr. et al. |
| 5,571,795 A | 11/1996 | Kahne et al. |
| 5,574,008 A | 11/1996 | Johnson et al. |
| 5,577,497 A | 11/1996 | Mecikalski et al. |
| 5,578,323 A | 11/1996 | Milstein et al. |
| 5,584,417 A | 12/1996 | Graf et al. |
| D377,215 S | 1/1997 | Rand |
| D377,686 S | 1/1997 | Waldeck et al. |
| 5,595,175 A | 1/1997 | Malcher et al. |
| 5,596,701 A | 1/1997 | Augusteijn et al. |
| D377,861 S | 2/1997 | Jacober |
| 5,598,835 A | 2/1997 | von Schrader |
| 5,601,846 A | 2/1997 | Milstein et al. |
| 5,610,271 A | 3/1997 | Dooley et al. |
| 5,614,492 A | 3/1997 | Habener |
| 5,617,844 A | 4/1997 | King |
| 5,619,984 A | 4/1997 | Hodson et al. |
| 5,622,164 A | 4/1997 | Kilis et al. |
| 5,622,166 A | 4/1997 | Eisele et al. |
| 5,623,724 A | 4/1997 | Gurkovich et al. |
| 5,623,920 A | 4/1997 | Bryant |
| D379,506 S | 5/1997 | Maher |
| 5,629,020 A | 5/1997 | Leone-Bay |
| 5,631,224 A | 5/1997 | Efendic et al. |
| 5,632,971 A | 5/1997 | Yang |
| 5,634,900 A | 6/1997 | Makino et al. |
| 5,641,861 A | 6/1997 | Dooley et al. |
| D381,416 S | 7/1997 | Hansson et al. |
| 5,642,727 A | 7/1997 | Datta et al. |
| 5,642,728 A | 7/1997 | Andersson et al. |
| 5,643,957 A | 7/1997 | Leone-Bay et al. |
| 5,645,051 A | 7/1997 | Schultz et al. |
| 5,651,359 A | 7/1997 | Bougamont et al. |
| 5,653,961 A | 8/1997 | McNally et al. |
| 5,655,516 A | 8/1997 | Goodman et al. |
| 5,655,523 A | 8/1997 | Hodson et al. |
| 5,657,748 A | 8/1997 | Braithwaite |
| 5,658,878 A | 8/1997 | Backstrom et al. |
| 5,660,169 A | 8/1997 | Kallstrand et al. |
| 5,672,581 A | 9/1997 | Rubsamen et al. |
| 5,673,686 A | 10/1997 | Villax et al. |
| 5,679,377 A | 10/1997 | Bernstein et al. |
| 5,687,710 A | 11/1997 | Ambrosio et al. |
| 5,690,910 A | 11/1997 | Ahmed et al. |
| 5,693,338 A | 12/1997 | Milstein |
| 5,699,789 A | 12/1997 | Hendricks |
| D389,238 S | 1/1998 | Kirk, III et al. |
| D389,570 S | 1/1998 | Savolainen |
| 5,705,483 A | 1/1998 | Galloway et al. |
| D390,651 S | 2/1998 | Smith et al. |
| D390,653 S | 2/1998 | Blasdell et al. |
| 5,714,007 A | 2/1998 | Pletcher et al. |
| 5,714,167 A | 2/1998 | Milstein et al. |
| 5,727,546 A | 3/1998 | Clarke et al. |
| 5,740,793 A | 4/1998 | Hodson et al. |
| 5,740,794 A | 4/1998 | Smith et al. |
| 5,746,197 A | 5/1998 | Williams |
| 5,746,227 A | 5/1998 | Rose et al. |
| 5,747,445 A | 5/1998 | Backstrom et al. |
| 5,752,505 A | 5/1998 | Ohki et al. |
| 5,755,218 A | 5/1998 | Johansson et al. |
| D395,147 S | 6/1998 | Vidgren et al. |
| D395,499 S | 6/1998 | Eisele et al. |
| 5,758,638 A | 6/1998 | Kreamer |
| 5,763,396 A | 6/1998 | Weiner et al. |
| 5,766,620 A | 6/1998 | Heiber et al. |
| 5,766,633 A | 6/1998 | Milstein et al. |
| 5,769,073 A | 6/1998 | Eason et al. |
| 5,772,085 A | 6/1998 | Bryant et al. |
| RE35,862 E | 7/1998 | Steiner et al. |
| 5,775,320 A | 7/1998 | Patton et al. |
| 5,785,049 A | 7/1998 | Smith et al. |
| 5,785,989 A | 7/1998 | Stanley et al. |
| D397,435 S | 8/1998 | Naumann |
| 5,792,451 A | 8/1998 | Sarubbi et al. |
| 5,794,613 A | 8/1998 | Piskorski |
| 5,797,391 A | 8/1998 | Cook et al. |
| D398,992 S | 9/1998 | Feret |
| 5,799,821 A | 9/1998 | Lambelet, Jr. et al. |
| 5,807,315 A | 9/1998 | Va Antwerp et al. |
| 5,809,997 A * | 9/1998 | Wolf ........................ 128/200.23 |
| 5,811,127 A | 9/1998 | Milstein et al. |
| 5,813,397 A | 9/1998 | Goodman et al. |
| 5,824,345 A | 10/1998 | Milstein et al. |
| 5,839,429 A | 11/1998 | Marnfeldt et al. |
| 5,840,279 A | 11/1998 | Narodylo et al. |
| 5,840,340 A | 11/1998 | Milstein et al. |
| 5,846,447 A | 12/1998 | Beatty |
| 5,848,589 A | 12/1998 | Welnetz |
| 5,849,322 A | 12/1998 | Ebert et al. |
| 5,857,457 A | 1/1999 | Hyppola |
| 5,858,099 A | 1/1999 | Sun et al. |
| 5,865,012 A | 2/1999 | Hansson et al. |
| 5,874,064 A | 2/1999 | Edwards et al. |
| 5,875,776 A | 3/1999 | Vagheti |
| 5,877,174 A | 3/1999 | Ono et al. |
| 5,881,719 A | 3/1999 | Gottenauer et al. |
| 5,881,721 A | 3/1999 | Bunce et al. |

(56) References Cited

U.S. PATENT DOCUMENTS

| | | |
|---|---|---|
| 5,884,620 A | 3/1999 | Gonda et al. |
| 5,888,477 A | 3/1999 | Gonda et al. |
| 5,896,855 A | 4/1999 | Hobbs et al. |
| 5,901,703 A | 5/1999 | Ohki et al. |
| 5,904,139 A | 5/1999 | Hauser |
| D410,541 S | 6/1999 | Moulin |
| D411,005 S | 6/1999 | Coe |
| 5,908,639 A | 6/1999 | Simpkin et al. |
| 5,912,011 A | 6/1999 | Makino et al. |
| 5,918,594 A | 7/1999 | Asking et al. |
| 5,919,897 A | 7/1999 | Dooley et al. |
| 5,921,237 A | 7/1999 | Eisele et al. |
| 5,924,419 A | 7/1999 | Kotliar |
| 5,929,027 A | 7/1999 | Takama et al. |
| D412,572 S | 8/1999 | Gray |
| D412,744 S | 8/1999 | Braithwaite |
| D412,978 S | 8/1999 | Cameron |
| D412,979 S | 8/1999 | Weinstein et al. |
| 5,934,273 A | 8/1999 | Andersson et al. |
| 5,942,242 A | 8/1999 | Mizushima et al. |
| 5,948,749 A | 9/1999 | Igarashi et al. |
| 5,952,008 A | 9/1999 | Backstrom et al. |
| 5,954,047 A | 9/1999 | Armer et al. |
| 5,965,701 A | 10/1999 | Junien et al. |
| 5,971,951 A | 10/1999 | Ruskewicz |
| D416,085 S | 11/1999 | Forssell et al. |
| D416,621 S | 11/1999 | Forssell et al. |
| D416,998 S | 11/1999 | Hodson et al. |
| D417,271 S | 11/1999 | Denyer et al. |
| 5,975,347 A | 11/1999 | Lambelet, Jr. et al. |
| 5,976,569 A | 11/1999 | Milstein |
| 5,976,574 A | 11/1999 | Gordon |
| 5,977,071 A | 11/1999 | Galloway et al. |
| 5,980,865 A | 11/1999 | Ahmed |
| 5,981,488 A | 11/1999 | Hoffman |
| 5,983,893 A | 11/1999 | Wetterlin |
| 5,985,248 A | 11/1999 | Gordon et al. |
| 5,985,309 A | 11/1999 | Edwards et al. |
| 5,990,077 A | 11/1999 | Drucker |
| D417,732 S | 12/1999 | Dagsland et al. |
| D417,912 S | 12/1999 | Dagsland et al. |
| 5,996,577 A | 12/1999 | Ohki et al. |
| 5,997,848 A | 12/1999 | Patton et al. |
| 6,001,336 A | 12/1999 | Gordon |
| 6,006,747 A | 12/1999 | Eisele et al. |
| 6,006,753 A | 12/1999 | Efendic |
| D418,600 S | 1/2000 | Haerle |
| D420,736 S | 2/2000 | Moulin |
| 6,026,809 A | 2/2000 | Abrams et al. |
| 6,029,663 A | 2/2000 | Eisele et al. |
| D421,800 S | 3/2000 | Doat |
| 6,039,208 A | 3/2000 | Lambelet et al. |
| 6,043,214 A | 3/2000 | Jensen et al. |
| 6,045,828 A | 4/2000 | Bystrom et al. |
| 6,051,256 A | 4/2000 | Platz et al. |
| 6,051,551 A | 4/2000 | Hughes et al. |
| 6,055,980 A | 5/2000 | Mecikalski et al. |
| 6,056,169 A | 5/2000 | Bruna et al. |
| 6,060,069 A | 5/2000 | Hill et al. |
| 6,063,910 A | 5/2000 | Debenedetti et al. |
| 6,071,497 A | 6/2000 | Steiner et al. |
| 6,073,629 A | 6/2000 | Hardy et al. |
| 6,076,521 A * | 6/2000 | Lindahl et al. ............ 128/203.15 |
| 6,077,543 A | 6/2000 | Gordon et al. |
| 6,080,762 A | 6/2000 | Allen et al. |
| D428,486 S | 7/2000 | Schuckmann |
| 6,085,745 A | 7/2000 | Levander et al. |
| 6,087,334 A | 7/2000 | Beeley et al. |
| 6,087,351 A | 7/2000 | Nye |
| 6,089,228 A | 7/2000 | Smith et al. |
| 6,095,136 A | 8/2000 | Virtanen |
| 6,098,618 A | 8/2000 | Jennings et al. |
| 6,099,517 A | 8/2000 | Daughtery |
| 6,102,035 A | 8/2000 | Asking et al. |
| 6,105,571 A | 8/2000 | Coffee |
| 6,105,574 A | 8/2000 | Jahnsson |
| 6,109,261 A | 8/2000 | Clarke et al. |
| 6,109,481 A | 8/2000 | Alexander et al. |
| 6,116,237 A | 9/2000 | Schultz |
| 6,116,238 A | 9/2000 | Jackson et al. |
| 6,116,239 A | 9/2000 | Volgyesi |
| 6,119,684 A | 9/2000 | Nohl et al. |
| 6,119,688 A | 9/2000 | Whaley et al. |
| 6,131,567 A | 10/2000 | Gonda et al. |
| 6,132,766 A | 10/2000 | Sankaram et al. |
| 6,133,235 A | 10/2000 | Galloway et al. |
| 6,142,145 A | 11/2000 | Dagsland |
| 6,152,130 A * | 11/2000 | Abrams et al. ............ 128/204.21 |
| 6,153,613 A | 11/2000 | Ono et al. |
| 6,155,423 A | 12/2000 | Katzne et al. |
| 6,156,114 A | 12/2000 | Bell et al. |
| 6,158,431 A | 12/2000 | Poole |
| 6,159,360 A | 12/2000 | Gerteis et al. |
| RE37,053 E | 2/2001 | Hanes et al. |
| 6,182,655 B1 | 2/2001 | Keller et al. |
| 6,187,291 B1 | 2/2001 | Weinstein et al. |
| 6,191,102 B1 | 2/2001 | DiMarchi et al. |
| 6,192,876 B1 | 2/2001 | Denyer et al. |
| 6,193,844 B1 | 2/2001 | McLaughlin et al. |
| 6,193,957 B1 | 2/2001 | Ahmed |
| D438,612 S | 3/2001 | Suh |
| D439,325 S | 3/2001 | Frost |
| D439,656 S | 3/2001 | Andersson et al. |
| 6,198,847 B1 | 3/2001 | Washizawa |
| D441,446 S | 5/2001 | Dagsland et al. |
| D441,859 S | 5/2001 | Pera |
| D442,685 S | 5/2001 | Sladek |
| 6,235,725 B1 | 5/2001 | Ahmed |
| D444,226 S | 6/2001 | Geert-Jensen et al. |
| 6,250,300 B1 | 6/2001 | Andersson et al. |
| 6,254,854 B1 | 7/2001 | Edwards et al. |
| 6,257,232 B1 | 7/2001 | Andersson et al. |
| 6,258,816 B1 | 7/2001 | Singh et al. |
| 6,263,871 B1 | 7/2001 | Brown et al. |
| 6,269,952 B1 | 8/2001 | Watt et al. |
| 6,273,084 B1 | 8/2001 | Frid |
| 6,273,085 B1 | 8/2001 | Eisele et al. |
| 6,273,086 B1 | 8/2001 | Ohki et al. |
| 6,277,819 B1 | 8/2001 | Efendic |
| 6,279,511 B1 | 8/2001 | Loughnane |
| D448,076 S | 9/2001 | von Schuckmann |
| 6,286,506 B1 | 9/2001 | MacAndrew et al. |
| 6,286,507 B1 | 9/2001 | Jahnsson |
| 6,294,204 B1 | 9/2001 | Rossling et al. |
| D449,684 S | 10/2001 | Christrup et al. |
| 6,298,846 B1 | 10/2001 | Ohki et al. |
| 6,298,847 B1 | 10/2001 | Datta et al. |
| D450,117 S | 11/2001 | Braithwaite et al. |
| D451,597 S | 12/2001 | Suh |
| 6,328,034 B1 | 12/2001 | Eisele et al. |
| 6,331,318 B1 | 12/2001 | Milstein |
| D452,910 S | 1/2002 | Braithwaite et al. |
| 6,335,316 B1 | 1/2002 | Hughes et al. |
| D453,264 S | 2/2002 | Acevedo, Jr. |
| 6,347,629 B1 | 2/2002 | Braithwaite |
| 6,348,447 B1 | 2/2002 | Hellstrom et al. |
| 6,357,442 B1 | 3/2002 | Casper et al. |
| 6,358,058 B1 * | 3/2002 | Strupat et al. .................. 434/262 |
| 6,358,924 B1 | 3/2002 | Hoffman |
| 6,360,743 B1 | 3/2002 | Andersson et al. |
| 6,360,929 B1 | 3/2002 | McCarthy |
| D455,208 S | 4/2002 | Bacon et al. |
| 6,363,932 B1 | 4/2002 | Forchione et al. |
| 6,365,190 B1 | 4/2002 | Gordon et al. |
| 6,372,258 B1 | 4/2002 | Platz et al. |
| 6,375,975 B1 | 4/2002 | Modi |
| 6,380,357 B2 | 4/2002 | Harmeling et al. |
| 6,386,195 B1 | 5/2002 | Coffee |
| 6,388,053 B1 | 5/2002 | Galloway et al. |
| 6,394,085 B1 | 5/2002 | Hardy et al. |
| 6,395,300 B1 | 5/2002 | Straub et al. |
| 6,395,744 B1 | 5/2002 | Adams et al. |
| 6,395,774 B1 | 5/2002 | Milstein |
| 6,410,513 B1 | 6/2002 | Galloway et al. |

(56) References Cited

U.S. PATENT DOCUMENTS

| | | |
|---|---|---|
| D460,173 S | 7/2002 | Harrison |
| 6,415,784 B1 | 7/2002 | Christrup et al. |
| 6,418,926 B1 | 7/2002 | Chawla |
| 6,423,344 B1 | 7/2002 | Platz et al. |
| D461,239 S | 8/2002 | Cassidy |
| 6,427,688 B1 | 8/2002 | Ligotke et al. |
| 6,428,771 B1 | 8/2002 | Steiner et al. |
| 6,428,805 B1 | 8/2002 | Dohi et al. |
| 6,432,383 B1 | 8/2002 | Modi |
| 6,436,443 B2 | 8/2002 | Edwards et al. |
| 6,439,227 B1 | 8/2002 | Myrman et al. |
| 6,440,463 B1 | 8/2002 | Feldstein et al. |
| 6,441,172 B1 | 8/2002 | Nefzi et al. |
| D463,544 S | 9/2002 | Engelbreth et al. |
| 6,443,143 B1 | 9/2002 | Ishida et al. |
| 6,444,226 B1 | 9/2002 | Steiner et al. |
| 6,446,626 B1 | 9/2002 | Virtanen |
| 6,446,627 B1 | 9/2002 | Bowman et al. |
| 6,447,750 B1 | 9/2002 | Cutie et al. |
| 6,447,751 B1 | 9/2002 | Weinstein et al. |
| 6,447,753 B2 | 9/2002 | Edwards et al. |
| 6,451,337 B1 | 9/2002 | Smith et al. |
| 6,457,470 B1 | 10/2002 | Coffee |
| 6,468,507 B1 | 10/2002 | Cutie et al. |
| 6,468,686 B1 | 10/2002 | Mercuri et al. |
| 6,470,884 B2 | 10/2002 | Horlin |
| 6,479,049 B1 | 11/2002 | Platz et al. |
| 6,484,715 B1 | 11/2002 | Ritsche et al. |
| 6,484,717 B1 | 11/2002 | Dagsland et al. |
| D469,527 S | 1/2003 | Keller et al. |
| 6,503,480 B1 | 1/2003 | Edwards et al. |
| 6,509,006 B1 | 1/2003 | Platz et al. |
| 6,509,313 B1 | 1/2003 | Smith |
| D469,866 S | 2/2003 | Albulet et al. |
| 6,514,482 B1 | 2/2003 | Bartus et al. |
| 6,518,239 B1 | 2/2003 | Kuo et al. |
| D471,273 S | 3/2003 | Albulet et al. |
| 6,528,096 B1 | 3/2003 | Musa et al. |
| 6,532,437 B1 | 3/2003 | Clardy et al. |
| 6,536,427 B2 | 3/2003 | Davies et al. |
| D473,298 S | 4/2003 | Bowman et al. |
| D473,640 S | 4/2003 | Cuffaro et al. |
| 6,540,672 B1 | 4/2003 | Simonsen et al. |
| 6,540,982 B1 | 4/2003 | Adjei et al. |
| 6,540,983 B1 | 4/2003 | Adjei et al. |
| 6,543,448 B1 | 4/2003 | Smith et al. |
| 6,546,929 B2 | 4/2003 | Burr et al. |
| 6,555,521 B2 | 4/2003 | Hermeling et al. |
| D474,536 S | 5/2003 | Albulet et al. |
| D475,133 S | 5/2003 | McLuckie |
| 6,557,549 B2 | 5/2003 | Schmidt et al. |
| 6,561,186 B2 | 5/2003 | Casper et al. |
| 6,567,686 B2 | 5/2003 | Sexton |
| 6,568,390 B2 | 5/2003 | Nichols et al. |
| 6,569,406 B2 | 5/2003 | Stevenson et al. |
| 6,571,793 B1 | 6/2003 | Nilsson |
| 6,572,893 B2 | 6/2003 | Gordon et al. |
| 6,575,160 B1 | 6/2003 | Volgyesi |
| 6,575,162 B1 | 6/2003 | Rand |
| 6,578,571 B1 | 6/2003 | Watt |
| 6,582,728 B1 | 6/2003 | Platz et al. |
| 6,583,111 B1 | 6/2003 | DiMarchi |
| D477,665 S | 7/2003 | Myrman et al. |
| 6,589,560 B2 | 7/2003 | Foster et al. |
| 6,591,832 B1 | 7/2003 | DeJonge |
| 6,592,904 B2 | 7/2003 | Platz et al. |
| 6,595,205 B2 | 7/2003 | Andersson et al. |
| 6,595,208 B2 | 7/2003 | Coffee et al. |
| D478,983 S | 8/2003 | Whitehall et al. |
| 6,606,992 B1 | 8/2003 | Schuler et al. |
| D479,745 S | 9/2003 | Albulet et al. |
| 6,613,308 B2 | 9/2003 | Bartus et al. |
| 6,615,987 B1 | 9/2003 | Greenhill et al. |
| 6,620,910 B1 | 9/2003 | Calas et al. |
| 6,626,173 B2 | 9/2003 | Genova et al. |
| D480,806 S | 10/2003 | Engelbreth et al. |
| 6,630,169 B1 | 10/2003 | Bot et al. |
| 6,632,258 B1 | 10/2003 | Wheelock et al. |
| 6,632,456 B1 | 10/2003 | Backstrom et al. |
| 6,635,283 B2 | 10/2003 | Edwards et al. |
| 6,637,431 B2 | 10/2003 | Ekelius et al. |
| 6,640,050 B2 | 10/2003 | Nichols et al. |
| 6,644,309 B2 | 11/2003 | Casper et al. |
| 6,645,468 B2 | 11/2003 | Cutie et al. |
| 6,645,504 B1 | 11/2003 | Weiner et al. |
| 6,652,838 B2 | 11/2003 | Weinstein et al. |
| 6,652,885 B2 | 11/2003 | Steiner et al. |
| D483,860 S | 12/2003 | Knoch |
| 6,655,379 B2 | 12/2003 | Clark et al. |
| 6,655,380 B1 | 12/2003 | Andersson et al. |
| 6,655,381 B2 | 12/2003 | Keane et al. |
| 6,660,716 B1 | 12/2003 | Yakubu-Madus et al. |
| 6,663,898 B2 | 12/2003 | Milstein |
| 6,668,826 B1 | 12/2003 | Myrman |
| 6,672,304 B1 | 1/2004 | Casper et al. |
| 6,676,931 B2 | 1/2004 | Dugger, III |
| 6,679,255 B2 | 1/2004 | Pera |
| 6,681,767 B1 | 1/2004 | Patton et al. |
| 6,681,768 B2 | 1/2004 | Haaije de Boer et al. |
| 6,685,967 B1 | 2/2004 | Patton |
| 6,698,421 B2 | 3/2004 | Attolini |
| 6,701,917 B2 | 3/2004 | O'Leary |
| 6,703,361 B2 | 3/2004 | Weiner et al. |
| 6,703,365 B2 | 3/2004 | Galloway et al. |
| 6,703,381 B1 | 3/2004 | Ekwuribe et al. |
| 6,705,313 B2 | 3/2004 | Niccolai |
| 6,715,486 B2 | 4/2004 | Gieschen et al. |
| 6,715,487 B2 | 4/2004 | Nichols et al. |
| 6,718,972 B2 | 4/2004 | O'Leary |
| 6,720,407 B1 | 4/2004 | Hughes et al. |
| 6,722,363 B1 | 4/2004 | von Schuckmann |
| D489,448 S | 5/2004 | Shayan |
| 6,729,324 B2 | 5/2004 | Casper et al. |
| 6,737,045 B2 | 5/2004 | Patton |
| 6,745,761 B2 | 6/2004 | Christrup et al. |
| 6,747,006 B2 | 6/2004 | Efendic |
| 6,748,946 B1 | 6/2004 | Rand et al. |
| 6,748,947 B2 | 6/2004 | Keane et al. |
| 6,752,145 B1 * | 6/2004 | Bonney et al. ............ 128/200.23 |
| 6,755,190 B2 | 6/2004 | Rasmussen |
| D492,769 S | 7/2004 | Hatanaka |
| D493,220 S | 7/2004 | Burge et al. |
| D493,519 S | 7/2004 | Jonsson et al. |
| 6,774,112 B2 | 8/2004 | Gougoutas |
| 6,787,152 B2 | 9/2004 | Kirby et al. |
| 6,790,496 B1 | 9/2004 | Levander et al. |
| 6,792,945 B2 | 9/2004 | Davies et al. |
| 6,793,238 B2 | 9/2004 | Schneider et al. |
| 6,799,572 B2 | 10/2004 | Nichols et al. |
| 6,800,643 B2 | 10/2004 | Cuenoud et al. |
| 6,803,044 B1 | 10/2004 | Catania et al. |
| 6,821,949 B2 | 11/2004 | Bridon et al. |
| 6,823,863 B2 | 11/2004 | Huxham et al. |
| D499,802 S | 12/2004 | Pinon et al. |
| 6,830,046 B2 | 12/2004 | Blakley et al. |
| 6,838,075 B2 | 1/2005 | Stevenson et al. |
| 6,838,076 B2 | 1/2005 | Patton et al. |
| 6,847,595 B2 | 1/2005 | Tanaka |
| 6,848,443 B2 | 2/2005 | Schmidt et al. |
| 6,849,708 B1 | 2/2005 | Habener |
| 6,852,690 B1 | 2/2005 | Nauck et al. |
| 6,858,199 B1 | 2/2005 | Edwards et al. |
| 6,860,262 B2 | 3/2005 | Christrup et al. |
| 6,866,037 B1 | 3/2005 | Aslin et al. |
| 6,871,646 B2 | 3/2005 | Keane et al. |
| 6,871,647 B2 | 3/2005 | Allan et al. |
| 6,880,554 B1 | 4/2005 | Coffee |
| 6,881,423 B2 | 4/2005 | Dohi et al. |
| 6,884,435 B1 | 4/2005 | O'Hagan et al. |
| 6,887,459 B1 | 5/2005 | Haeberlin |
| 6,887,849 B2 | 5/2005 | Bridon et al. |
| 6,889,687 B1 | 5/2005 | Olsson |
| 6,892,728 B2 | 5/2005 | Helgesson et al. |
| 6,896,906 B2 | 5/2005 | Hastedt et al. |

(56) References Cited

U.S. PATENT DOCUMENTS

| | | |
|---|---|---|
| 6,904,907 B2 | 6/2005 | Speldrich et al. |
| 6,906,030 B2 | 6/2005 | Milstein |
| 6,916,354 B2 | 7/2005 | Elliott |
| 6,918,991 B2 | 7/2005 | Chickering, III et al. |
| 6,921,458 B2 | 7/2005 | Chickering, III et al. |
| 6,921,528 B2 | 7/2005 | Edwards et al. |
| 6,923,175 B2 | 8/2005 | Poole et al. |
| D509,296 S | 9/2005 | Minshull et al. |
| D509,898 S | 9/2005 | Bunce et al. |
| 6,948,496 B2 | 9/2005 | Eason et al. |
| 6,949,258 B2 | 9/2005 | Zhang |
| 6,951,215 B1 | 10/2005 | Hoffman |
| 6,953,812 B2 | 10/2005 | Joregenson et al. |
| D511,208 S | 11/2005 | Pardonge et al. |
| 6,962,006 B2 | 11/2005 | Chickering, III et al. |
| D512,777 S | 12/2005 | Beisner et al. |
| 6,979,437 B2 | 12/2005 | Bartus et al. |
| D514,222 S | 1/2006 | Anderson et al. |
| 6,981,499 B2 | 1/2006 | Anderson et al. |
| 6,989,155 B1 | 1/2006 | Ganderton et al. |
| 6,991,779 B2 | 1/2006 | Steiner et al. |
| D515,696 S | 2/2006 | Lucking et al. |
| D516,211 S | 2/2006 | Minshull et al. |
| 6,998,387 B1 | 2/2006 | Goke et al. |
| D518,170 S | 3/2006 | Clarke et al. |
| D518,171 S | 3/2006 | Anderson et al. |
| 7,022,674 B2 | 4/2006 | DeFelippis et al. |
| 7,025,056 B2 | 4/2006 | Eason et al. |
| 7,028,686 B2 | 4/2006 | Gonda et al. |
| 7,030,084 B2 | 4/2006 | Ekwuribe et al. |
| 7,032,593 B2 | 4/2006 | Johnston et al. |
| 7,035,294 B2 | 4/2006 | Dove et al. |
| 7,047,967 B2 | 5/2006 | Knudsen |
| 7,048,908 B2 | 5/2006 | Basu et al. |
| 7,060,274 B2 | 6/2006 | Blumberg et al. |
| 7,067,129 B2 | 6/2006 | Blumberg et al. |
| 7,077,130 B2 | 7/2006 | Nichols et al. |
| 7,080,642 B2 | 7/2006 | Hodson et al. |
| 7,084,243 B2 | 8/2006 | Glaesner et al. |
| 7,093,594 B2 | 8/2006 | Harrison et al. |
| 7,093,595 B2 | 8/2006 | Nesbitt |
| D527,817 S | 9/2006 | Ziegler et al. |
| 7,101,843 B2 | 9/2006 | Glaesner et al. |
| 7,101,866 B2 | 9/2006 | Biggadike et al. |
| 7,107,988 B2 | 9/2006 | Pinon et al. |
| D529,604 S | 10/2006 | Young et al. |
| 7,128,067 B2 | 10/2006 | Byron et al. |
| 7,131,441 B1 | 11/2006 | Keller et al. |
| 7,132,115 B2 | 11/2006 | Musa et al. |
| 7,140,365 B2 | 11/2006 | Poole et al. |
| D533,268 S | 12/2006 | Olfati |
| 7,143,764 B1 | 12/2006 | Dagsland et al. |
| 7,143,765 B2 | 12/2006 | Asking et al. |
| 7,144,863 B2 | 12/2006 | DeFelippis et al. |
| 7,146,978 B2 | 12/2006 | Edwards et al. |
| 7,151,456 B2 * | 12/2006 | Godfrey ............... 340/573.1 |
| 7,163,014 B2 | 1/2007 | Nichols et al. |
| D537,522 S | 2/2007 | Cox et al. |
| 7,171,965 B2 | 2/2007 | Young et al. |
| 7,172,768 B2 | 2/2007 | Hastedt et al. |
| 7,179,788 B2 | 2/2007 | DeFelippis et al. |
| D537,936 S | 3/2007 | Cox et al. |
| D538,423 S | 3/2007 | Berube et al. |
| 7,185,650 B2 | 3/2007 | Huber et al. |
| 7,198,806 B2 | 4/2007 | Berndt |
| 7,211,557 B2 | 5/2007 | DiMarchi et al. |
| 7,219,664 B2 | 5/2007 | Ruckdeschel et al. |
| 7,223,728 B2 | 5/2007 | Yakubu-Madus et al. |
| D544,093 S | 6/2007 | Eriksen |
| 7,231,919 B2 | 6/2007 | Giroux |
| 7,232,897 B2 | 6/2007 | Hotamisligil et al. |
| 7,234,459 B2 | 6/2007 | Del Bon |
| 7,234,460 B2 | 6/2007 | Greenleaf et al. |
| 7,234,464 B2 | 6/2007 | Goede et al. |
| 7,238,663 B2 | 7/2007 | DeFelippis et al. |
| 7,246,617 B1 | 7/2007 | Harmer et al. |
| D548,330 S | 8/2007 | Cox et al. |
| D548,833 S | 8/2007 | Young et al. |
| 7,258,118 B2 | 8/2007 | Goede et al. |
| 7,259,233 B2 | 8/2007 | Dodd et al. |
| D550,835 S | 9/2007 | Tanaka et al. |
| 7,270,124 B2 | 9/2007 | Rasmussen |
| D552,729 S | 10/2007 | Cox et al. |
| 7,276,534 B2 | 10/2007 | Milstein |
| 7,278,419 B2 | 10/2007 | Gonda |
| 7,278,426 B2 | 10/2007 | Myrman |
| 7,279,457 B2 | 10/2007 | Pohl et al. |
| 7,284,553 B2 | 10/2007 | Hochrainer |
| D557,799 S | 12/2007 | Greenhalgh et al. |
| 7,305,986 B1 | 12/2007 | Steiner et al. |
| 7,306,787 B2 | 12/2007 | Tarara et al. |
| D560,793 S | 1/2008 | Pearl et al. |
| 7,314,859 B2 | 1/2008 | Green et al. |
| 7,316,748 B2 | 1/2008 | Li et al. |
| 7,331,340 B2 | 2/2008 | Barney |
| 7,334,577 B2 | 2/2008 | Gumaste et al. |
| 7,344,734 B2 | 3/2008 | Heijerman et al. |
| 7,368,102 B2 | 5/2008 | Tarara et al. |
| 7,373,938 B2 | 5/2008 | Nichols et al. |
| 7,377,277 B2 | 5/2008 | Hickey et al. |
| 7,387,122 B2 | 6/2008 | Nishibayashi et al. |
| 7,399,528 B2 | 7/2008 | Caponetti et al. |
| 7,401,713 B2 | 7/2008 | Ede et al. |
| 7,402,564 B1 | 7/2008 | Schteingart et al. |
| 7,414,720 B2 | 8/2008 | Wachtel et al. |
| D577,815 S | 9/2008 | Gokhale et al. |
| 7,422,013 B2 | 9/2008 | Burr et al. |
| D579,549 S | 10/2008 | Birath et al. |
| 7,448,375 B2 | 11/2008 | Gonda et al. |
| 7,448,379 B2 | 11/2008 | Yamashita et al. |
| 7,451,761 B2 | 11/2008 | Hickey et al. |
| 7,453,556 B2 | 11/2008 | Hochrainer et al. |
| D583,463 S | 12/2008 | Wood et al. |
| 7,461,653 B2 | 12/2008 | Oliva |
| 7,462,367 B2 | 12/2008 | Schmidt et al. |
| 7,464,706 B2 | 12/2008 | Steiner et al. |
| 7,469,696 B2 | 12/2008 | Yang et al. |
| 7,500,479 B2 | 3/2009 | Nichols et al. |
| 7,503,324 B2 | 3/2009 | Barney et al. |
| 7,504,538 B2 | 3/2009 | Chang et al. |
| 7,517,874 B2 | 4/2009 | Beckett et al. |
| 7,520,278 B2 | 4/2009 | Crowder et al. |
| 7,521,069 B2 | 4/2009 | Patton et al. |
| 7,533,668 B1 | 5/2009 | Widerstrom |
| 7,556,798 B2 | 7/2009 | Edwards et al. |
| 7,559,322 B2 | 7/2009 | Foley et al. |
| D597,657 S | 8/2009 | Kinsey et al. |
| 7,584,846 B2 | 9/2009 | Senter |
| 7,598,222 B2 | 10/2009 | Prouty, Jr. et al. |
| D604,832 S | 11/2009 | Smutney |
| D604,833 S | 11/2009 | Polidoro |
| D605,752 S | 12/2009 | Polidoro |
| D605,753 S | 12/2009 | Smutney |
| 7,625,865 B2 | 12/2009 | Colombo et al. |
| 7,648,960 B2 | 1/2010 | Steiner et al. |
| D613,849 S | 4/2010 | Smutney |
| D614,760 S | 4/2010 | Smutney et al. |
| 7,694,676 B2 | 4/2010 | Wachtel |
| 7,708,014 B2 | 5/2010 | Yamashita et al. |
| 7,709,639 B2 | 5/2010 | Stevenson |
| 7,713,937 B2 | 5/2010 | Schteingart et al. |
| 7,727,963 B2 | 6/2010 | Schteingart et al. |
| 7,735,485 B2 | 6/2010 | Yamashita et al. |
| 7,799,344 B2 | 9/2010 | Oberg |
| 7,803,404 B2 | 9/2010 | Hokenson |
| 7,820,676 B2 | 10/2010 | Leone-Bay et al. |
| 7,842,662 B2 | 11/2010 | Schteingart et al. |
| D629,505 S | 12/2010 | Adamo |
| D629,506 S | 12/2010 | Adamo |
| D629,886 S | 12/2010 | Adamo |
| D629,887 S | 12/2010 | Adamo |
| D629,888 S | 12/2010 | Adamo |
| D635,241 S | 3/2011 | McLean |
| D635,242 S | 3/2011 | Adamo |

(56) References Cited

U.S. PATENT DOCUMENTS

| | | | |
|---|---|---|---|
| D635,243 S | 3/2011 | Kinsey | |
| 7,913,688 B2 | 3/2011 | Cross | |
| D636,868 S | 4/2011 | Kinsey et al. | |
| 7,919,119 B2 | 4/2011 | Straub et al. | |
| 7,943,178 B2 | 5/2011 | Steiner et al. | |
| 7,943,572 B2 | 5/2011 | Cheatham et al. | |
| 7,954,491 B2 | 6/2011 | Hrkach | |
| 7,959,609 B2 | 6/2011 | Gaydos et al. | |
| 8,037,880 B2 | 10/2011 | Zhu et al. | |
| 8,037,881 B2 | 10/2011 | Pentafragas | |
| 8,039,431 B2 | 10/2011 | Wilson et al. | |
| 8,047,203 B2 | 11/2011 | Young et al. | |
| 8,109,267 B2 | 2/2012 | Villax et al. | |
| 8,119,593 B2 | 2/2012 | Richardson | |
| 8,133,514 B2 | 3/2012 | Milstein | |
| 8,146,588 B2 | 4/2012 | Steiner et al. | |
| 8,156,936 B2 | 4/2012 | Steiner et al. | |
| 8,166,970 B2 | 5/2012 | Poole et al. | |
| 8,172,817 B2 | 5/2012 | Michaels et al. | |
| 8,196,576 B2 | 6/2012 | Kriksunov et al. | |
| 8,201,555 B2 | 6/2012 | Chawla | |
| 8,202,992 B2 | 6/2012 | Stevenson | |
| 8,215,300 B2 | 7/2012 | Steiner et al. | |
| 8,217,007 B1 | 7/2012 | Schteingart et al. | |
| 8,227,409 B2 | 7/2012 | Kraft | |
| 8,236,766 B2 | 8/2012 | Schteingart et al. | |
| 8,258,095 B2 | 9/2012 | Boss et al. | |
| 8,278,308 B2 | 10/2012 | Leone-Bay et al. | |
| 8,293,869 B2 | 10/2012 | Bossard | |
| 8,314,106 B2 | 11/2012 | Kraft | |
| 8,372,804 B2 | 2/2013 | Richardson | |
| 8,377,869 B2 | 2/2013 | Richardson | |
| 8,389,470 B2 | 3/2013 | Steiner | |
| 8,394,414 B2 | 3/2013 | Steiner et al. | |
| 8,408,200 B2 | 4/2013 | Clark et al. | |
| 8,420,604 B2 | 4/2013 | Hokenson | |
| 8,424,518 B2 | 4/2013 | Smutney | |
| 8,485,180 B2 | 7/2013 | Smutney | |
| 8,486,894 B2 | 7/2013 | Schteingart et al. | |
| 8,499,757 B2 | 8/2013 | Smutney | |
| 8,512,932 B2 | 8/2013 | Wilson et al. | |
| 8,522,775 B2 | 9/2013 | Malhotra et al. | |
| 8,536,131 B2 | 9/2013 | Schteingart et al. | |
| 8,538,707 B2 | 9/2013 | Adamo | |
| 8,539,946 B2 | 9/2013 | Esteve et al. | |
| 8,551,528 B2 | 10/2013 | Grant et al. | |
| 8,636,001 B2 | 1/2014 | Smutney | |
| 8,671,937 B2 | 3/2014 | Steiner | |
| 8,677,992 B2 | 3/2014 | Villax | |
| 8,763,606 B2 | 7/2014 | Mosier et al. | |
| 8,820,324 B2 | 9/2014 | Smith et al. | |
| 8,925,726 B2 | 1/2015 | Bergey | |
| 2002/0000225 A1* | 1/2002 | Schuler et al. | 128/200.14 |
| 2002/0033177 A1 | 3/2002 | Ohki et al. | |
| 2002/0052381 A1 | 5/2002 | Bar-Or et al. | |
| 2002/0053344 A1 | 5/2002 | Davies et al. | |
| 2002/0053347 A1 | 5/2002 | Ziaee | |
| 2002/0065239 A1 | 5/2002 | Caplan et al. | |
| 2002/0088462 A1 | 7/2002 | Genova et al. | |
| 2002/0101590 A1 | 8/2002 | Shimaoka | |
| 2002/0144680 A1 | 10/2002 | Nilsson et al. | |
| 2002/0161001 A1 | 10/2002 | Kanstrup et al. | |
| 2003/0000524 A1* | 1/2003 | Anderson et al. | 128/203.23 |
| 2003/0010794 A1 | 1/2003 | Herdtle et al. | |
| 2003/0013641 A1 | 1/2003 | Steiner et al. | |
| 2003/0017211 A1 | 1/2003 | Steiner | |
| 2003/0053960 A1 | 3/2003 | Heijerman et al. | |
| 2003/0064097 A1 | 4/2003 | Patel et al. | |
| 2003/0068378 A1 | 4/2003 | Chen et al. | |
| 2003/0099636 A1 | 5/2003 | Epshtein et al. | |
| 2003/0136405 A1 | 7/2003 | Goede et al. | |
| 2003/0194420 A1 | 10/2003 | Holl et al. | |
| 2003/0235538 A1* | 12/2003 | Zierenberg | 424/46 |
| 2004/0024180 A1 | 2/2004 | Drauz | |
| 2004/0025875 A1 | 2/2004 | Reber et al. | |
| 2004/0034014 A1 | 2/2004 | Kanstrup et al. | |
| 2004/0038865 A1 | 2/2004 | Gelber et al. | |
| 2004/0053819 A1 | 3/2004 | Dodd et al. | |
| 2004/0062722 A1 | 4/2004 | Gonda et al. | |
| 2004/0077528 A1 | 4/2004 | Steiner et al. | |
| 2004/0096403 A1 | 5/2004 | Steiner | |
| 2004/0107963 A1 | 6/2004 | Finlay et al. | |
| 2004/0121964 A1 | 6/2004 | Madar et al. | |
| 2004/0138099 A1 | 7/2004 | Draeger | |
| 2004/0151059 A1 | 8/2004 | Roberts, II et al. | |
| 2004/0151774 A1 | 8/2004 | Pauletti et al. | |
| 2004/0157928 A1 | 8/2004 | Kim et al. | |
| 2004/0163648 A1 | 8/2004 | Burton | |
| 2004/0182387 A1 | 9/2004 | Steiner et al. | |
| 2004/0187869 A1 | 9/2004 | Bjorndal et al. | |
| 2004/0204439 A1 | 10/2004 | Staniforth et al. | |
| 2004/0204440 A1 | 10/2004 | Staniforth et al. | |
| 2004/0211419 A1 | 10/2004 | Eason et al. | |
| 2004/0234615 A1 | 11/2004 | Sabetsky | |
| 2004/0234616 A1 | 11/2004 | Sabetsky | |
| 2004/0247628 A1 | 12/2004 | Lintz et al. | |
| 2004/0250812 A1 | 12/2004 | Davies et al. | |
| 2005/0000518 A1 | 1/2005 | Dunkley et al. | |
| 2005/0039743 A1 | 2/2005 | Taylor | |
| 2005/0043228 A1 | 2/2005 | DeFelippis et al. | |
| 2005/0043247 A1 | 2/2005 | Trunk et al. | |
| 2005/0056281 A1 | 3/2005 | Snow | |
| 2005/0070469 A1 | 3/2005 | Bloom | |
| 2005/0080000 A1 | 4/2005 | Thurow et al. | |
| 2005/0119604 A1* | 6/2005 | Bonney et al. | 604/19 |
| 2005/0147581 A1 | 7/2005 | Zamiri et al. | |
| 2005/0153874 A1 | 7/2005 | Cheatham et al. | |
| 2005/0155601 A1 | 7/2005 | Steiner et al. | |
| 2005/0183723 A1 | 8/2005 | Pinon et al. | |
| 2005/0187749 A1 | 8/2005 | Singley | |
| 2005/0214251 A1 | 9/2005 | Pohl et al. | |
| 2005/0252508 A1 | 11/2005 | Koerner | |
| 2005/0265927 A1 | 12/2005 | Lee | |
| 2005/0274378 A1* | 12/2005 | Bonney et al. | 128/200.23 |
| 2006/0000469 A1 | 1/2006 | Tseng | |
| 2006/0040953 A1 | 2/2006 | Leone-Bay et al. | |
| 2006/0041133 A1 | 2/2006 | Stevenson et al. | |
| 2006/0060194 A1 | 3/2006 | Oliva | |
| 2006/0073105 A1 | 4/2006 | Yamashita et al. | |
| 2006/0099269 A1 | 5/2006 | Cheatham et al. | |
| 2006/0120969 A1 | 6/2006 | Nilsson et al. | |
| 2006/0153778 A1 | 7/2006 | Gelber et al. | |
| 2006/0160722 A1 | 7/2006 | Green et al. | |
| 2006/0165756 A1 | 7/2006 | Catani et al. | |
| 2006/0239933 A1 | 10/2006 | Nilsson et al. | |
| 2006/0239934 A1 | 10/2006 | Cheatham et al. | |
| 2006/0243275 A1 | 11/2006 | Ruckdeschel et al. | |
| 2006/0249419 A1 | 11/2006 | Taylor et al. | |
| 2006/0260777 A1 | 11/2006 | Rashba-Step et al. | |
| 2006/0283758 A1 | 12/2006 | Pasbrig | |
| 2007/0020191 A1 | 1/2007 | Boss et al. | |
| 2007/0027063 A1 | 2/2007 | Boss et al. | |
| 2007/0044793 A1 | 3/2007 | Kleinstreuer et al. | |
| 2007/0059373 A1 | 3/2007 | Oberg | |
| 2007/0059374 A1 | 3/2007 | Hokenson et al. | |
| 2007/0074989 A1 | 4/2007 | Merboth et al. | |
| 2007/0086952 A1 | 4/2007 | Steiner | |
| 2007/0099454 A1 | 5/2007 | Gordon | |
| 2007/0125375 A1 | 6/2007 | Finlay et al. | |
| 2007/0151562 A1 | 7/2007 | Jones | |
| 2007/0191462 A1 | 8/2007 | Hettiarachchi | |
| 2007/0196503 A1 | 8/2007 | Wilson et al. | |
| 2007/0207958 A1 | 9/2007 | Bridon et al. | |
| 2007/0225587 A1 | 9/2007 | Burnell et al. | |
| 2007/0235029 A1 | 10/2007 | Zhu et al. | |
| 2007/0240708 A1 | 10/2007 | Schuckmann | |
| 2007/0272763 A1 | 11/2007 | Dunne et al. | |
| 2007/0277821 A1 | 12/2007 | Oliva et al. | |
| 2007/0295332 A1 | 12/2007 | Ziegler | |
| 2008/0015457 A1 | 1/2008 | Silva | |
| 2008/0047550 A2 | 2/2008 | Steiner et al. | |
| 2008/0066739 A1 | 3/2008 | LeMahieu et al. | |
| 2008/0108554 A1 | 5/2008 | Jackson et al. | |
| 2008/0115785 A1 | 5/2008 | Eason et al. | |

(56) References Cited

U.S. PATENT DOCUMENTS

| | | |
|---|---|---|
| 2008/0127970 A1 | 6/2008 | Steiner et al. |
| 2008/0127971 A1 | 6/2008 | King et al. |
| 2008/0127974 A1 | 6/2008 | Lastow |
| 2008/0168987 A1 | 7/2008 | Denny et al. |
| 2008/0190424 A1 | 8/2008 | Lucking et al. |
| 2008/0190425 A1 | 8/2008 | Steiner et al. |
| 2008/0197044 A1 | 8/2008 | Hickey et al. |
| 2008/0202514 A1* | 8/2008 | Kriksunov et al. ...... 128/203.15 |
| 2008/0216824 A1 | 9/2008 | Ooida |
| 2008/0217199 A1 | 9/2008 | Burress et al. |
| 2008/0255468 A1 | 10/2008 | Derchak et al. |
| 2008/0260838 A1 | 10/2008 | Hokenson et al. |
| 2008/0260840 A1 | 10/2008 | Alessi |
| 2008/0295833 A1 | 12/2008 | Rohrschneider et al. |
| 2008/0308580 A1* | 12/2008 | Gaydos et al. ................. 222/333 |
| 2008/0314384 A1 | 12/2008 | Harris et al. |
| 2008/0319333 A1 | 12/2008 | Gavish et al. |
| 2009/0025720 A1 | 1/2009 | Chen |
| 2009/0068274 A1 | 3/2009 | Edwards et al. |
| 2009/0084379 A1 | 4/2009 | Goeckner et al. |
| 2009/0084380 A1 | 4/2009 | Gieschen et al. |
| 2009/0149727 A1 | 6/2009 | Truitt et al. |
| 2009/0151720 A1 | 6/2009 | Inoue et al. |
| 2009/0178676 A1 | 7/2009 | Villax et al. |
| 2009/0205657 A1 | 8/2009 | Barney et al. |
| 2009/0209502 A1 | 8/2009 | Haeberlin et al. |
| 2009/0232891 A1 | 9/2009 | Gelber et al. |
| 2009/0241949 A1 | 10/2009 | Smutney |
| 2009/0250058 A1 | 10/2009 | Lastow |
| 2009/0258818 A1 | 10/2009 | Surolia et al. |
| 2009/0314292 A1 | 12/2009 | Overfield |
| 2009/0320837 A1 | 12/2009 | Smith et al. |
| 2010/0000531 A1 | 1/2010 | Smith et al. |
| 2010/0012120 A1 | 1/2010 | Herder |
| 2010/0086609 A1 | 4/2010 | Steiner et al. |
| 2010/0113363 A1 | 5/2010 | Holst et al. |
| 2010/0163042 A1 | 7/2010 | Bhowmick et al. |
| 2010/0180894 A1 | 7/2010 | Jones et al. |
| 2010/0181225 A1 | 7/2010 | Spallek et al. |
| 2010/0190701 A1 | 7/2010 | Day et al. |
| 2010/0193380 A1 | 8/2010 | Sullivan et al. |
| 2010/0197565 A1 | 8/2010 | Smutney et al. |
| 2010/0212667 A1 | 8/2010 | Smith et al. |
| 2010/0235116 A1 | 9/2010 | Adamo et al. |
| 2010/0238457 A1 | 9/2010 | Adamo et al. |
| 2010/0278924 A1 | 11/2010 | Oberg |
| 2010/0326438 A1 | 12/2010 | Dunne |
| 2011/0000482 A1 | 1/2011 | Gumaste et al. |
| 2011/0003004 A1 | 1/2011 | Hokenson |
| 2011/0011394 A1 | 1/2011 | Edwards et al. |
| 2011/0083667 A1 | 4/2011 | Briant |
| 2011/0158935 A1 | 6/2011 | Kraft |
| 2011/0183901 A1 | 7/2011 | Cheatham |
| 2012/0014999 A1 | 1/2012 | Grant et al. |
| 2012/0040899 A1 | 2/2012 | Costello |
| 2012/0071510 A1 | 3/2012 | Leone-Bay |
| 2012/0094905 A1 | 4/2012 | Costello |
| 2012/0115777 A1 | 5/2012 | Richardson |
| 2012/0122775 A1 | 5/2012 | Boss et al. |
| 2012/0160241 A1 | 6/2012 | Oliva |
| 2012/0164186 A1 | 6/2012 | Grant et al. |
| 2012/0178935 A1 | 7/2012 | Stevenson |
| 2012/0192865 A1 | 8/2012 | Steiner et al. |
| 2012/0207913 A1 | 8/2012 | Smyth |
| 2012/0240929 A1 | 9/2012 | Steiner et al. |
| 2012/0247235 A1 | 10/2012 | Adamo et al. |
| 2012/0247465 A1 | 10/2012 | Wachtel |
| 2012/0328676 A1 | 12/2012 | Leone-Bay et al. |
| 2013/0012710 A1 | 1/2013 | Freeman et al. |
| 2013/0053309 A1 | 2/2013 | Kraft |
| 2013/0104887 A1 | 5/2013 | Smutney et al. |
| 2013/0125886 A1 | 5/2013 | Richardson et al. |
| 2013/0143801 A1 | 6/2013 | Steiner et al. |
| 2013/0189365 A1 | 7/2013 | Hokenson |
| 2013/0199527 A1 | 8/2013 | Smutney et al. |
| 2013/0289278 A1 | 10/2013 | Kraft |
| 2013/0291866 A1 | 11/2013 | Smutney |
| 2013/0291867 A1 | 11/2013 | Smutney |
| 2013/0303445 A1 | 11/2013 | Wilson et al. |
| 2013/0338065 A1 | 12/2013 | Smutney |
| 2014/0007873 A1 | 1/2014 | Smutney |
| 2014/0014106 A1 | 1/2014 | Smutney |
| 2014/0083421 A1 | 3/2014 | Smutney |
| 2014/0096771 A1 | 4/2014 | Remmelgas et al. |

FOREIGN PATENT DOCUMENTS

| | | |
|---|---|---|
| DE | 2840442 C2 | 2/1982 |
| DE | 3639836 A1 | 6/1988 |
| DE | 19519840 A1 | 12/1996 |
| EP | 69715 | 1/1983 |
| EP | 122036 | 10/1984 |
| EP | 143524 | 6/1985 |
| EP | 180543 | 5/1986 |
| EP | 220958 | 5/1987 |
| EP | 237507 | 8/1987 |
| EP | 257915 | 2/1988 |
| EP | 308637 A1 | 3/1989 |
| EP | 360340 | 3/1990 |
| EP | 364235 | 4/1990 |
| EP | 0 387 222 | 9/1990 |
| EP | 388621 A | 9/1990 |
| EP | 606486 | 12/1993 |
| EP | 581473 A1 | 2/1994 |
| EP | 655237 | 5/1995 |
| EP | 666085 A1 | 8/1995 |
| EP | 748213 | 12/1996 |
| EP | 558879 B1 | 5/1997 |
| EP | 844007 | 12/1998 |
| EP | 1060741 A1 | 12/2000 |
| EP | 1114644 | 7/2001 |
| EP | 640354 B1 | 12/2001 |
| EP | 1364967 | 11/2003 |
| EP | 825885 B1 | 3/2004 |
| EP | 96911738 | 6/2004 |
| EP | 1598066 | 11/2005 |
| EP | 833652 B1 | 2/2008 |
| EP | 1923087 A2 | 5/2008 |
| EP | 2060268 A1 | 5/2009 |
| EP | 2314298 A1 | 4/2011 |
| GB | 475440 A | 11/1937 |
| GB | 716815 | 10/1954 |
| GB | 2072536 A | 10/1981 |
| GB | 2148841 A | 6/1985 |
| GB | 2240337 | 7/1991 |
| GB | 2253200 A | 9/1992 |
| GB | 2262452 | 6/1993 |
| GB | 2 398 065 | 8/2004 |
| JP | 63-020301 | 1/1988 |
| JP | 2115154 A | 4/1990 |
| JP | 2-149545 | 2/1992 |
| JP | 09-208485 | 8/1997 |
| JP | 10234827 A | 9/1998 |
| JP | 2002322294 | 11/2002 |
| JP | 2003-503420 | 1/2003 |
| JP | 2004-121061 | 4/2004 |
| JP | 2006-280620 A | 10/2006 |
| WO | 90/13285 | 11/1990 |
| WO | 91/04011 | 4/1991 |
| WO | 91/06287 | 5/1991 |
| WO | 91/16038 | 10/1991 |
| WO | 91/16882 | 11/1991 |
| WO | 91/19524 | 12/1991 |
| WO | 92/04069 | 3/1992 |
| WO | 92/08509 | 5/1992 |
| WO | 93/02712 | 2/1993 |
| WO | 93/14110 | 7/1993 |
| WO | 93/17728 | 9/1993 |
| WO | 93/18754 A1 | 9/1993 |
| WO | 94/00291 | 1/1994 |
| WO | 94/08552 | 4/1994 |
| WO | 94/08599 | 4/1994 |
| WO | 94/19041 | 9/1994 |
| WO | 94/23702 | 10/1994 |

(56) References Cited

FOREIGN PATENT DOCUMENTS

| | | |
|---|---|---|
| WO | 95/00127 A1 | 1/1995 |
| WO | 95/05208 | 2/1995 |
| WO | 95/11666 | 5/1995 |
| WO | 95/24183 A1 | 9/1995 |
| WO | 95/31979 | 11/1995 |
| WO | 95/34294 | 12/1995 |
| WO | 96/01105 | 1/1996 |
| WO | 96/05810 | 2/1996 |
| WO | 96/13250 | 5/1996 |
| WO | 96/22802 A | 8/1996 |
| WO | 96/27386 A1 | 9/1996 |
| WO | 96/36314 | 11/1996 |
| WO | 96/40206 A1 | 12/1996 |
| WO | 97/01365 | 1/1997 |
| WO | 97/04747 | 2/1997 |
| WO | 97/25086 A2 | 7/1997 |
| WO | 97/30743 | 8/1997 |
| WO | 97/46206 | 12/1997 |
| WO | 97/49386 | 12/1997 |
| WO | 98/26827 A1 | 6/1998 |
| WO | 98/39043 | 9/1998 |
| WO | 98/41255 A2 | 9/1998 |
| WO | 98/43615 | 10/1998 |
| WO | 99/14239 A1 | 3/1999 |
| WO | 99/18939 A1 | 4/1999 |
| WO | 99/32510 A1 | 7/1999 |
| WO | 99/33862 | 7/1999 |
| WO | 99/52506 | 10/1999 |
| WO | 00/12116 | 3/2000 |
| WO | 00/33811 A2 | 6/2000 |
| WO | 00/71154 A2 | 11/2000 |
| WO | 01/00654 | 1/2001 |
| WO | 01/81321 A | 1/2001 |
| WO | 01/49274 A2 | 7/2001 |
| WO | 01/51071 | 7/2001 |
| WO | 01/66064 | 9/2001 |
| WO | 01/68169 | 9/2001 |
| WO | 01/07107 | 2/2002 |
| WO | 02/11676 | 2/2002 |
| WO | 02/12201 A1 | 2/2002 |
| WO | 02/47659 A2 | 6/2002 |
| WO | 02/058735 | 8/2002 |
| WO | 02/059574 A1 | 8/2002 |
| WO | 02/067995 A1 | 9/2002 |
| WO | 02/085281 | 10/2002 |
| WO | 02/098348 | 12/2002 |
| WO | 02/102444 | 12/2002 |
| WO | 03/000202 | 1/2003 |
| WO | 03/005547 | 7/2003 |
| WO | 03/057170 | 7/2003 |
| WO | 03/086345 | 10/2003 |
| WO | 03/094951 | 11/2003 |
| WO | 2004/012672 | 2/2004 |
| WO | 2004/012720 | 2/2004 |
| WO | 2004/033010 | 4/2004 |
| WO | 2004/035121 | 4/2004 |
| WO | 2004/041338 | 5/2004 |
| WO | 2004/050152 | 6/2004 |
| WO | 2004/054647 A1 | 7/2004 |
| WO | 2004/056314 | 7/2004 |
| WO | 2004/060458 | 7/2004 |
| WO | 2004/064862 | 8/2004 |
| WO | 2004/075919 | 9/2004 |
| WO | 2004/080401 | 9/2004 |
| WO | 2004/080482 | 9/2004 |
| WO | 2004/103304 A2 | 12/2004 |
| WO | 2005/020964 | 3/2005 |
| WO | 2005/023348 | 3/2005 |
| WO | 2005/028699 A1 | 3/2005 |
| WO | 2005/067964 | 7/2005 |
| WO | 2005/081977 A2 | 9/2005 |
| WO | 2005/089722 | 9/2005 |
| WO | 2005/089843 | 9/2005 |
| WO | 2005/102428 A1 | 11/2005 |
| WO | 2005/102429 | 11/2005 |
| WO | 2005/113042 A1 | 12/2005 |
| WO | 2005/113043 | 12/2005 |
| WO | 2005/120616 | 12/2005 |
| WO | 2006/010248 | 2/2006 |
| WO | 2006/017688 A2 | 2/2006 |
| WO | 2006/023849 | 3/2006 |
| WO | 2006/023943 | 3/2006 |
| WO | 2006/023944 | 3/2006 |
| WO | 2006/037636 | 4/2006 |
| WO | 2006/059939 | 6/2006 |
| WO | 2006/061637 A2 | 6/2006 |
| WO | 2006/086107 A2 | 8/2006 |
| WO | 2006/090149 | 8/2006 |
| WO | 2006/105501 | 10/2006 |
| WO | 2007/007110 A1 | 1/2007 |
| WO | 2007/019229 | 2/2007 |
| WO | 2007/024953 A1 | 3/2007 |
| WO | 2007/030706 | 3/2007 |
| WO | 2007/033316 | 3/2007 |
| WO | 2007/042822 | 4/2007 |
| WO | 2007/068896 | 6/2007 |
| WO | 2007/075534 A2 | 7/2007 |
| WO | 2007/093310 | 8/2007 |
| WO | 2007/098500 | 8/2007 |
| WO | 2007/100535 | 9/2007 |
| WO | 2007/118342 | 10/2007 |
| WO | 2007/118343 A1 | 10/2007 |
| WO | 2007/121411 | 10/2007 |
| WO | 2007/132217 | 11/2007 |
| WO | 2007/132217 A1 | 11/2007 |
| WO | 2007/144607 | 12/2007 |
| WO | 2007/144614 | 12/2007 |
| WO | 2008/001744 | 1/2008 |
| WO | 2008/008021 | 1/2008 |
| WO | 2008/014613 A1 | 2/2008 |
| WO | 2008/020217 | 2/2008 |
| WO | 2008/060484 A2 | 5/2008 |
| WO | 2008/092864 | 8/2008 |
| WO | 2008/110809 | 9/2008 |
| WO | 2009/005546 A1 | 1/2009 |
| WO | 2009/008001 A2 | 1/2009 |
| WO | 2009/009013 A2 | 1/2009 |
| WO | 2009/055030 | 4/2009 |
| WO | 2009/055740 | 4/2009 |
| WO | 2009/055742 | 4/2009 |
| WO | 2009/047281 | 12/2009 |
| WO | 2010/080964 | 7/2010 |
| WO | 2010/102148 | 9/2010 |
| WO | 2010/105094 A1 | 9/2010 |
| WO | 2010/125103 A1 | 11/2010 |
| WO | 2010/144789 | 12/2010 |
| WO | 2011/163272 | 12/2011 |
| WO | 2012/135765 | 10/2012 |
| WO | 2013/063160 A1 | 5/2013 |

OTHER PUBLICATIONS

Vaczek, Accelerating Drug Delivery Firms exploring new drug-delivery routes and devices intently awaiting the commercial launch of Exubera, Magazine, Pharmaceutical & Medical Packaging News, vol. 14, No. 6, Jun. 2006.

Newman, Principles of Metered-Dose Inhaler Design, Journal, Respiratory Care, Sep. 2005, vol. 50, No. 9, pp. 1177-1188, Daedalus Enterprises.

Oberdorster, et al Correlation between Particle Size, In Vivo Particle Persistence, and Lung Injury, Paper, Environ Health Perspect 102 Suppl 5, pp. 173-179, 1994.

Nemmar, et al, Passage of Inhaled Particles into the Blood Circulation in Humans, Journal, Circulation, 2002, pp. 411-414, American Heart Association, Inc.

Oberdorster, Pulmonary effects of inhaled ultrafine particles, Journal, International Archives of Occupational and Environmental Health, 2001, vol. 74, pp. 1-8, Springer-Verlag, Heidelberg.

O'Neill, Air pollution and inflammation in type 2 diabetes: a mechanism for susceptibility, Journal, Occup Environ Med 2007, vol. 64, pp. 373-379.

(56) References Cited

OTHER PUBLICATIONS

Pfutzner, Technosphere/Insulin—A New Approach for Effective Delivery of Human Insulin Via the Pulmonary Route, Journal, Diabetes Technology & Therapeutics, vol. 4, No. 5, 2002, pp. 589-594, Mary Ann Liebert, Inc.
Roumeliotis, New Inhaler launched with a bang, Sep. 25, 2006, in-Pharma Technologist.com, Decision News Media SAS.
Next Generation Inhaler Nears Market, May 1, 2006, Manufacturing Chemist, Cambridge Consultants, Polygon Media Ltd.
Klingler, et al, Insulin-micro-and nanoparticles for pulmonary delivery, Journal, International Journal of Pharmaceutics, vol. 377, pp. 173-179, 2009, Elsevier B.V.
Edwards, et al, Recent advances in pulmonary drug delivery using large, porous inhaled particles, Journal, Journal Applied Physiology, pp. 379-385, American Physiological Society, 1998.
Ferrin, et al, Pulmonary Retention of Ultrafine and Fine Particles in Rats, Journal, Am.J. Respir Cell Mol Biol, May 1992, pp. 535-542.
Insulin Inhalation NN 1998, Drugs R&D, 2004, pp. 46-49, Adis Data Information BV.
Drug Delivery, Easing the Drug-Delivery Route, Jun. 2006, Pharmaceutical & Medical Packaging News, Canon Communications.
Exubera package insert, p. 1.
Exubera Indications, Dosage, Storage, Stability. http://www.rxlist.com/cgi/generic4/exubera_ids.htm.
Pesic "Inhaler delivers more drug to the deep lung, says Cambridge Consultants." in-Pharma Technologist.com, http://www/in-pharmatechnologist.com/content/view/print/344335, Dec. 1, 2010.
Svartengren et al. "Added External Resistance Reduces Oropharyngeal Deposition and Increases Lung Deposition of Aerosol Particles in Asthmatics." Am J Respir Crit Care Med, vol. 152, pp. 32-37, 1995.
Telko et al. "Dry Powder Inhaler Formulation." Respiratory Care, Sep. 2005, vol. 50, No. 9.
Gonzalez et al., Actualizacion del tratamiento farmacologico de la diabetes mellitus tipo 2. Del Sistema Nacional de Salud. vol. 32, No. 1, pp. 3-16 (2008)—full article in Spanish with English abstract.
Skyler, Pulmonary insulin: current status. Diabetes Voice, vol. 51, Issue 1, p. 23-25 (2006).
Wright et al., Inhaled Insulin: Breathing new life into diabetes therapy. Nursing, vol. 37, No. 1, p. 46-48 (2007).
Fadl et al., Effects of MDI spray angle on aerosol penetration efficiency through an oral airway cast. Journal of Aerosol Science, vol. 38, No. 8, pp. 853-864 (2007).
Falsone et al., The Biginelli dihydropyrimidone synthesis using polyphosphate ester as a mild and efficient cyclocondensation/dehydration reagent. Institute of Chemistry, Organic and Bioorganic Chemistry, Karl-Franzens-University, pp. 122-134 (2001).
Farr, S.J. et al., Pulmonary insulin administration using the AERx® system:physiological and physiochemical factors influencing insulin effectiveness in healthy fasting subjects. Diabetes Tech. Ther. 2:185-197, 2000.
Fehmann et al. "Cell and molecular biology of the incretin hormones glucagon-like peptide-1 and glucose-dependent insulin releasing polypeptide." Endocrine Reviews 16:390, 1995.
Festa et al., "LDL particle size in relation to insulin, proinsulin, and insulin sensitivity" Diabetes Care, 22 (10):1688-1693 (1999).
Forst et al., "Metabolic Effects of Mealtime Insulin Lispro in Comparison to Glibenclamide in Early Type 2 Diabetes", Exp. Clin. Endocrinol. Diabetes, 2003, 111, 97-103.
Fritsche et al. "Glimepiride Combined with Morning Insulin Glargine, Bedtime Neutral Protamine Hagedorm Insulin, or Bedtime Insulin Glargine in Patients with Type 2 Diabetes." American College of Physicians 2003.
Galinsky et al., A synthesis of diketopiperazine's using polyphosphoric acid. Journal of the American Pharmaceutical Association, vol. 46, No. 7, pp. 391-393 (1957).
Garber, "Premixed insulin analogues for the treatment of diabetes mellitus", Drugs, 66(1):31-49 (2006).
Garg et al. "Improved glycemic control without an increase in severe hypoglycemic episodes in intensively treated patients with type 1 diabetes receiving morning, evening, or split dose insulin glargine." Diabetes Research and Clinical Practice 66 (2004) 49-56.
Garg SK, Kelly W, Freson B, et al. Treat-to-target Technosphere® insulin in patients with type 1 diabetes. ADA 2011; Abstract 941-P.
Garg SK, McGill JB, Rosenstock J, et al. Technosphere® insulin vs insulin lispro in patients with type 1 diabetes using multiple daily injections. ADA 20917-P.
Gates BJ "Update on advances in alternative insulin therapy." Advances in Pharmacy 1:159-168, 2003.
Glucagon for Injection (1999) glucagon for injection (rDNA origin), pp. 1-7.
Glucagon-like peptide-1; http://en.wikipedia.org/wiki/Glucagon-like peptide-1.
Glucophage Product Insert. Jan. 2009.
Glucotrol Product Insert. Sep. 2006.
Gnudi L, Lorber D, Rosenstock J, et al. Basal/bolus with prandial inhaled Technosphere® insulin (TI) plus insulin glargine qd vs biaspart 70/30 insulin bid in type T2 diabetes mellitus inadequately controlled on insulin with/without oral agents. Diabetologia 2009; 52 (suppl 1).
Goke et al., Exendin-4 is a high potency agonist and truncated exendin-(9-39)-amide an antagonist at the glucagon-like peptide 1-(7-36)-amide receptor of insulin-secreting beta-cells. J. Biol. Chem. 268(26):19650-19655 (1993).
Golpon et al. "Vasorelaxant effect of glucagon-like peptide-(7-36) amide and amylin on the pulmonary circulation of the rat." Regulatory Peptides 102:81, 2001.
Gotfried M, Cassidy JP, Marino MT, et al. Lung deposition and absorption of insulin from Technosphere® insulin. Diabetologia 2009; 52 (suppl 1).
Grant et al "Both insulin sensitivity and maximal glucose elimination rate are reduced in type 2 diabetes." Presented at the American Diabetes Association 65th Scientific Sessions, Jun. 2005, abstract 2202-PO.
Grant et al. "The distribution of 14C-labeled particles following intra-tracheal liquid installation in the Sprague-Dawley rat." Presented at the American Diabetes Association 64th Scientific Sessions, Jun. 2004, abstract 461-P.
Grant M, Harris E, Leone-Bay A, Rousseau K. Technosphere® /insulin: Method of action. Diabetes Technology Meeting 2006; Poster.
Grant ML, Greene S, Stowell GW, et al. Mimicking endogenous peptide secretion by inhalation APS 2009; poster.
Greene et al. "Effects of GLP-1 Technosphere(TM) powder: administered by pulmonary insufflation in male obese Zucker diabetic fat (ZDF) rats." Diabetes Technology Meeting, San Francisco, Oct. 2007.
Greene et al., Greene's protective groups in organic synthesis. 4th ed., pp. 781-783 (2007).
Gupta et al. "Contemporary Approaches in Aerosolized Drug Delivery to the Lung." J. Controlled Research, 17:129-148, 1991.
Gurrieri et al., Thermal condensation of some alpha-aminoacids with phatalic acid. Thermochimica Acta, 7 (1973) 231-239.
Gutniak et al. "Antidiabetogenic action of glucagon-like peptide-1 related to administration relative to meal intake in subjects with type 2 diabetes." J Int Med 250:81, 2001.
Gutniak et al. "Antidiabetogenic effect of glucagon-like peptide-1 (7-36)amide in normal subjects and patients with diabetes mellitus." NEJM 326:1316, 1992.
Gutniak et al. "GLP-1 tablet in type 2 diabetes in fasting and postprandial conditions." Diabetes Care 20:1874, 1997.
Gutniak et al. "Potential therapeutic levels of glucagon-like peptide I achieved in humans by a buccal tablet." Diabetes Care 19:843, 1996.
Gutniak et al. "Subcutaneious injection of the incretin hormone glucagon-like peptide 1 abolishes postprandial glycemia in NIDDM." Diabetes Care 17:1039, 1994.
Guyton et al., "Acute Control of Llocal Blood Flow", Textbook of Medical Physiology, Chapter 17, 10th Edition, W.B. Saunders Company, pp. 176-177, 2000.
Gyore et al., Thermal Analysis, vol. 2—Proceedding Fourth ICTA Budapest 1974; 387-394.
Haak "New developments in the treatment of type 1 diabetes mellitus." Exp Clin Endocrinol Diabetes 107:Suppl 3: S108, 1999.

(56) References Cited

OTHER PUBLICATIONS

Haffner et al., "Proinsulin and insulin concentrations I relation to carotid wall thickness", Strock 29:1498-1503 (1998).
Hagedorn et al. "Protamine Insulin", JAMA, 106:177-180 (1936).
Haino, Takeharu et al. "On-beads Screening of Solid-Attached Diketopiperzines for Calix[5]Arene-Based Receptor." Tetrahedron Letters, 40(20), 3889-3892, 2003.
Halozyme Press Release. Jun. 6, 2009.
Hanley et al., "Cross-sectional and prospective associations between proinsulin and cardovascular disease risk factors in a population experiencing rapid cultural transition" Diabetes Care 24(7): 1240-1247 (2001).
Harsch IA "Inhaled insulins. Their potential in the treatment of diabetes mellitus." Traat. Endicrinol 4:131-138, 2005.
Hassan et al. "A Randomized, Controlled Trial Comparing Twice-a-Day Insulin Glargine Mixed with Rapid-Acting Insulin Analogs Versus Standard Neutral Protamine Hagedorn (NPH) Therapy in Newly Diagnosed Type 1 Diabetes." Pediatrics, 121(3), e466-e472, 2008.
Hassan et al. "In vivo dynamic distribution of 131I-glucagon0like peptide-1 (7-36) amide in the rat studied by gamma camera." Nucl Med Biol 26:413, 1999.
Hausmann et al. "Inhaled insulin as adjunctive therapy in subjects with type 2 diabetes failing oral agents: a controlled proof of concept study." Diabetes Obesity and Metabolism 8:574, 2006.
Hayasaka et al. "Proliferation of type II pneumocytes and alteration in their apical surface membrane antigenicity in pulmonary sarcoidosis." Chest 116:477, 1999.
Pfutzner et al. "Inhaled Technosphere/Insulin Shows a Low Variability in Metabolic Action in Type 2 Diabetic Patients." Diabetes 49 Supplement, May 2000, A121.
Pfuetzner A, Rave K, Heise T, et al. Inhaled Technosphere™/insulin results in low variability in metabolic action in type 2 diabetic patients. Exp Clin Endocrinol Diabetes 2000; 108:S161.
Pfuetzner A, Rave K, Heise T, et al. Low variability in metabolic action in type 2 diabetic patients with inhaled Technosphere/insulin. Diabetologia 2000; 43:Abstract 774.
Phillips M, Amin N, Boss AH, et al. Pulmonary functions (over 2 years) in diabetic subjects treated with Technosphere® insulin or usual antidiabetic treatment. Diabetologia 2009; 52 (suppl 1).
Pohl R, Muggenberg BA, Wilson BR, et al. A dog model as predictor of the temporal properties of pulmonary Technosphere/insulin in humans. Respiratory Drug Delivery 2000; VII: 463-465.
Polonsky et al. "Abnormal Patterns of Insulin Secretion in Non-insulin-Dependent Diabetes Mellitus." N Eng J Med 318:1231-39, 1988.
Potocka E, Amin N, Cassidy J, et al. Insulin pharmacokinetics following dosing with Technosphere® insulin in subjects with chronic obstructive pulmonary disease. Current Medical Research and Opinion 2010; 26:2347-2353.
Potocka E, Baughman R A, Derendorf H. Population pharmacokinetic model of human insulin following different routes of administration. Journal of Clinical Pharmacology 2011;51:1015-1024.
Potocka E, Baughman R, Derendorf H. Population Pharmacokinetic Model of Regular Human Insulin Following Different Routes of Administration. AAPS Journal. 2009; 11(S1). Available from: http://www.aapsj.org. Presented at the 2009 AAPS (American Association of Pharmaceutical Scientists) National Biotechnology Conference, Jun. 21-24, Seattle, WA.
Potocka E, Baughman RA, Derendorf J. A population PK/PD model of Technosphere® insulin administered to healthy and type 2 diabetics. ADA 2010; Poster 624.
Potocka E, Baughman RA, Schwartz SL, et al. Pharmacokinetics of AFRESA® unchanged in patients with chronic obstructive pulmonary function ADA 2009; Poster 437.
Potocka E, Cassidy J P, Haworth P, et al. Pharmacokinetic characterization of the novel pulmonary delivery excipient fumaryl diketopiperazine. Journal of diabetes science and technology 2010;4:1164-1173.
Potocka E, Cassidy JP, Haworth P, et al. Pharmacokinetic characterization of fumaryl diketopiperazine. Third International Conference on Advanced Technologies and Treatments for Diabetes 2010; Poster 291.
Potocka E, Hovorka R, Baughman R, et al. Characterization of metabolism parameters following Technosphere® insulin and insulin Lispro. ADA 2010; Poster 1561.
Potocka E, Hovorka R, Baughman RA, et al. AFRESA™ supresses endogenous glucose production earlier than a rapid-acting analog (Lispro) and inhaled Exubera® ADA 2009; Oral 232.
Potocka E, Hovorka R, Baughman RA, et al. Technosphere® insulin suppresses endogenous glucose production earlier than a rapid-acting analog (lispro) and an inhaled insulin (exubera). Diabetologia 2009; 52 (suppl 1).
Prabhu et al. "A study of factors controlling dissolution kinetic of zinc complexed protein suspensions in various ionic species", Int. J. Pharm. 217(1-2):71-8 (2001).
Pulmonary Delivery: Innovative Technologies breathing new life into inhalable therapeutics, Ondrug Delivery, MannKind, pp. 1-24 (2006).
Quattrin et al. "Efficacy and Safety of Inhaled Insulin (Exubera) Compared with Subcutaneous Insulin Therapy in Patients with Type 1 Diabetes." Diabetes Care, vol. 27, No. 11, Nov. 2004, p. 2622-2627.
Quddusi et al. "Differential effects of acute and extended infusions of glucagon-like peptide-1 on first- and second-phase insulin secretion in diabetic and nondiabetic humans." Diabetes Care 26:791, 2003.
Rachman et al. "Normalization of insulin responses to glucose by overnight infusion of glucagon-like peptide 1 (7-36) amide in patients with NIDDM." Diabetes 45:1524, 1996.
Raju et al., Naseseazines A and B: a new dimeric diketopiperazine framework from a marine-derived actinomycete, *Streptomyces* sp. Organic letters, vol. 11, No. 17, pp. 3862-3865 (2009).
Raskin et al. "Continuous subcutaneous insulin infusion and multiple daily injection therapy are equally effective in type 2 diabetes." Diabetes Care, vol. 26, No. 9, pp. 2598-2603, Sep. 2003.
Raskin P, Heller S, Honka M, et al. Pulmonary function over 2 years in diabetic patients treated with prandial inhaled Technosphere® Insulin or usual antidiabetes treatment: A randomized trial. Diabetes, Obesity and Metabolism 2012;14:163-173.
Raskin P, Philips M, Amin N, et al. Hypoglycemia in patients with type 1 diabetes incorporating prandial inhaled Technosphere® insulin into their usual diabetes treatment regimen vs continuing their usual diabetes management. AACE 2010; Poster 283.
Raskin P, Phillips MD, Rossiter A, et al. A1C and hypoglycemia in patients with type 2 diabetes mellitus incorporating prandial inhaled Technosphere® insulin into their usual antihyperglycemic regimen vs continuing their usual antihyperglycemic regimen. ADA 2010; Abstract 359-OR.
Raufman et al., Exendin-3, a novel peptdie from Heloderma horridum venom, interacts with vasoactive intestinal peptide receptors and a newly described receptor on dispersed aciin from guinea pig pancreas. J. Biol. Chem. 266(5) : 2897-2902 (1991).
Raufman et al., Truncated glucagon-like peptide-1 interacts with exendin receptors on dispersed acini from guina pig pancreas. J. Biol. Chem. 267(30) : 21432-21437 (1992).
Raun et al. "Liraglutide, a long-acting glucagon-like peptide-1 analog, reduces body weight and food intake in obese candy-fed rats, where as a dipeptidyl peptidase-IV inhibitor, vildagliptin, does not." Diabetes 56:8, 2007.
Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.
Rave et al. "Dose Response of Inhaled Dry-Powder Insulin and Dose Equivalence to Subcutaneous Insulin Lispro." Diabetes Care 28:2400-2405, 2005.
Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.
Rave et al. "Results of a Dose-Response Study with a New Pulmonary Insulin Formulation and Inhaler." Diabetes 49, Supplement, May 2000, A75.

(56) References Cited

OTHER PUBLICATIONS

Rave et al. "Time-action profile of inhaled insulin in comparison with subcutaneously injected insulin lispro and regular human insulin." Diabetes Care 28:1077, 2005.

Rave K, Heise T, Pfuetzner A, et al. Assessment of dose-response characteristics for a new pulmonary insulin formulation and inhaler. Exp Clin Endocrinol Diabetes 2000; 108:S161.

Rave K, Potocka E, Boss AH, et al. Pharmacokinetics and linear exposure of AFRESA™ compared with the subcutaneous injection of regular human insulin Diabetes, Obesity and Metabolism 2009; 11:715-720.

Raz et al. "Pharmacodynamics and Pharmacokinetics of Dose Ranging Effects of Oralin versus S.C. Regular Insulin in Type 1 Diabetic Patients." Fourth Annual Diabetes Technology Meeting, Philadelphia PA, 2004.

Razavi et al. "TRPVI+ sensory neurons control beta cell stress and islet inflammation in autoimmune disease." Cell 127:1123, 2006.

Retrieved from website: http://groups.molbiosci.northwestern.edu/holmgren/Glossary/Definitions/Def-P/placebo.html, 1 page, Retrieved on Mar. 12, 2013.

Rhodes et al. "Technosphere: Microspherical Particles from Substituted Diketopiperazines for Use in Oral Drug Delivery." 208th ACS National Meeting, Aug. 1994.

Richardson et al. "Technosphere Insulin Technology." Diabetes Technology & Therapeutics, vol. 9, Supplement 1, pp. S65-S72, 2007.

Richardson PC, Potocka E, Baughman RA, et al. Pharmacokinetics of Technosphere® insulin unchanged in patients with chronic obstructive pulmonary disease. Diabetologia 2009; 52 (suppl 1).

Richter et al. "Characterization of glucagon-like peptide-1(7-36)amide receptors of rat membranes by covalent cross-linking." FEBS Letters 280:247, 1991.

Richter et al. "Characterization of receptors for glucagon-like peptide-1 (7-36)amide on rat lung membranes." FEBS Letters 267:78, 1990.

Riddle "Combining Sulfonylureas and Other Oral Agents." Am J Med, 2000, vol. 108(6A), pp. 15S-22S.

Riddle et al. "Emerging therapies mimicking the effects of amylin and glucagon-like peptide 1." Diabetes Care 29:435, 2006.

Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.

Rosen et al., Substance P microinjected into the periaqueductal gray matter induces antinociception and is released folloing morphine administration. Brain Research, 1001: 87-94 (2004).

Rosenmund et al., Diketopiperazines from Leuchs Anhydrides. Angew Chem Intern. Edit. vol. , No. 2 (1970).

Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.

Cheatham et al. "Prandial Technosphere® /Insulin inhalation provides significantly better control of meal-related glucose excursions than prandial subcutaneous insulin." Presented at the Diabetes Technology Society meeting, Oct. 2004.

Chelikani et al., Intravenous infusion of glucagon-like peptide-1 potently inhibits food intake, sham feeding, and gastric emptying in rats. Am J Physiol. Regul. Integr. Comp. Physiol., 288(6):R1695-706, 2005.

Chemical Abstracts, vol. No. 114(22), Abstract No. 214519x (1990).

Chemicaland21.com. Solvents. Dec. 12, 2008. Available from: <http://web.archive.org/web20081212035748/http://www.chemicalland21.com/info/SOLVENTS.htm.

Chow et al., Particle Engineering for Pulmonary Drug Delivery. Pharmaceutical Research, vol. 24, No. 3, pp. 411-437 (2007).

Clee et al. Nature Genetics 38:688-693, 2006.

Cobble "Initiating and Intensifying Insulin Therapy for Type 2 Diabetes: Why, When, and How." Am J Ther. Jan. 8, 2009.

Coffey et al. "Valuing heath-related quality of life in diabetes." Diabetes Care 25:2238, 2002.

Colagiuri et al., Are lower fasting plasma glucose levels at diagnosis of type 2 diabetes associated with improved outcomes? Diabetes Care, vol. 25, pp. 1410-1417 (2002).

Combettes and Kargar, C, Newly Approved and Promising Antidiabetic Agents. Therapie, Jul.-Aug. 2007: 62 (4): 293-310.

Coors et al., Polysorbate 80 in medical products and nonimmunologic anaphylactoid reactions. Ann. Allergy Astha Immunol., 95(6): 593-599 (2005).

Costello et al., "Zinc inhibition of mitochondrial aconitase and its importance in citrate metabolism in prostate epithelial cells", Journ. Biol. Chem. 272(46):28875-28881 (1997).

Cricket TM Single-Use Inhalers [on-line]. Mannkind Technologies Website, posted in 2011, [retrieved on Jul. 30, 2012]. Retrieved from the Internet. <URL:mannkindtechnologies,com/DeviceTechnology/CricketSingleUseInhalers.aspx>.

Crosby, J. "Dog Normals", <http://vetmedicine.about.com/od/diseasesconditionsfaqs/tp/TP_dogfacts.htm>, copyright 2013.

Cruetzfeldt et al. "Glucagonostatic actions and reduction of fasting hyerglycemia by exogenous glucagon-like peptide i(7-36) amide in type 1 diabetic patients." Diabetes Care 19:580, 1996.

D'Alessio et al., Elimination of the action of glucagon-like peptide 1 causes an impairment of glucose tolerance after nutrient ingestion by healthy baboons. J. Clin. Invest., 97:133-38 (1996).

Database adisinsight, "Gucagon-like peptide-1 inhalation-Mannkind Corporation", Database accession No. 2009:1048 Abstract.

Davis "Postprandial Physiology and the Pathogenesis of Type 2 Diabetes Mellitus." Insulin, vol. 3, Apr. 1, 2008, pp. 132-140.

De Heer et al. "Sulfonylurea compounds uncouple the glucose dependence of the insulinotropic effect of glucagon-like peptide-1." Diabetes 56:438, 2007.

Deacon "Therapeutic strategies based on glucagon-like peptide 1." Diabetes. Sep;53(9):2181-9, 2004.

Deacon et al., "Glucagon-like peptide 1 undergoes differential tissue-specific metabolism in the anesthetized pig", Am. J. Physiol. 271 (Endocrino. Metab. 34): E458-E464, 1996.

Decode study group. "Glucose tolerance and mortality: comparison of WHO and American Diabetes Association diagnostic criteria. " Lancet. Aug. 21, 1999;354(9179):617-21.

DedicatedPhase, "Preclinical Trials and Research", <http://www.dedicatedphase1.com/preclinical-research.html>, copyright 2006-2011, p. 1.

Definition of analog from http://cancerweb.ncl.ac.uk/omd/about.html, pp. 1-5. Accessed by Examiner on Jul. 7, 2005 and cited in Office Action issued on Jul. 26, 2013 in U.S. Appl. No. 12/830,557.

Del Prato S "Unlocking the opportunity of tight glycemic control" Diabetes Obesity and Metabolism 7:S1-S4, 2005.

Delgado-Aros et al. "Effect of GLP-1 on gastric volume, emptying, maximum volume ingested and postprandial symptoms in humans." Am J Physiol Gastrointest Liver Physiol 282:G424, 2002.

Diabetes: Counting Carbs if You Use Insulin, WedMD, http://diabetes.webmd.com/carbohydrate-counting-for-people-who-use-insulin#m Oct. 1, 2010.

Diez et al. "Inhaled insulin—a new therapeutic option in the treatment of diabetes mellitus" Expert Opin. Pharmacother., 2003, 4, 191-200.

Dorwald, F.A. Side reactions in organic synthesis. Wiley, (2005).

Doyle et al. "Glucagon-like peptide-1." Recent Prog Horm Res. 2001;56:377-99.

Dreamboat TM Reusable Inhalers [on-line]. Mannkind Technologies Website, posted in 2011, Retrieved from the Internet: <URL: mannkindtechnologies.com/Device Technology/Dream Boat Reuseable Inhalers.aspx>.

Drucker "Development of glucagon-like peptide-1-based pharmaceuticals as therapeutic agents for the treatment of diabetes." Curr Pharma Design 7:1399, 2001.

Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.

Drucker et al., Minireview: The glucagon-like peptides. Endocrinology, vol. 142, No. 2, pp. 521-527 (2001).

(56) References Cited

OTHER PUBLICATIONS

Dungan et al., Glucagon-like peptide 1-based therapies for type 2 diabetes: a focus on exntadtide. Clinical Diabetes, 23: 56-62 (2005).
Dunn, "Zinc-ligand interactions modulate assembly and stability of the insulin hexamer", Biometals, 18(4):295-303 (2005).
Edelman "Type II Diabetes Mellitus." Adv Int Med, 43:449-500, 1998.
Edited by Fukushima, Masanori, "Arterial Sclerosis," Merck Manual 17th, Japanese Edition, NIKKEI BP Corp., p. 1659-1663, 1999.
Edwards CMB et al. "Cardiovascular and pancreatic endocrine response to glucagon-like peptide-1(7-36) amide in the conscious calf." Exp Physiol 82:709, 1997.
Edwards CMB et al. "Subcutaneous glucagon-like peptide-1(7-36) amide is insulinotropic and can cause hypoglycaemia in fasted healthy subjects." Clinical Science 96:719, 1998.
Eggers et al., Molecular confinement influences protein structure and enhances thermal protein stability. Protein Sci., 10:250-261 (2001).
Ehlers et al. "Recombinant glucagon-like peptide-1 (7-36 amide) lowers fasting serum glucose in a broad spectrum of patients with type 2 diabetes." Horm Metab Res 35:611, 2003.
Eissele et al., Rat gastric somatostatin and gastrin relase: interactions of exendin-4 and truncated glucagon-like peptide-1 (GLP-1) amide. Life Sci., 55(8):629-634 (1994).
Elliot et al., Parenteral absorption of insulin from the lung in diabetic children. Austr. Paediatr. J. 23: 293-297 (1987).
Elrick et al. "Plasma insulin response to oral and intravenous glucose administration." J Clin Endocr 24:1076, 1964.
Engelgau MM "Screening for type 2 diabetes." Diabetes Care 23:1563-1580, 2000.
Engwerda et al., Improved pharmackinetic and pharmacodynamic profile of rapid-acting insulin using needle-free jet injection technology. Diabetes Care, vol. 34, Aug. 2011, pp. 1804-1808.
Erlanger et al., Phosphorous pentoxide as a reagent in peptide synthesis. College of Physicians and Surgeons—Columbia Univeristy, vol. 26, pp. 2534-2536 (1960).
Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, 2008.
Rosenstock et al. "Inhaled Insulin Improves Glycemic Control when Substituted for or Added to Oral Combination Therapy in Type 2 Diabetes." Ann Intern Med 143:549-558, 2005.
Rosenstock et al., "Reduced hypoglycemia risk with insulin glargine: a meta-analysis comparing insulin glargine with human NPH insulin in type 2 diabetes", Diabetes Care, 28(4):950-5 (2005).
Rosenstock J, Baughman RA, Ribera-Schaub T, et Al. A randomized, double-blind, placebo controlled study of the efficacy and safety of inhaled Technosphere® insulin in patients with type 2 diabetes (T2DM). Diabetes 2005;54: Abstract 357-OR.
Rosenstock J, Lorber D, Petrucci R, et al. Basal/bolus with prandial inhaled Technosphere® insulin (TI) plus insulin glargine qd vs biaspart 70/30 insulin bid in T2 DM inadequately controlled on insulin with/without oral agents ADA 2009; Poster 466.
Rosenstock J, Lorger DL. Gnudi L, et al.Prandial inhaled insulin plus basal insulin glargine versus twice daily biaspart insulin for type 2 diabetes: a multicentre randomised trial. Lancet 2010;375:2244-2253.
Rossiter A, Amin N, Harris R, et al. Pulmonary safety of inhaled Technosphere® insulin therapy in adults with diabetes using high-resolution computerized tomography of the chest. Diabetologia 2009; 52 (suppl 1).
Rossiter A, Howard C, Amin N, et al. Technosphere® insulin: Safety in type 2 diabetes mellitus. ADA 2010; Poster 523.
Rousseau et al. "Drug delivery by fumaryl diketopiperazine particles: evidence for passive transport." Presented at the American Diabetes Association 64th Scientific Sessions, Jun. 2004, abstract 484-P.
Rubin RR, Peyrot M. Psychometric properties of an instrument for assessing the experience of patients treated with inhaled insulin: The inhaled insulin treatment questionnaire (INTQ) Health & Quality of Life Outcomes 2010.8:32.
Rubin RR, Peyrot M; Patient reported outcomes in adults with type 1 diabetes using mealtime AFRESA® (inhaled Technosphere® insulin) or rapid acting insulin with basal insulin ADA 2009; Poster 1881.
Ryan EA et al. "Successful islet transplantation. Continued insulin reserve provides long-term glycemic control." Diabetes 51:2148-2157, 2002.
Sajeesh et al., Cyclodextrin-insulin complex encapsulated polymethacrylic acid based nanoparticles for oral insulin delivery. International Journal of Pharmaceuticals, 2006, 325, pp. 147-154.
Sakagami M et al. "Respirable microspheres for inhalation: the potential of manipulating pulmonary disposition for improved therapeutic efficacy." Clin Pharmacokinet 44(3):263-277, 2005.
Sakr, A new approach for insulin delivery via the pulmonary route: design and pharmacokinetics in non-diabetic rabbits. International Journal of Pharmaceutics, 86: 1-7 (1992).
Salib, Utilization of sodium alginate in drug microencapsulation. Pharazeutische Industrie, 40(11a): 1230-1234 (1978).
Saraceni C et al. "Effects of glucagon-like peptide-1 and long-acting analogues on cardiovascular and metabolic function." Drugs R D 8:145, 2007.
Sarrach et al., "Binding and entrapment of insulin by liposomes made of lecithin-phosphotidix acid in acid solution" Pharmazie 40:642-645, 1985 (German and English Abstract).
Savage et al., "Effects of peptide YY (PYY) on mouth to caecum intestinal transit time and on the rate of gastric emptying healthy volunteers", Gut, vol. 28, pp. 166-170, 1987.
Sawhney et al., Bioerodible hydrogels based on photopolymerized poly(ethylene glycol)-co-poly(a-hydroxy acid) diacrylate macromers. Macromolecules, 26: 581-587 (1993).
Schaffer et al. "Assembly of high-affinity insulin receptor agonists and antagonists from peptide building blocks." PNAS 100:4435-4439, 2003.
Schepp et al., Eur. J. Pharmacol., 269:183-91, 1994.
Scherbaum "Unlocking the opportunity of tight glycaemic control. Inhaled insulin: clinical efficacy." Diabetes Obesity and Metabolism 7:S9-S13, 2005.
Schirra et al. "Gastric emptying and release of incretin hormones after glucose ingestion in humans." J Clin Invest 97:92-103, 1996.
Schluter et al., "Pulmonary Administration of Human Insulin in volunteers and Type I Diabetics", Diabetes, 33, (Suppl) 298 (1984).
Schneider et al., "Stimulation by proinsulin of expression of plasminogen activator inhibitor type 1 in endothelial cells", Diabetes 41(7):890-895 (1992).
Schon, Istvan et al. "Formation of Aminosuccinyl Peptides During Acidolytic Deprotection Followed by their Tranformation to Piperazine-2, 5-dione Derivatives in Neutral Media." International Journal of Peptide & Protein Research, 14(5), 485-494, 1979.
Schroder, "Crystallized carbohydrate spheres as a slow release matrix for biologically active substances", Biomaterials 5:100-104, 1984.
Scrocchi et al. "Glucose intolerance but normal satiety in mice with a null mutation in the glucagon-like peptide 1 receptor gene." Nature Medicine 2:1254-1258, 1996.
Seshiah & Balaji, "Early Insulin Therapy in Type 2 Diabetics", Int. J. Diabetes in Developing Countries, 2003, 23, 90-93.
Seville, P.C. et al., Preparation of dry powder dispersions for non-viral gene delivery by freeze-drying and spray drying. J. Gene Medicine 2002; 4:428-437.
Shah et al. "Lack of suprression of glucagon contributes to postprandial hyperglycemia in subjects with type 2 diabetes mellitus." J Clin Indocrinol Metab 85:4053, 2000.
Shelly et al. "Polysorbate 80 hypersensitivity." The Lancet 345:1312, 1995.
Shojania et al. "Effect of quality improvement strategies for type 2 diabetes on glycemic control." JAMA 296:427, 2006.
Silverstein et al., "Care of Children and Adolescens with Type 1 Diabetes, A Statement of the American Diabetes Association", Diabetes Care, Jan. 2005, vol. 28, pp. 186-212.
Singh et al., Use of 125I-[Y39]exendin-4 to characterize exendin receptors on dispersed pancreatic acini and gastric chief cells from guinea pig. Regul. Pept. 53 : 47-59 (1994).

(56) References Cited

OTHER PUBLICATIONS

Simms JR, Carballo I, Auge CR, et al. Assessment of immunotoxic effects on humoral and cellular immune parameters following repeated inhalation of Technosphere insulin in the rat. Diabetes 2005;54:Abstract 2078-PO.
Skyler "Pulmonary Insulin Delivery—State of the Art 2007." Diabetes Tecnology & Therapeutics, vol. 9, Supplement 1, pp. S1-S3. 2007.
Skyler JS et al. "Use of inhaled insulin in a basal/bolus insulin regimen in Type 1 diabetic subjects." Diabetes Care 28:1630-1635, 2005.
Smith et al. "New-onset diabetes and risk of all-cause and cardiovascular mortality." Diabetes Care 29:2012, 2006.
Smutney CC, Friedman EM, Amin N. Inspiratory efforts achieved in use of the Technosphere® insulin inhalation system. Diabetes Technology Meeting 2008; Poster SMUT8052.
Smutney CC, Friedman EM, Amin N. Inspiratory efforts achieved in use of the Technosphere® insulin inhalation system. Journal of Diabetes Science and Technology 2009 3(5):1175-1189.
Smutney CC, Polidoro JM, Adamo B, et al. In-vitro performance improvement realized in a next generation dry powder delivery system. Diabetes Technology Meeting 2009; poster.
Smutney CC, Polidoro JM, Adamo B, Shah S. In vitro performance improvement realized in a next generation dry powder delivery system. Third International Conference on Advanced Technologies and Treatments for Diabetes 2010; Poster 122.
Smutney CC, Polidoro JM. Easy-to-use next-generation pulmonary insulin delivery system. ADA 2010; Abstract 2093.
Smutney CC, Polidoro JM. Improvements realized in a next-generation pulmonary insulin delivery system. ADA 2010; Abstract 2097.
Sodium chloride is a natural product from http://www.wqpmag.com/potassium-chloride-vs-sodium-chloride, pp. 1-3. Accessed by Examiner on May 16, 2014 and cited by Examiner in Non-Final Offfice Action dated May 22, 2014 for U.S. Appl. No. 13/797,657 and cited by Examiner in Non-Final Office Action dated May 22, 2014 for U.S. Appl. No. 12/883,369.
Johnson et al., "Turbuhaler a new device for dry powder terbutaline inhalation", Allergy 43(5):392-395 (1988).
Johnson et al: RyR2 and calpain-10 delineate a novel apoptosis pathway in pancreatic islets. J Biol Chem., 279 (23):24794-802, 2004.
Johnson, Keith A., Preparation of peptide and protein powders for inhalation. Advanced Drug Delivery Reviews 1997; 26:3-15.
Jones et al., An investigation of the pulmonary absorption of insulin in the rat. Third European Congress of Biopharmaceutics and Pharmacokinetics, (1987).
Joseph et al. "Oral delivery of glucagon-like peptide-1 in a modified polymer preparation normalizes basal glycaemia in diabetic db/db mice." Diabetologia 43:1319-1328, 2000.
Joy et al. "Incretin mimetics as emerging treatments for type 2 diabetes." Annal Pharmacother 39:110, 2005.
Juntti-Berggren et al. "The antidiabetogenic effect of GLP-1 is maintained during a 7-day treatment period and improves diabetic dyslipoproteinemia in NIDDM patients." Diabetes Care 19:1200-1206, 1996.
Kanse et al. "Identification and characterization of glucagon-like peptide-1 7-36 amide-binding sites in the rat brain and lung." FEBS Letters 241:209, 1988.
Kapitza C et al. "Impact of particle size and aerosolization time on the metabolic effect of an inhaled insulin aerosol." Diabetes Tech Ther 6:119, 2004.
Kapitza et al. "Dose-response characteristics for a new pulmonary insulin formulation and inhaler." Presented at the 35th Annual Meeting of the EASD, Sep. 2000, abstract OP29 184.
Kapsner P, Bergenstal RM, Rendell M, et al. Comparative efficacy and safety of Technosphere® insulin and a rapid-acting analog both given with glargine in subjects with type 1 diabetes in a 52-week study. Diabetologia 2009; 52 (suppl 1).
Katchalski E et al. "Synthesis of lysine anhydride", J. Amer Chem Soc 68:879-880, 1946.
Katz et al. "Quantitative insulin sensitivity check index: a simple, accurate method for assessing insulin sensitivity in humans." J. Clin. Endocrinol. Metab. 85:5402-2410, 2000.
Kaur et al. "A Delineation of Diketopiperazine Self-Assembly Processes: Understanding the Molecular Events Involved in Nε-(Fumaroyl)diketopiperazine of L-Lys (FDKP) Interactions." Molecular Pharmaceutics, vol. 5, No. 2, 294-315, 2008.
Kawai et al. "Evidence that glucagon stimulates insulin secretion through its own receptor in rats." Diabetologia 38:274, 1995.
Kawamori et al. "Does hyperinsulinemia accelerate atherosclerosis?" Department of Medicine, Juntendo University School, vol. 13, No. 12, p. 954-960, 1994.
Kelley, D. et al. "Impaired postprandial glucose utilization in non-insulin dependent diabetes mellitus." Metabolism 43:1549-1557, 1994.
Kenny AJ et al. "Dipeptidyl peptidase IV, a kidney brush-border serin peptidase." Biochem J. 155:169, 1976.
Kim et al. "Development and characterization of a glucagon-like peptide 1-albumin conjugate. The ability to activate the glucagon-like peptide 1 receptor in vivo." Diabetes 52:751, 2003.
Kinzig et al. "The diverse roles of specific GLP-1 receptors in the control of food intake and the response to visceral illness." J Neurosci 22:10470, 2002.
Kirk et al. "Disparities in HbA1c levels between African-American and non-hispanic white adults with diabetes." Diabetes Care 29:2130, 2006.
Kitabchi, Proinsulin and C-peptide:a review. May 26, 1977 (5):547-87, http://www/ncbi.nlm.nih.gov/pubmed/403392.
Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.
Kohler D et al. Non-radioactive approach for measuring lung permeability: inhalation of insulin. Atemw Lungenkrkh 13:230-232, 1987. (Original German and English translation attached).
Kohler, "Aerosols for Systemic Treatment", Lung (Suppl.) 677-684 (1990).
Komada et al., Intratracheal delivery of peptide and protein agents: absorption from solution and dry powder by rat lung. J. Pharm. Sci. 83(6): 863-867 (1994).
Komatsu et al. "Glucagonostatic and insulinotropic action of glucagon-like peptide-1 (7-36)-amide." Diabetes 38:902, 1989.
Koning et al., Relationship between inspiratory flow through simulated dry powder inhalers and peak maximal inspiratory pressure. Dry powder inhalation: technical and physiological aspects, prescribing and use. Chapter 3, 2001, pp. 43-56.
Kontny et al., Issues Surrounding MDI Formulation Development with Non-CFC Propellants), J. Aerosol Med 4(3), 181-187 (1991).
Kopple et al. "A convenient synthesis of 2,5-piperazinediones." J Org Chem p. 962, 1967.
Kraft KS, Grant M. Preparation of macromolecule-containing drug powders for pulmonary delivery Methods in Molecular Biology 2009;480:165-174.
Kreymann B et al. "Glucagon-like peptide-1 7-36: a physiological incretin in man." The Lancet, Dec. 5, 1987, p. 1300.
Krssak, M. et al. "Alterations in postprandial hepatic glycogen metabolism in type 2 diabetes." Diabetes 53:3048-3056, 2004.
Krueger et al. "Toxicological profile of pulmonary drug delivery agent." Presented at the American Diabetes Association 64th Scientific Sessions, Jun. 2004, abstract 465-P.
Kwon et al. "Signaling elements involved in the metabolic regulation of mTOR by nutrients, incretins, and growth factors in islets." Diabetes 53:S225, 2004.
Lankat-Buttgereit B et al. "Molecular cloning of a cDNA encoding for the GLP-1 receptor expressed in rat lung." Exp Clin Endocrinol 102:241, 1994.
Laureano et al. "Rapid absorption and elimination of insulin from the lung following pulmonary administration of Technosphere® /Insulin: A pharmacokinetic study in a rat model." Presented at the American Diabetes Association 65th Scientific Sessions, Jun. 2005, abstract 445-P.

(56) References Cited

OTHER PUBLICATIONS

Leahy et al. Beta-cell dysfunction in type II diabetes mellitus. Curr Opin Endocrinol Diabetes 2:300-306, 1995.
Lebovitz "Therapeutic options in development for management of diabetes: pharmacologic agents and new technologies." Endocr Pract 12:142, 2006.
Lee et al. "Synthesis, characterization and pharmacokinetic studies of PEGylated glucagon-like peptide-1." Bioconjugate Chem 16:377, 2005.
Lee et al., "Development of an Aerosol Dosage Form Containing Insulin", J. Pharm. Sci. 65(4), 567-572 (1976).
Leiner et al. "Particles facilitate the absorption of insulin in a primary cell culture model of alveolar epithelium without evidence of cytotoxicity." Presented at the American Diabetes Association 64th Scientific Sessions, Jun. 2004, abstract 467-P.
Leiner et al. "The pharmacokinetic profile of insulin administered by inhalation in the rat." Diabetes 53 Supplement, Jun. 2004, A111.
Leone-Bay et al. "Evaluation of novel particles as an inhalation system for GLP-1." Diabetes, Obesity and Metabolism. 11:1050-1059, 2009.
Leone-Bay A, Grant M. Technosphere® Technology: A Platform for inhaled protein therapeutics. OndrugDelivery 2006 (published online).
Leone-Bay A, Grant M. Technosphere® /insulin: mimicking endogenous insulin release. In: Rathbone M, Hadgraft J, Roberts M, et al, eds. Modified Release Drug Delivery, 2e. New York, NY: Informa Healthcare USA, Inc; 2008.
Kieffer et al. "The glucagon-like peptides." Endocrine Reviews 20:876, 1999.
Vilsboll T et al. "Reduced postprandial concentrations of intact biologically active glucagon-like peptide-1 in type 2 diabetic patients." Diabetes 50:609, 2001.
Vilsboll T et al. "Similar elimination rates of glucagon-like peptide-1 in obese type 2 diabetic patients and healthy subjects." J Clin Endocrinol Metab 88:220, 2003.
Volund "Conversion of insulin units to SI units." American Journal of Clinical Nutrition, Nov 1993, 58(5), pp. 714-715.
Wachters-Hagedoorn et al. "The rate of intestinal glucose absorption is correlated with plasma glucose-dependent insulinotropic polypeptide concentrations in healthy men." J Nutr 136:1511, 2006.
Wang et al., Glucagon-like peptide-1 is a physiological incretin in rat. J. Clin. Invest., 95 : 417-421 (1995).
Wang et al., Glucagon-like peptide-1 regulates proliferation and apoptosis via activation of protein kinase B in pancreatic INS-1 beta cells. Diabetologia, 47:478-487, 2004.
Wareham et al., "Fasting Proinsulin Concentrations Predict the Development of Type 2 Diabetes", Diabetes Care, 1999, 22, 262-70.
Warren et al. "Postprandial versus prandial dosing of biphasic insulin aspart in elderly type 2 diabetes patients." Diabetes Res Clin Pract 66:23-29, 2004.
Waterhouse et al., "Comparatie assessment of a new breath-actuated inhaler in patients with reversible airways obstruction", Respiration 59:155-158 (1992).
WebMD (retrieved from http://www.webmd.com/pain-management/tc/pain-management-side-effects-of-pain-medicines on 0/21/12, 4 pages).
Wei et al. "Tissue-specific expression of the human receptor for glucagon-like peptide-1: brain and pancreatic forms have the same deduced amino acid sequence." FEBS Letters 358:219, 1995.
Weir et al. "Glucagonlike peptide 1 (7-37) actions on endocrine pancreas." Diabetes 38:338, 1989.
Weiss, SR et al. "Inhaled insulin provides improved glycemic control in patients with type 2 diabetes mellitus inadequately controlled with oral agents." Arch Intern Med 163:2277-2282, 2003.
Weissberger, "Mannkind: Overlooked Biotech with Excellent Prospects (Part V), "http://www.investorvillage.com/smbd.asp?mb=2885&mn=45817&pt=msg&mid=5021385 (posted on Jun. 19, 2008, accessed on Oct. 18, 2012).
West, Solid State Chemistry and its Applications. Wiley, New York, 358 (1998).

Wettergren A et al. "Truncated GLP-1 (proglucagon 78-107-Amide) inhibits gastric and pancreatic functions in man." Digestive Diseases and Sciences 38:665, 1993.
White JR et al. "Inhaled insulin: an overview." Clinical Diabetes 19:13-16, 2001.
Wigley et al., Insulin across respiratory mucosae by aerosol delivery. Diabetes 20(8): 552-556 (1971).
Willms B et al. "Gastric emptying, glucose responses, and insulin secretion after a liquid test meal: effects of exogenous glucagon-like peptide-1 (GLP-1)-(7-36) amide in type 2 (noninsulin-dependent) diabetic patients." J. Clin Endocrinol Metab 81:327, 1996.
Wilson BR et al. "Technospheres(TM) for pulmonary and nasal applications." Respiratory Drug Delivery VIII, 2002, p. 545.
Wilson et al., Spray-drying, a viable technosphere formulation process option to lyophilization, http://www.aapsj.org/abstracts/AM_2004/AAPS2004-002724.PDF, 1 page, 2004.
Witchert, Low molecular weight PLA: A suitable polymer for pulmonary administered microparticles. J. Microencapsulation, 10(2): 195-207 (1993).
Wong et al. "From cradle to grave: pancreatic b-cell mass and glucagon-like peptide-1." Minerva Endocrinologica 31:107, 2006.
Wuts et al. "The Role of Protective Groups in Organic Synthesis," John Wiley, New York, 2nd Ed. 1991.
Yan et al., Analgesic action of microinjection of neurokinin A into the lateral reticular nucleus and nucleus raphe magnus in rats. Acta Physiologica Sinica, vol. 48, No. 5, pp. 493-496 (1996)—abstract.
Yang et al., Division and differentiation of natural antibody-producing cells in mouse spleen. PNAS, 104(11): 4542-4546 (2007).
Yoshida et al., Absorption of insulin delivered to rabbit trachea using aerosol dosage form. J. Pharm. Sci. 68(5): 670-671 (1979).
Yoshioka et al., "Serum proinsulin levels at fasting and after oral glucose load in patients with Type 2 (non-insulin dependent) diabetes mellitus", Diabetogia, 1988, 31, 355-60.
Yu W, Marino MT, Cassidy JP, et al. Insulin antibodies associated with Technosphere® insulin. ADA 2010; Abstract 216-OR.
Yusta B et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Zethelius et al., "Proinsulin is an Independent Predictor of Coronary Heart Disease", Circulation 105:2153-2158 (2002).
Zimmerman, K., "Respiratory System: Fats, Function, and Diseases", <www.livescience.com/22616-respiratory-system.html>, copyright 2013, p. 1.
Zisser et al. "In Patients Using Technospere Insulin. Variation in PPG Stayed Within ADA-recommended Targets Despite Large Variations in Glucose Load." Mannkind Corporation (2010), ADA 2010; Poster 554.
Zisser H, Jovanovic L, Markova K, et al. Technosphere® insulin effectively controls postprandial glycemia in patients with type 2 diabetes mellitus. Diabetes Technology and Therapeutics 2012;14:997-1001.
Wasada, Glucagon-like peptide-1 (GLP-1). Nihon Rinsho, vol. 62, No. 6, pp. 1175-1180 (2004) (full Japanese article with English abstract).
"An inhaled insulin formulation (Technosphere Insulin) effectively improves glycaemic control in patients with type 2 diabetes mellitus." Inpharma Weekly, vol. 1522, Jan. 28, 2006, p. 8.
ACTOS Product Insert. Aug. 2008.
Adjusting Mealtime Insulin Doses. BD Diabetes. http://www.bd.com/diabetes/page.aspx?cat=7001&id=7280.
AHREN "GLP-1 and extra-islet effects." Horm. Med Res 36:842, 2004.
Ahren B et al. "Characterization of GLP-1 effects on b-cell function after meal ingestion in humans." Diabetes Care 26:2860, 2003.
Ahren B., Glucagon-like peptide-1 (GLP-1): a gut hormone of potential interest in the treatment of diabetes. BioEssays, V. 20, pp. 642-651 (1998).
Akerlund et al., Diketopiperazine-based polymers from common acids. Journal of Applied Polymer Science (2000), 78(12), 2213-2218.

(56) References Cited

OTHER PUBLICATIONS

Alabraba et al. Diabetes Technology & Therapeutics. Jul. 2009, 11(7): 427-430.
Alcohols limited. Alcohol speciality solvents-Go green! Jul. 24, 2010. Available from: <http://webarchive.org/web/20100724193725/http://www.alcohols.co.uk/speciality_solvents.php>.
Aljada et al. "Insulin inhibits the pro-inflammatroy transcription factor early growth response gene-1 (Egr)-1 expression in mononuclear cells (MNC) and reduces plasma tissue factor (TF) and plasminogen activator inhibitor-1 (PAI-1) concentrations." The Journal of Clinical Endocrinology and Metabolism, vol. 87, No. 3, p. 1419-1422, 2002.
Al-Showair et al., Can all patients with COPD use the correct inhalation flow with all inhalers and does training help? Respiratory Medicine, vol. 101, No. 11, p. 2395-2401 (2007).
American Diabetes Association, "Standards of medical care in diabetes—2009", Diabetes Care, Jan. 2009, 32 Suppl 1: S13-61.
Amin N, Boss AH, Petrucci R, et al. Pulmonary functions (over 2 years) in diabetic subjects treated with AFRESA® or usual antidiabetic treatment ADA 2009; Poster 570.
Amin N, et al. Long-term sustained safety and efficacy of continued use of Technosphere insulin in subjects with type 2 diabetes. Abstract—Oral Presentation 215, 48th EASD Annual Meeting, Sep. 29-Oct. 2, 2009, Vienna, Austria.
Amin N, Marino MT, Cassidy JP, et al. Acute pulmonary effects of Technosphere® insulin inhalation powder administered using a Gen2B inhaler compared to MedTone® C inhaler. Diabetes Technology Meeting 2010; poster.
Amin N, Phillips M, Boss AH, et al. Pulmonary functions (over 2 years) in diabetic patients treated with Technosphere® insulin (TI) or usual antidiabetic treatment. Third International Conference on Advanced Technologies and Treatments for Diabetes. 2010; Poster 290.
Angelo et al., Technosphere Insulin: Defining the Role of Technosphere Particles at the Celluar Level. J. Diabetes Sci. Technol., vol. 3, Issue 3, pp. 545-554 (2009).
Angelo et al. Technosphere® insulin inhalation powder: Defining the mechanism of action. ADA 2008; 57: Poster 428-P.
Antosiewiez et al., Prediction of pH-dependent properties of proteins. J Mol. Biol., 238:415-436 (1994).
Arakawa et al., Preferential interactions determine protein solubility in three-component solutions: the MgCl2 system. Biochemistry, 29:1914-1923 (1990).
Ashwell et al. "Twice-daily compared with once-daily insulin glargine in people with Type 1 diabetes using meal-time insulin aspart." 2006 Diabetes UK, Diabetic Medicine, 23, 879-886.
Ashwell et al., "Optimal timing of injection of once-daily insulin gargine in people with Type 1 diabetes using insulin lispro at mealtimes" 2005 Diabetes UK, Diabetic Medicine, 23, 46-52.
Atherton, F. et al. "Synthesis of 2(R)-A3(S)-Acylamino-2-OXO-1-Azetidinyloxy U-Acetic Acids." Tetrahedron, vol. 40, No. 6, Jan. 1, 1984, pp. 1033-1046.
Avandia Product Insert, Oct. 2008.
Baggio et al. "A recombinant human glucagon-like peptide (GLP)-1-albumin protein (Albugon) mimics peptidergic activation of GLP-1 receptor-dependent pathways coupled with satiety, gastrointestinal motility, and glucose homeostatsis." Diabetes 53:2492, 2004.
Baggio et al. "Glucagon-like peptide-1, but not glucose-dependent insulinotropic peptide, regulates fasting glycemia and noneneteral glucose clearance in mice." Endocrinology 141:3703, 2000.
Baggio et al. "Harnessing the therapeutic potential of glucagon-like peptide-1." Treat Endocrinol 1:117, 2002.
Balkan B et al. "Portal GLP-1 administration in rats augments the insulin response to glucose via neuronal mechanisms." Am J. Physiol Regulatory Integrative Comp Physiol 279:R1449, 2000.
Barnett AH et al. "An open, randomized, parallel-group study to compare the efficacy and safety profile of inhaled human insulin (Exubera) with glibenclamide as adjunctive therapy in patients with Type 2 diabetes poorly controlled on metformin." Diabetes Care 29(8):1818-1825, 2006.
Barnett et al., An open, randomized, parallel-group study to compare the efficacy and safety profile of inhaled human insulin (Exubera) with metformin as adjunctive therapy in patients with type 2 diabetes poorly controlled on a sulfonylurea. Diabetes Care, 29(6): 1282-1287 (2006).
Barragan et al. "Changes in arterial blood pressure and heart rate induced by glucagon-like peptide-1-(7-36) amide in rats." Am J. Physiol 266 (Endocrinol Metab 29):E459, 1994.
Basu A et al. "Effects of a change in the pattern of insulin delivery on carbohydrate tolerance in diabetic and nondiabetic humans in the presence of differing degrees of insulin resistance." J Clin Invest 97:2351-2361, 1996.
Bauer et al., "Assessment o beta-adrenergic receptor blockade after isamoitane, a 5-HT1-receptor active compound, in healthy volunteer", Clin. Pharmacol Ther 53:76-83 (1993).
Bauer et al., "Pharmacodynamic effects of inhaled dry powder formulations of fenterol and colforsin in asthma", Clin Pharmacol Ther 53:76-83, 1993.
Baughman R, Cassidy J, Amin N, et al. A phase I, open-label study of the effect of albuterol or fluticasone on the pharmacokinetics of inhaled Technosphere® insulin inhalation powder in healthy subjects. ADA 2010; Poster 528.
Baughman R, Cassidy J, Levy B, et al. Technosphere® insulin inhalation powder pharmacokinetics unchanged in subjects who smoke. Diabetes 2008; 57: A128.
Baughman R, Haworth P, Litwin J, et al. No cardiac effects found with therapeutic and suprtherapeutic doses of Technosphere® inhalation powder: results from a thorough QTc clinical study. ADA 2011. Poster 933-P.
Baughman, RA, Evans, SH, Boss, AH, et al. Technosphere insulin does not affect pulmonary function in a 6 month study of patients with type 2 diabetes. Diabetologia 2006;49:177-118.
Bayés M et al. "Gateways to clinical trials" Methods Find Exp Clin Pharmacol 24:431-455, 2002.
Beers et al., Section 2—Chapter 13—Diabetes Mellitus, The Merck Manual of Diagnosis and Therapy, Merck Research Laboratories, pp. 165-177 (1999).
Behme et al. "Glucagon-like peptide-1 improved glycemic control in type 1 diabetes." BMC Endocrine Disorders 3:3, 2003.
Bellary et al. "Inhaled insulin:new technology, new possibilities." Int J Clin Pract 60:728, 2006.
Belmin J et al. "Novel drug delivery systems for insulin. Clinical potential for use in the elderly." Drugs Aging 20:303-12, 2003.
Benita, Charaterization of Drug-Loaded Poly(d,l-lactide) Microspheres. J. Pharm. Sci., 73: 1721-1724 (1984).
Benito E et al. "Glucagon-like peptide-1-(7-36) amide increases pulmonary surfactant secretion through a cyclic adenosine 3',5'-monophosphate-dependent protein kinase mechanism in rat type II pneumocytes." Endocrinology 139:2363, 1998.
Bensch et al., Absorption of intact protein molecules across the pulmonary air-tissue barrier, Science 156: 1204-1206 (1967).
Berge et al., "Pharmaceutical Salts", J. Pharmaceutical Sciences, Review Article, 66(1):1-19 (1977).
Bergenstal R, Kapsner P, Rendell M, et al., Comparative efficacy and safety of AFRESA® and a rapid-acting analog both given with glargine in subjects with T1 DM in a 52-week study ADA 2009; Poster 479.
Bergeron et al. "Macromolecular Self-Assembly of Diketopiperazine Tetrapeptides." J. Am. Chem. Soc. 116, 8479-8484, 1994.
Nathan DM et al. "Management of hyperglycemia in Type 2 diabetes: a consensus algorithm for the initiation and adjustment of therapy." Diabetes Care 29:1963, 2006.
Nathan DM et al. "Management of hyperglycemia in Type 2 diabetes: a consensus algorithm for the initiation and adjustment of therapy." Diabetes Care 31:173, 2008.
Nathan DM et al. "Management of hyperglycemia in Type 2 diabetes: a consensus algorithm for the initiation and adjustment of therapy." Diabetes Care 32:193, 2009.

(56) References Cited

OTHER PUBLICATIONS

Nathan et al. "Intensive diabetes treatment and cardiovascular disease in patients with Type 1 diabetes." New Eng. J. Med. 353:2643-2653, 2005.
Nathan, "Initial Management of Glycemia in Type 2 Diabetes Mellitus" N. Eng. J. Med., 2002, 347, 1342-9.
Nauck "Is glucagon-like peptide 1 an incretin hormone?" Diabetologia 42:373, 1999.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck et al. "Reduced incretin effect in type 2 (non-insulin-dependent) diabetes." Diabetologia 29:46, 1986.
Nauck et al., Effects of glucagon-like peptide 1 on counterregulatory hormone responses, cognitive functions, and insulin secretion during hyperinsulinemic, stepped hypoglycemic clamp experiments in healthy volunteers. J Clin Endocrinol Metab., 87:1239-1246, 2002.
Nauck et al., Effects of subcutaneous glucagon-like peptide 1 (GLP-1 [7-36 amide]) in patients with NIDDM. Diabetologia, 39:1546-1553, 1996.
Nauck et al., Normalization of fasting hyperglycemia by exogenous GLP-1 (7-36 amide) in type 2 diabetic patients. Diabetologia, 36:741-744, 1993.
NHS Clinical Guidelines, "Type 1 diabetes diagnosis and mangement of type 1 diabetes in children and young people", National Collaborating Centre for Women's and Children's Health Commissioned by the National Institute for Clinical Excellence, Sep. 2004, p. 1-217.
Non-covalent interactions from UC Davis ChemWiki, pp. 1-5. Accessed by Examiner on Jul. 23, 2013 and related case U.S. Appl. No. 12/830,557.
Nystrom et al. "Effects of glucagon-like peptide-1 on endothelial function in type 2 diabetic patients with stable coronary artery disease." Am J Physiol Endocrinol Metabl 287:E1209, 2004.
Okumura et al., Intratracheal delivery of insulin: absorption from solution and aerosol by rat lung. Int. J. Pharmaceuticals 88: 63-73 (1992).
Orgsoltab et al., Division of Organic Chemistry. Ohio Northern University. Nov. 24, 2009. Available from: <http://www.2.onu.edu/~b-meyers/organic_solvents.html>.
Oshima et al. "Comparison of half-disappearance times, distribution volumes and metabolic clearance rates of exogenous glucagon-like peptide 1 and glucagon in rats." Regulatory Peptides 21:85, 1988.
Ostrovsky, Gene. Mannkind Inhalation Insulin Going to FDA to Seek Approval [on-line]. MedGadget.com, posted on Mar. 17, 2009, Retrieved from the Internet: <URL:http://medgadget.com/2009/03mannkind_inhalation_insulin_going_to_fda_to_seek_approval.html>.
Owens et al. "Inhaled human insulin." Nature Reviews, Drug Discovery, vol. 5, No. 5, pp. 371-372, May 2006.
Owens et al. "Alternative routes of insulin delivery." Diabetic Medicine 20:886-898, 2003.
Ozyazgan et al. "Effect of glucagon-like peptide-1)7-36) and exendin-4 on the vascular reactivity in streptozotocin/nicotinamide-induced diabetic rats." Pharmacology 74:119, 2005.
Pacini P, Marino MT. Evaluation of endogenous and exogenous components to peripheral insulin concentration during administration of inhaled insulin. ADA 2010; Abstract 2094-PO.
Patton "Mechanisms of macromolecule absorption by the lungs." Advanced Drug Delivery Reviews 19:3, 1996.
Patton "Unlocking the opportunity of tight glycaemic control. Innovative delivery of insulin via the lung." Diabetes Obesity and Metabolism 7:S5, 2005.
Patton & Platz, Routes of Delivery: Case studies: pulmonary delivery of peptides and proteins for systemic action. Adv. Drug. Del. Rev. 8: 179-196 (1992).
Patton et al. "The lungs as a portal of entry for systemic drug delivery." Proc Am Thorac Soc 1:338, 2004.
Patton et al. "Clinical pharmacokinetics and pharmacodynamics of inhaled insulin." Clin Pharmacokinet 43:781-801, 2004.
Patton et al., "Inhaled Insulin", Advanced Drug Delivery Reviews, 35, Feb. 1999, p. 235-247.
Pearson et al., Systematically Initiating Insulin, supplemental to vol. 32, No. 1, 19S-28S, 2006.
Perera et al. "Absorption and Metabolic Effect of Inhaled Insulin." Diabetes Care, vol. 25, No. 12, Dec. 2002, p. 2276-2281.
Petkowicz et al., "Hypoglycemic effect of liposome-entrapped insulin adminstered by various routes into normal rats", Pol. J. Pharmacol. Pharm. 41:299-304 (1989).
Petrucci R, Amin N, Lovertin P. et al. Pulmonary function tests remain similar in patients who received Technosphere® insulin and in patients currently receiving standard antidiabetic therapy. Diabetologia 2009; 52 (suppl 1).
Peyrot et al. "Resistance to insulin therapy among patients and providers." Diabetes Care 28:2673-2679, 2005.
Peyrot M, Rubin RR, Otterbach K. Effect of Technosphere® inhaled insulin on treatment satisfaction, glycemic control and quality of life. Diabetes 2006; 55:Abstract 423-P.
Pezron et al., Insulin aggregation and asymmetric transport across human bronchial epithelial cell monolayers (Calu-3). J. Pharmaceutical Sci. 91: 1135-1146 (2002).
Pfeiffer MA et al. Insulin secretion in diabetes mellitus. Am J Med 70:579-88, 1981.
Pfutzner et al., Abstract 812: Influence of small dose i.v.s.c. and pulmonary insulin treatment on grandial glucose control in patients with type 2 diabetes. Internet Article [Online] 2001, 37th Annual Meeting of the EASD, Glasgow, Sep. 9-13, 2001.
Pfützner A et al. "Pulmonary insulin delivery by means of the Technosphere(TM) drug carrier mechanism." Expert Opin Drug Deliv 2:1097-1106, 2005.
Pfützner A et al. "Lung distribution of radiolabeled Technosphere™ /Insulin." Diabetes 52 Supplement, Jun. 2003, A107.
Pfützner A et al. Pilot study with Technosphere/PTH(1-34)—a new approach for effective pulmonary delivery of parathyroid hormone (1-34). Horm Metab Res 35:319-323, 2003.
Pfützner A et al. "Variability of insulin absorption after subcutaneous and pulmonary application in patients with type 2 diabetes." Diabetes 51 Supplement, Jun. 2002, A47-48.
Standl et al. "Good Glycemic Control With Flexibility in Timing of Basal Insulin Supply." Diabetes Care, vol. 28, No. 2, Feb. 2005.
Stanley et al. "Gastrointestinal satiety signals III. Glucagon-like peptide 1, oxyntomodulin, peptide YY and pacretic peptide." Am J Physiol Gastrointest Liver Physiol 286:G693, 2004.
Steinberg et al. "A new approach to the safety assessment of pharmaceutical excipients." Reg Toxicol Pharmacol 24:149, 1996.
Steiner et al. "A novel glucagon delivery system for the management of hyperinsulinemia." Diabetes 49 Supplement 1, Abstract 1545-PO, A368, 2000.
Steiner et al. "Bioavailability and pharmacokinetic properties of inhaled dry powder Technosphere® /Insulin." Diabetes 49 Supplement, May 2000, A126.
Steiner et al. "Technosphere®, a novel drug delivery system for oral administration of calcitonin." Pharmaceutical Res 11:S299, 1994.
Steiner et al. Technosphere(TM)/Insulin—proof of concept study with a new insulin formulation for pulmonary delivery. Exp Clin Endocrinol Diabetes, 110:17-21, 2002.
Steiner, K. et al. "The relative importance of first- and second-phase insulin secretion in countering the action of glucagon on glucose turnover in the conscious dog." Diabetes 31:964-972, 1982.
Steiner S, Rave K, Heise T, et al. Pharmacokinetic properties and bioavailablility of inhaled drug powder Technosphere™ /insulin. Exp Clin Endocrinol Diabetes 2000; 108:S161.
Steiner S, Rave K, Heise T, et al. Technosphere™ /insulin: Bioavailability and pharmacokinetic properties in healthy volunteers. Diabetologia 2000;43:Abstract 511-P.
Steiner SS, Burrell BB, Feldstein R, et Al. Pulmonary delivery of Technosphere™ /insulin: Increased bioefficacy and bioavailability in clinical trials using the PDC Medtone™ inhaler. Proceed Int'l Symp Control Rel Bioact Mater 2000; 27: 1000-1001.
Stowell et al. "Development of GLP-1 Technosphere(TM) powder: an inhaled GLP-1 product" Diabetes Technology Meeting, San Francisco, Oct. 2007.

(56) References Cited

OTHER PUBLICATIONS

Strack "Inhaled Human Insulin." Drugs of Today 2006, 42 (4): 207-221.
Sturis et al., GLP-1 deriative liraglutide in rats with beta-cell deficiences: influence of metabolic state on beta-cell mass dynamics. British Journal of Pharmacology, 140 : 123-132 (2003).
Sympatecs. Dry Dispersion for Laser Diffraction and Image Analysis, 2011. XP-002586530.
Tack Cees J. et al., Forced Titration to Different Doses of Technosphere Insulin Demonstrates Reduction in Postprandial Glucose Excursions and Hemoglobin A1c in Patients with Type 2 Diabetes. Journal of Diabetes Science and Technology, vol. 2, Issue 1, pp. 47-57, Jan. 2008.
Tack CJ, Boss AH, Baughman RA, et al. A randomized, double blind, placebo controlled study of the forced titration of prandial Technosphere® /Insulin in patients with type 2 diabetes mellitus. Diabetes 2006;55:Abstract 428-P.
Tack CJ, Christov V, deGalan BE, et al. Randomized forced titration to different doses of Technosphere® insulin demonstrates reduction in postprandial glucose excursions and hemoglobin A1c in patients with type 2 diabetes. J Diabetes Sci Technol 2008;2:47-57.
Tang-Christensen et al. "Central administration of GLP-1-(7-36) amide inhibits food and water intake in rats." Am J Physiol 271 (Regulatory Integrative Comp Physiol 40):R848, 1996.
Taylor et al. "Aerosols for macromolecule delivery. Design challenges and solutions." Am J Drug Deliv 2:143-155, 2004.
Teeter et al. "Dissociation of lung function changes with humoral immunity during inhaled human insulin therapy." Am J Resp Crit Care Med 173:1194, 2006.
The American Diabetes Association "Insulin Administration" Diabetes Care, vol. 27, Supplement 1, S106-S109 (2004).
The Decode study group. "Glucose tolerance and mortality: comparison of WHO and American Diabetes Association diagnostic criteria." Lancet. Aug. 21, 1999;354(9179):617-21.
The Lancet. 1989, vol. 333, p. 1235-1236.
Thorens "Expression cloning of the pancreatic b-cell receptor for the gluco-incretin hormone glucagon-like peptide-1." PNAS 89:8641, 1992.
Thorens B et al. "Cloning and function expression of the human islet GLP-1 receptor: demonstration that exendin-4 is an agonist and exendin-(9-39) an antagonist of the receptor." Diabetes 42:1678, 1993.
Todd et al. "Glucagon-like peptide-1 (GLP-1: a trial of treatment in non-insulin-dependent diabetes mellitus." Eur J Clin Invest 27:533, 1997.
Todd et al. Subcutaneous glucagon-like peptide-1 improves postprandial glucaemic control over a 3-week period in patients with early type 2 diabetes. Clinical Science 95:325, 1998.
Toft-Nielson et al. "Determinants of the effectiveness of glucagon-like peptide-1 in type 2 diabetes." J Clin Endocrinol Metab 86:3853, 2001.
Toft-Nielson et al. "Exaggerated secretion of glucagon-like peptide-1 (GLP-1) could cause reactive hypoglcaemia." Diabetologia 41:1180, 1998.
Toft-Nielson et al. "The effect of glucagon-like peptide-1 (GLP-1) on glucose elimination in healthy subjects depends on the pancreatic glucoregulatory hormones." Diabetes 45:552, 1996.
Tornusciolo D.R. et al., Biotechniques 19(5):800-805, 1995. Simultaneous detection of TDT-mediated dUTP-biotin nick end-labeling (TUNEL)-positive cells and multiple immunohistochemical markers in single tissue sections.
Triantafyllidis et al., Structural, compositional and acidic characteristics of nanosized amorphous or partially crystalline ZSM-5 zeolite based materials. Microporous and Mesoporous Materials, 75:89-100 (2004).
Tu N, Kramer DA, Baughman RA. Inhaled Technosphere® Insulin improves glycemic control without weight gain. Diabetes 2007;56:Abstract 471-P.

Tuley et al., Experimental observations of dry powder inhaler dose fluidisation. International Journal of Pharmaceutics, 358, pp. 238-247 (2007).
Utah Valley University. Saponification. © 2009. Available from: <http://science.uvu.edu/ochem/index.php/alphabetical/s-t/saponification/printpage/>.
Vahl et al. "Effects of GLP-1-(7-36)NH2, GLP-1-(7-37), and GLP-1-(9-36)NH2 on intravenous glucose tolerance and glucose-induced insulin secretion in healthy humans." J Clin Endocrinol Metabol 88:1772, 2003.
Van Alfen-Van Der Velden et al. "Successful treatment of severe subcutaneou insulin resistance with inhaled insulin therapy", Pediatric Diabetes 2010: 11:380-382.
Vara E et al. "Glucagon-like peptide-1 (7-36) amide stimulates surfactant secretion in human type II pneumocytes." Am J Resp Crit Care Med 163:841, 2001.
Vella A et al. "Effect of glucagon-like peptide 1(7-36) amide on glucose effectiveness and insulin action in people with type 2 diabetes." Diabetes 49:611, 2000.
Vella A et al. "The gastrointestinal tract and glucose tolerance." Curr Opin Clin Nutr Metab Care 7:479, 2004.
Vendrame et al. "Prediabetes: prediction and prevention trials." Endocrinol Metab Clin N Am, 2004, vol. 33, pp. 75-92.
Verdich C, et al., A meta-analysis of the effect of glucagon-like peptide-1 (7-36) amide on ad libitum energy intake in humans. J Clin Endocrinol Metab., 86:4382-4389, 2001.
Vilsboll et al. "Reduced postprandial concentrations of intact biologically active glucagon-like peptide-1 in type 2 diabetic patients." Diabetes 50:609, 2001.
Vilsboll et al. "Similar elimination rates of glucagon-like peptide-1 in obese type 2 diabetic patients and healthy subjects." J Clin Endocrinol Metab 88:220, 2003.
Vilsboll et al., "Evaluation of β-Cell Secretary Capacity Using Glucagon-Like Peptide 1", Diabetes Care, vol. 23, No. 6, pp. 807-812, Jun. 2000.
Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.
Heine "Unlocking the opportunity of tight glycaemic control. Promise ahead: the role of inhaled insulin in clinical practice." Diabetes, Obesity and Metabolism 7:S19, 2005.
Heinemann "Variability of Insulin Absorption and Insulin Action." Diabetes Technology & Therapeutics, vol. 4, No. 5, pp. 673-682. 2002.
Heinemann et al. "Current status of the development of inhaled insulin." Br. J. Diabetes Vasc. Dis. 4:295-301, 2004.
Heinemann L et al. "Time-action profile of inhaled insulin." Diabetic Med 14:63-72, 1997.
Heinemann, L. "Intra-individual Variability of the Metabolic Effect of Inhales Insulin Together with an Absorption Enhancer", Diabetes Care, vol. 23, No. 9, Sep. 2000, p. 1343-1347.
Heise et al. "The effect of insulin antibodies on the metabolic action of inhaled and subcutaneous insulin." Diabetes Care 28:2161, 2005.
Herbst et al., Insulin Strategies for Primary Care Providers. Clinical Diabetes, vol. 20, No. 1, pp. 11-17 (2002).
Heubner et al. "On inhalation of insulin" Klinische Wochenschrift 16:2342, 1924. Both original and translated documents included.
Heyder "Particle Transport onto Human Airway Surfaces", Eur. J. Respir. Dis, Suppl. 119, 29-50 (1982).
Heyder, "Alveolar deposition of inhaled particles in humans", Am. Ind. Hyg. Assoc. J. 43(11): 864-866 (1982).
Hirsch IB "Insulin analogues." N Engl J Med 352:174-83, 2005.
Hirsch, "Type 1 Diabetes Mellitus and the Use of Flexible Insulin Regimens" American Family Phyician, Nov. 15, 1999, p. 1-16.
Hirshberg B et al. "Islet transplantation: where do we stand now?" Diabetes Metab Res Rev 19:175-8, 2003.
Hite et al. "Exhuberance over Exubera." Clin Diabetes 24(3):110-114, 2006.
Hoet et al., Review: Nanoparticles-known and unknown health risks. Journal of Nanobiotechnology, vol. 2, No. 12, (15 pages) (2004).

(56) References Cited

OTHER PUBLICATIONS

Hollander et al. "Efficacy and Safety of Inhaled Insulin (Exubera) Compared with Subcutaneous Insulin Therapy in Patients with Type 2 Diabetes." Diabetes Care, vol. 27, No. 10, Oct. 2004, p. 2356-2362.
Holst "Therapy of type 2 diabetes mellitus based on the actions of glucagon-like peptide-1." Diabetes Metab Res Rev 18:430, 2002.
Holst et al. "On the effects of glucagon-like peptide-1 on blood glucose regulation in normal and diabetic subjects." Ann NY Acad Sci. Dec. 26, 1996;805:729-36.
Howard C, Ren H, Rossiter A, et al. Reduced incidence and frequency of hypoglycemia in an integrated analysis of pooled data from clinical trials of subjects with type 1 diabetes using prandial inhaled Technosphere® insulin. Diabetologia 2009; 52 (suppl 1).
Howard CP, Gnudi L, Lorber D, et al. Prandial inhaled Technosphere® insulin plus insulin glargine vs. biaspart 70/30 insulin in type 2 diabetes inadequately controlled with/without oral agents. Third International Conference on Advanced Technologies and Treatments for Diabetes. 2010; Poster 300.
Howard CP, Lorber D, Ren H, et al. Reduced incidence and frequency of hypoglycemia in pooled data from trials of type 2 diabetics using prandial inhaled Technosphere® insulin. Third International Conference on Advanced Technologies and Treatments for Diabetes 2010; Poster 304.
Howard CP, Petrucci R, Amin N, et al. Pulmonary function test remain similar in patients who received Technosphere® insulin and in patients currently receiving standard antidiabetic therapy. AACE 2010; Poster 267.
Howard CP, Ren H, Rossiter A, Boss AH. Reduced incidence and frequency of hypoglycemia in pooled data from trials of type 1 diabetics using prandial inhaled Technosphere® insulin. Third International Conference on Advanced Technologies and Treatments for Diabetes. 2010; Poster 302.
Howard CP, Ren H, Rossiter A, et al. Reduced incidence and frequency of hypoglycemia in an integrated analysis of pooled data from clinical trials of subjects with type 1 diabetes using prandial inhaled Technosphere® insulin. AACE 2010; Poster 269.
Howard CP, Rubin RR, Peyrot. M. Patient reported outcomes in adults with type 2 diabetes using mealtime Afresa® (inhaled technosphere® insuline) and basal insulin versus premixed insulin ADA 2009; Poster 551.
http://www.bilcaresolutions.com/en/products/pharma-packaging-innovations-pvc-aclar-films <URL:http://web.archive.org/web/20110127102552/http://www.bilcaresolutions.com/en/products/pharma-packaging-innovations-pvc-aclar-films> published on Jan. 27, 2011 as per "Wayback Engine".
http://www.pmpnews.com/article/blister-packaging-materials (May 26, 2009).
Huda et al. "Gut peptides and the regulation of appetite." Obesity Reviews 7:163, 2006.
Hui et al., The short half-life of glucagon-like peptide-1 in plasma does not reflect its long-lasting beneficial effects. European Journal of Endocrinology, 146: 863-869 (2002).
Hussain et al. "State of insulin self-association does not affects its absorption from the pulmonary route." Eur. J. Pharm. Sciences 25:289-298, 2005.
Ikeda, Kuniki et al. "Peptide Antibiotics. XXVI. Syntheses of Cyclodipeptides Containing N. delta.-p-aminobenzenesulfonyl Ornithine Residue." Chemical & Pharmaceutical Bulletin, 20(9), 1849-55, 1972.
Imeryuz et al. "Glucagon-like peptide-1 inhibits gastric emptying via vagal afferent-mediated central mechanisms." Am J Physiol 273 (Gastrointest Liver Physiol 36):G920, 1997.
Insulin is a natural product from http://www.levemir.com/startingoninsulin/whatisinulin.aspx, pp. 1-3. Accessed by Examiner on Apr. 30, 2014 and cited by Examiner in Non-Final Office Action dated May 22, 2014 for U.S. Appl. No. 13/797,657 and cited by Examiner in Non-Final Office Action dated May 22, 2014 for U.S. Appl. No. 12/883,369.
International Search Report for PCT International Application No. PCT/US2010/055323 filed on Nov. 3, 2010.
Written Opinion mailed on Jul. 1, 2013 for International Application No. PCT/US2013/032162 filed on Mar. 15, 2013.
International Search Report mailed on Jun. 21, 2010 for International Application No. PCT/US2010/027038 filed on Mar. 11, 2010.
Written Opinion for International Application No. PCT/US2011/060057 filed on Nov. 9, 2011.
International Search Report mailed Mar. 18, 2013 for International Application No. PCT/US2012/061749 filed on Oct. 24, 2012.
International Search Report mailed on Jun. 20, 2012 for International Applicaion No. PCT/US2012/031695 filed on Mar. 30, 2012.
International Search Report mailed on Nov. 19, 2014 for International Application No. PCT/US2014/049817 filed on Aug. 5, 2014.
International Search Report for International Application No. PCT/US2010/020448 filed on Jan. 8, 2010.
International Search Report mailed on Mar. 11, 2010 for International Application No. PCT/US2009/069745 filed on Dec. 29, 2009.
International Search Report mailed on Oct. 17, 2011 for International Application No. PCT/US2010/026271 filed on Mar. 4, 2010.
International Search Report for International Application No. PCT/US2010/038287 filed on Jun. 11, 2010.
Ishibashi, Norio et al. "Studies on Flavord Peptides. Part V. A Mechanism for Bitter Taste Sensibility in Peptides." Agricultural and Biological Chemistry, 52(3), 819-27, 1988.
Iwanij et al., Characterization of the Glucagon Receptor and its Functional Domains Using Monoclonal Antibodies. The Journal of Biological Chemistry, vol. 265, No. 34, pp. 21302-21308, 1990.
Jain et al. "Insulin Therapy in Type 2 Diabetic Subjects Suppresses Plasminogen Activator Inhibitor (PAI-1) Activity and Proinsulin-like Molecules Independently of Glycaemic Control." Diabetic Medicine, vol. 10, No. 1, p. 27-32, 1993.
Johnson et al., Peptide turn mimetics. Biotechnology and Pharmacy, p. 366-378 (1993).
Bilheimer DW, Ren H, Boss AH. Analysis of cardiovascular adverse events in patients with type 1 or type 2 diabetes enrolled in selected therapeutic trials in the phase 2/3 Technosphere® insulin development program. ADA 2011. Poster 922-P.
Billings CC, Smutney CC, Howard CP, et al. Handleability and characterization of inhalation profiles using the Gen2 delivery system in a pediatric population. Diabetes Technology Meeting 2010; poster.
Biodel's Intellecutal Property position strengthened for ultra-rapid-acting insulin programs by notice of intent to grant from European Patent Office. Newswire Feed, published May 2, 2012.
Blazquez E et al. "Glucagon-like peptide-1 (7-36) amide as a novel neuropeptide." Mol Neurobio 18:157, 1998.
Bloomgarden "Gut-derived incretin hormones and new therapeutic approaches." Diabetes Care 27:2554, 2004.
Boer et al., Design and application of a new modular adapter for laser diffraction characterization of inhalation aerosols. International Jornal of Pharmaceutics 249, pp. 233-245 (2002).
Boer et al., Inhalation characteristics and their effects on in vitro drug delivery from dry powder inhalers. Part 1. Inhalation characteristics, work of breathing and volunteers' preference in dependence of the inhaler resistance. Int. J. Pharm. 130 (1996) 231-244.
Bojanowska "Physiology and pathophysiology of glucagon-like peptide-1 (GLP-1): the role of GLP-1 in the pathogenesis of diabetes mellitus, obesity and stress." Med Sci Monit 11:RA271, 2005.
Bonner-Weir S et al. "New sources of pancreatic beta-cells." Nat Biotechnol 23:857-61, 2005.
Boss AH et al. "Inhaled Technosphere® /Insulin: Glucose elimination at the right time?" Poster presented at the American Diabetes Association 65th Scientific Sessions, Jun. 2005, abstract 443-P.
Boss AH et al. "Insulin bio-effect is limited by speed of absorption and elimination: similarities between an inhaled insulin formulation that mimics first-phase kinetics and i.v. insulin." Diabetologia 47:A314, 2004.
Boss AH et al. "Mimicry of the early phase insulin response in humans with rapidly available inhaled insulin accelerates post prandial glucose disposal compared to slower bioavailable insulin." Presented at the American Diabetes Association 65th Scientific Sessions, Jun. 2005, abstract 1373-P.
Boss AH et al. "Does kinetics matter? Physiological consequences of the ability of Technosphere® /Insulin inhalation to mimic first phase

(56) References Cited

OTHER PUBLICATIONS insulin release." Presented at the 5th Annual Meeting of the Diabetes Technology Society, Nov. 2005, abstract A14.

Boss AH et al. "Markedly reduced post prandial glucose excursions through inhaled Technosphere® /Insulin in comparison to SC injected regular insulin in subjects with type 2 diabetes." 1st Annual Meeting of the European Association for the Study of Diabetes, Sep. 2005, abstract 816.

Boss AH et al. "The variability and time-action profile of inhaled Technosphere® /Insulin compares favorably to that of subcutaneous human regular insulin." Presented at the American Diabetes Association 65th Scientific Sessions, Jun. 2005, abstract 358-OR.

Boss et al. "Prandial Insulin: Is Inhaled Enough?" Drug Development Research 69(3):138-142 (2008).

Boss A H, Petrucci R, Lorber D. Coverage of prandial insulin requirements by means of an ultra-rapid-acting inhaled insulin. Journal of diabetes science and technology 2012;6:773-779.

Boss AH, Baughman RA, Evans SH, et al. A 3 month comparison in type 1 diabetes of inhaled Technosphere® /Insulin (TI) to Sc administered rapid-acting insulin analogue (RAA) as prandial insulin in a basal/prandial regimen. Diabetes 2006; 55:A97.

Boss AH, Evans SH, Firsov I, et al. Technosphere® insulin as effective as sc rapid acting insulin analogue in providing glycemic control in a 6-month study of patients with type 2 diabetes. Diabetes Technology Meeting 2006; poster.

Boss AH, Evans, SH, Ren, H, et al. Superior post prandial glucose control in patients with type 1 diabetes when using prandial technosphere insulin compared to NovoLog. Diabetologia 2006; Abstract 181.

Boss AH, Marino MT, Cassidy JP, et al. C-peptide correction method to determine exogenous insulin levels in pharmacokinetic studies using Technosphere® insulin. Diabetologia 2009; 52 (suppl 1).

Boss AH, Raskin P, Philips M, et al. Glycosylated hemoglobin and hypoglycaemia in patients with Type 2 diabetes mellitus: Technosphere® insulin and usual antihyperglycaemic regimen vs usual antihyperglycaemic regimen. Diabetologia 2010;53(suppl 1).

Brandt D, Boss AH. The next generation insulin therapy. OndrugDelivery 2006 (published online).

Brange et al., "Insulin Structure and Stability", Pharm Biotechnol, 5:315-50 (1993).

Bray "Exanatide" Am J Health-Sys Pharm 63:411, 2006.

Brownlee et al. "Glycemic variability: a hemoglobin A1c-independent risk factor for diabetic complications." JAMA 295:1707, 2006.

Bruce, D.G., et al. "Physiological importance of deficiency of early prandial insulin secretion in non-insulin-dependent diabetes." Diabetes 37:736-44, 1988.

Bullock BP et al. "Tissue distribution of messenger ribonucleic acid encoding the rat glucagon-like peptide-1 receptor." Endocrinology 137:2968, 1996.

Burcelin et al. "Encapsulated, genetically engineered cells, secreting glucagon-like peptide-1 for the treatment of non-insulin-dependent diabetes mellitus." Ann NY Acad Sci. Jun. 18, 1999;875:277-85.

Calles-Escandon, J. and Robbins, D.C. "Loss of early phase insulin release in humans impairs glucose tolerance and blunts thermic effect of glucose." Diabetes 36:1167-72, 1987.

Camilleri et al., The NEJM 356: 820-829.

Campos et al. "Divergent tissue-specific and developmental expression of receptors for glucagon and glucagon0like peptide-1 in the mouse." Endocrinology 134:2156, 1994.

Cassidy J P, Amin N, Marino M, et al. Insulin lung deposition and clearance following Technosphere® insulin inhalation powder administration. Pharmaceutical Research 2011; 28:2157-2164.

Cassidy J, Amin N, Baughman R, et al. Insulin kinetics following Technosphere® insulin inhalation powder administration unchanged in albuterol-treated asthmatics. ADA 2010; Poster 522.

Cassidy J, Baughman RA, Tonelli G, et al. Use of rapid acting insulin analog as the baseline infusion during glucose clamping improves pharmacokinetic evaluation. ADA 2007; 56: Abstract 602-P.

Cassidy JP, Baughman RA, Schwartz SL, et al. AFRESA® (Technosphere® insulin) dosage strengths are interchangeable ADA 2009; Poster 433.

Cassidy JP, Marino MT, Amin N, et al. Lung deposition and absorption of insulin from AFRESA® (Technosphere® insulin) ADA 2009; Poster 425.

Cassidy JP, Potocka E, Baughman RA, et al. Pharmacokinetic characterization of the Technosphere® inhalation platform Diabetes Technology Meeting 2009. poster.

Caumo et al. "First-phase insulin secretion: does it exist in real life" Considerations on shape and function. Am J Physiol Endocrinol Metab 287:E371-E385, 2004.

Cefalu "Concept, Strategies and Feasibility of Noninvasive Insulin Delivery." Diabetes Care 27:239-246, 2004.

Cefalu "Novel routes of insulin delivery for patients with type 1 or type 2 diabetes." Ann Med 33:579-586, 2001.

Cefalu et al., Inhaled human insulin treatment in patients with type 2 diabetes mellitus. Ann. Int. Med., 2001, 134(3): 203-207.

Ceglia et al. "Meta-analysis: efficacy and safety of inhaled insulin therapy in adults with diabetes mellitus." Ann Intern Med 145:665, 2006.

Cerasi, et al. Decreased sensitivity of the pancreatic beta cells to glucose in prediabetic and diabetic subjects. A glucose dose-response study. Diabetes 21(4):224-34, 1972.

Cernea et al. "Dose-response relationship of oral insulin spray in healthy subjects." Diabetes Care 28:1353-1357, 2005.

Cernea et al. "Noninjectable Methods of Insulin Administration." Drugs of Today 2006, 42 (6): 405-424.

Chan et al., "Pharmacological Management of Type 2 Diabetes Mellitus: Rationale for Rational Use of Insulin", Mayo Clin Proc, 2003, 78, 459-466.

Chase et al., "Redefining the clinical remission period in children with type 1 diabetes", Pediatric Diabetes, 2004, 5, 16-19.

Cheatham et al. "Desirable Dynamics & Performance of Inhaled Insulin Compared to Subcutaneous Insulin Given at Mealtime in Type 2 Diabetes: A Report from the Technosphere/Insulin Study Group." Diabetes Technology and Therapeutics, vol. 6, p. 234 (2004).

Cheatham et al. "A novel pulmonary insulin formulation replicates first phase insulin release and reduces s-proinsulin levels." Presented at the American Diabetes Association 64th Scientific Sessions, Jun. 2004, abstract 457-P.

Li et al. "GLP-1; a novel zinc finger protein required in somatic cells of the gonad for germ cell development." Dev Biol 301:106, 2007.

Li, Jun. Chapter 15: Drug Therapy of Metabolic Diseases. Clinical Pharmacotherapy, People's Medical Publishing House, 1st Edition, pp. 333-335 (2007).

Lian et al. "A Self-Complimentary Self-Assembling Microsphere System: Application for Intravenous Delivery of the Antiepilpetic and Neuroprotectant Compound Felbanate." J Pharm Sci 89:867-875, 2000.

Lim, "Microencapsulation of Living Cells and Tissues", J. Pharm. Sci., 70: 351-354 (1981).

Linder et al., Increase in serum insulin levels is correlated with lung distribution after pulmonary delivery of Technosphere/Insulin. Diabetologia, No. 46, A277 (2003).

Liu et al., "Pulmonary delivery of free and liposomal insulin", Pharmaceuticals Res. 10:228-232, 1993.

Lorber D, Howard CP, Ren H, et al. Reduced incidence and frequency of hypoglycemia in an integrated analysis of pooled data from clinical trials of subjects with type 2 diabetes using prandial inhaled Technosphere® insulin. AACE 2010; Poster 270.

Luque et al. "Glucagon-like peptide-1 (GLP-1) and glucose metabolism in human myocytes." J. Endocrinol 173:465, 2002.

Luzi, L. and DeFronzo, R.A. "Effect of loss of first-phase insulin secretion on hepatic glucose production and tissue glucose disposal in humans." Am. J. Physiol. 257 (Endocrinol. Metab. 20):E241-E246, 1989.

Luzio, S.D., et al. "Intravenous insulin simulates early insulin peak and reduces post-prandial hyperglycaemia/hyperinsulinaemia in type 2 (non-insulin-dependent) diabetes mellitus." Diabetes Res. 16:63-67, 1991.

Malhotra et al., Regulatory Peptides, 41:149-56, 1992.

(56) References Cited

OTHER PUBLICATIONS

Mandal "Inhaled insulin for diabetes mellitus." Am J Health Sys Pharm 62:1359-64, 2005.

Mann "Pulmonary insulin—the future of prandial insulin therapy." Presented at the 5th Annual Meeting of the Diabetes Technology Society, Nov. 2005, abstract A94.

Mannkind Corporation "Postprandial hyperglycemia: clinical significance, pathogenesis and treatment." MannKind Corporation Monograph. 2009.

Mannkind Corporation, Pulmonary Delivery: Innovative Technologies Breathing New Life into Inhalable Therapeutics, www.ondrugdelivery.com, 2006.

Mannkind Corporation. Technosphere Technology: A Platform for Inhaled Protein Therapeutics. Pulmonary Delivery, (www.ondrugdelivery.com), pp. 8-11, 2006.

Marino MT, Cassidy JP, Smutney CC, et al. Bioequivalence and dose proportionality of Afrezza® inhalation powder administered using a Gen2 inhaler compared to the MedTone® inhaler. Diabetes Technology Meeting 2010; poster.

Marino MT, Cassidy JP, Smutney CC, et al. Improvement in bioavailability of FDKP with the NexGen2A device: Implications for delivery of pulmonary insulin. Third International Conference on Advanced Technologies and Treatments for Diabetes 2010; Poster 108.

Marino MT, Cassidy JP, Smutney CC, et al. Improvement in bioavailability of FDKP and insulin with the NGDSB device. Third International Conference on Advanced Technologies and Treatments for Diabetes 2010; Poster 107.

Marino MT. A pharmacokinetic/pharmacodynamic model of inhaled insulin with application to clinical trial simulation. ADA 2010; Abstract 2105-PO.

Marino MT. Cassidy JP, Baughman RA, et al. C-peptide correction method to determine exogenous insulin levels in pk studies using AFRESA® (Technosphere® insulin [TI]) ADA 2009; Poster 1451.

Marshall "Preventing and detecting complications of diabetes." BMJ 333:455, 2006.

Mastrandrea "A breath of life for inhaled insulin: severe subcutaneous insulin resistance as an indication." Pediatric Diabetes 2010: 11: 377-379.

Mathiowitz, Morphology of Polyanhydride Microsphere Delivery Systems, Scanning Microscopy, 4: 329-340 (1990).

Mathiowitz, Novel microcapsules for delivery systems. Reactive Polymers, 6: 275-283 (1987).

Mathiowitz, Polyanhydride microspheres as drug carriers I, hot-melt microencapsulation. J. Controlled Medicine, 5: 13-22 (1987).

Mathiowitz, Polyanhydride microspheres as drug carriers II, microencapsulation by solvent removal. J. Appl. Polymer Sci., 35: 755-774 (1988).

Mathiowitz, Polyanhydride microspheres IV, morphology and characterization systems made by spray drying. J. App. Polymer Sci., 45: 125-134 (1992).

Matsui et al. "Hyperplasia of type II pheumocytes in pulmonary lymphangioleiomyomatosis. Immunohistochemical and electron microscope study." Arch Pathol Lab Med 124:1642, 2000.

Matthews DR et al. "Homeostasis model assessment: insulin resistance and beta-cell function from fasting plasma glucose and insulin concentrations in man." Diabetologia. Jul. 1985;28(7):412-9.

McElduff A et al. "Influence of acute upper respiratory tract infection on the absorption of inhaled insulin using the AERx(R) insulin diabetes management system." Br J Clin Pharmacol 59:546, 2005.

Mcmahon et al., "Effects of basal insulin supplementation on disposition of mixed meal in obese patients with NIDDM", Diabetes, vol. 38, pp. 291-303 (1989).

Meier et al. "Absence of a memory effect for the insulinotropic action of glucagon-like peptide-1 (GLP-1) in healthy volunteers." Horm Metab Res 35:551, 2003.

Meier et al. "Secretion, degradation, and elimination of glucagon-like peptide-1 and gastric inhibitor polypeptide in patients with chronic renal insufficiency and healthy control subjects." Diabetes 53:654, 2004.

Meier et al. "The glucagon-like peptide-1 metabolite GLP-1-(9-36) amide reduces postprandial glycemia independently of gastric emptying and insulin secretion in humans." Am J Physiol Endocrinol Metab 290:E1118, 2006.

Mendes et al., A non-dimensional functional relationship for the fine particle fraction produced by dry powder inhalers, Aerosol Science 38, pp. 612-624 (2007).

Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.

Merck Manual 17th, Japanese Edition, NIKKEI BP Corp., 1999, p. 167-179.

Mitchell et al. "Intranasal Insulin: PK Profile Designed Specifically for Prandial Treatment of Type 2 Diabetes." Drug Development Research 69(3):143-152 (2008).

Monnier et al. "Activation of oxidative stress by acute glucose fluctuations compared with sustained chronic hyperglycemia in patients with type 2 diabetes." JAMA 295:1681, 2006.

Montrose-Rafizadeh et al., Diabetes, 45(Suppl. 2):152A, 1996.

Moren, Aerosols in Medicine (2nd Ed.), Elsevier, pp. 321-350.

Mudaliar et al., Insulin Therapy in Type 2 Diabetes. Endocrinology and Metabolism Clinics, vol. 30, No. 4, pp. 1-32 (2001).

Nagai et al., "Powder Dosage Form of Insulin for Nasal Administration", J. Control Ref., 1:15-22 (1984).

Narayan et al. "Impact of recent increase in incidence on future diabetes burden." Diabetes Care 29:2114, 2006.

Naslund E et al. "GLP-1 slows solid gastric emptying and inhibits insulin, glucagon, and PYY release in humans." Am J Physiol (Regulatory Integrative Comp Physiol 46):R910, 1999.

Naslund E et al. "Prandial subcutaneous injections of glucagon-like petide-1 cause weight loss in obese human subjects." Br J Nutrition 91:439, 2004.

Marino MT, Cassidy JP, Smutney CC, et al. Improvement in bioavailability of FDKP with the NexGen2A device: Implications for delivery of pulmonary insulin. Diabetes Technology Meeting 2009; poster.

* cited by examiner

INTERACTIVE APPARATUS AND METHOD FOR REAL-TIME PROFILING OF INHALATION EFFORTS

CROSS REFERENCE TO RELATED APPLICATIONS

This application claims the benefit of U.S. provisional patent application No. 61/074,487, filed Jun. 20, 2008 and U.S. provisional patent application No. 61/159,052, filed Mar. 10, 2009, the entire disclosures of which are incorporated herein by reference.

TECHNICAL FIELD

Described herein are interactive apparatus and methods for recording, transferring and displaying key physical measurements based on physiological conditions generated by a subject during an inhalation maneuver in real-time.

BACKGROUND

Inhaler devices for dispensing therapeutic substances via the respiratory tract, in particular, for pulmonary delivery in treating local or systemic diseases are commercially available. For example, nebulizers, devices containing propellants, and dry powder inhalers have been used for the treatment of diseases, such as asthma, respiratory tract infections and systemic disease such as diabetes.

The efficiency of delivering a required dosage of a therapeutic substance to a patient in treating a disease depends on the efficiency of the device, and overall delivery can be enhanced by providing proper feedback mechanisms to a patient during use of the device to teach, for example, proper inhalation techniques to a patient. Improper use of the devices and poor inhalation techniques can lead to lack of efficacy in treating a disease, for example, by administering lower dosages of a therapeutic substance than intended or higher dosages of a therapeutic substance which can be harmful to a patient. To effectively deliver therapeutic substances to the respiratory tract, a patient or user can be trained or coached to use the device in an appropriate manner.

Dry powder inhalers used to deliver medicaments to the lungs contain a dose system of a powder formulation usually either in bulk supply or quantified into individual doses stored in unit dose compartments, like hard gelatin capsules, cartridges, or blister packs. Dosing reproducibility requires that the drug formulation is uniform and that the dose can be delivered to the patient with consistent and reproducible results. Therefore, dosing can be improved by optimizing discharge of a formulation, which is effectuated, for example, by having patients perform proper inhalation maneuvers.

Devices for training patients to properly deliver therapeutic substances by the pulmonary tract are described, for example, in U.S. Pat. No. 5,333,106, which discloses an apparatus for interactive training of a patient in use of an aerosol inhaler, including a feedback display based upon air flow versus volume data using a proper sequence of inhalation steps. U.S. patent application Ser. No. 10/759,859 (Publication No. US 2004/0187869) discloses a training device for medicament inhalers, for example, dry powder inhalers, which is based on measuring pressure differential and displaying a single value corresponding to both inhalation rapidity and inhalation flow rate peak, and includes a dry powder inhaler simulator.

Dry powder inhalers and cartridge systems such as those describe in U.S. Pat. Nos. 7,305,986 and 7,464,706, the disclosures of which are incorporated herein by reference in their entirety for all they teach regarding dry powder inhalers, can generate primary drug particles or suitable inhalation plumes during an inspiratory maneuver by deagglomerating a powder formulation within the inhaler and capsule or cartridge. The benefits of delivering drugs via pulmonary circulation are numerous and, include rapid entry into arterial circulation, avoidance of first pass drug degradation by liver metabolism, ease of use, for example, lack of discomfort compared to other routes of administration such as by injection. These devices have been in use in clinical settings and patients have been properly trained on the use of such inhalers.

There is a need in the art for improvements in design and manufacture of a device for training subjects in proper use of an inhalation system; monitoring patients during use of an inhalation system, and monitoring the performance of an inhalation system, such as presence of leakage or defects. The present disclosure presents apparatus and methods to achieve these goals.

SUMMARY

Described herein apparatus for measuring key inspiratory characteristic parameters during use of an inhalation system. The apparatus and methods for using the apparatus can be useful, for example, in training and/or monitoring a subject requiring the use of an inhaler, for example, a high resistance, dry powder inhaler system for delivery of pharmaceuticals, active ingredients or medicaments to the lungs and pulmonary circulation. Example embodiments of the inhalation systems disclosed herein comprise a display means for visual cues to facilitate training and/or monitoring a subject in achieving an optimal or appropriate inspiratory maneuver for the effective delivery of a therapy via the respiratory system. The systems facilitate the training of subjects for the proper use of an inhalation device in order to achieve a preferred flow profile for that individual so that maximal delivery of a medicament can be attained. The devices and method can also be used to monitor the performance of the inhalation systems, for example, detection of the dose being deliver; quantification of the drug being delivered, duration of discharge of a dose being delivered; number of doses administered to the subject, and to monitor the mechanical integrity of the inhalation system.

In an exemplary embodiment, the apparatus can be made to perform interactively, for example, the apparatus can comprise a wireless communication interface allowing for remote acquisition of data, which can be sent to a computer/microprocessor based-system providing an interactive display of data, storage of data and/or web-based transfer of information. Alternatively, other example embodiments can comprise a wired communication interface.

In one example embodiment, the apparatus or device can be adapted, for example, to a high resistance dry powder inhalation system, such as those described in U.S. Pat. Nos. 7,305,986 and 7,464,706, U.S. patent application Ser. Nos. 12/413,405 and 12/484,125 the disclosures all of which are incorporated herein by reference in their entirety for all they disclose regarding dry powder inhalers. The device can comprise a dry powder inhaler with or without a cartridge containing a pharmaceutical formulation, one or more transducers including, electrical, electronic, electro-mechanical, electromagnetic, photonic or photovoltaic; such as pressure sensors, temperature sensors, sound sensors, and optical sensors; a signal conditioning circuitry and/or software program, a means for electronic signal communication and an output display. In such an example embodiment, the apparatus can be used with an analog or digital sensor, appropriate signal conditioners such as amplification, signal filtering, analog to digital conversion, a microprocessor for onboard processing, a wireless communicator in communication with a remote computer or personal data assistant (PDA) for subsequent signal processing and/or real-time output display. The device can be used to deliver pharmaceutical compositions contained in pre-metered unit dose cartridges containing an active ingredient for delivering to the pulmonary circulation. In alternative example embodiments, the sensing and monitoring device can be adapted onto or within an inhalation system comprising a dry powder inhaler with a cartridge that can be empty, or can contain a dry powder suitable for pulmonary delivery.

Dry powders comprising microparticles suitable for pulmonary delivery are well known in the art including, for example, those disclosed in U.S. Pat. Nos. 6,428,771 and 6,071,497, the disclosures of which are incorporated herein by reference in their entirety for all they disclose regarding microparticles. In respective example embodiments, the dry powders, the active ingredient can be a protein, a peptide, or a polypeptide and combinations thereof, for example, and endocrine hormone such as insulin, glucagon-like peptide-1 (GLP-1), parathyroid hormone or analogs thereof.

In certain embodiments, a dry powder formulation for delivery to the pulmonary circulation comprises an active ingredient or agent, including a peptide, a protein, a hormone, analogs thereof or combinations thereof, wherein the active ingredient is insulin, calcitonin, growth hormone, erythropoietin, granulocyte macrophage colony stimulating factor (GM-CSF), chorionic gonadotropin releasing factor, luteinizing releasing hormone, follicle stimulating hormone (FSH), vasoactive intestinal peptide, parathyroid hormone (including black bear PTH), parathyroid hormone related protein, glucagon-like peptide-1 (GLP-1), exendin, oxyntomodulin, peptide YY, interleukin 2-inducible tyrosine kinase, Bruton's tyrosine kinase (BTK), inositol-requiring kinase 1 (IRE1), or analogs, active fragments, PC-DAC-modified derivatives, or O-glycosylated forms thereof. In particular embodiments, the pharmaceutical composition or dry powder formulation comprises fumaryl diketopiperazine and the active ingredient is one or more selected from insulin, parathyroid hormone 1-34, GLP-1, oxyntomodulin, peptide YY, heparin, PTHrP and analogs thereof.

In one example embodiment described herein are dry powder inhalers comprising: a sensor in communication with the dry powder inhaler, wherein the sensor can detect at least one signal type, including pressure, temperature, and sound signals generated from the dry powder inhalation system and can send signal to at least one device for analysis, storage, printing or display. In such an example embodiment, the sensor is configured within the dry powder inhaler or adaptable to the dry powder inhaler and the sensor can be a microphone.

In an example embodiments, the inhalation systems comprises a dry powder inhaler having high resistance to airflow having a resistance value between about 0.065 ($\sqrt{kPa}$)/liter per minute and about 0.200 ($\sqrt{kPa}$)/liter per minute. High resistance inhalation systems can be provided with the sensing and monitoring apparatus. In one embodiment, the sensor can detect intrinsic characteristic signals generated by the inhalation system in use. In another exemplary embodiment, the sensor is a sound sensor which includes a sound detecting device or a microphone, configured to transmit the sound signal by wire or wireless communication mode to at least one another device in the system. The sensing and monitoring apparatus for dry powder inhalers described herein can further be associated with an analog to digital converter which communicates at least one signal such as a sound signal to a microprocessor configured to analyze and process the signal. In another example embodiment, at least one device is an analog to digital converter.

In one example embodiment, monitoring systems are described for a dry powder inhaler comprising: a monitoring device comprising at least one sensor; an analog to digital converter; a data storage medium, wherein the data storage medium includes a set of machine-readable instructions that are executable by a processing device to implement an algorithm, wherein the algorithm comprises instructions for manipulating the data including the steps of: receiving the data from at least one sensor; filtering the data; transforming the data; analyzing the data; and monitoring a patient using the data.

In an example embodiment wherein at least one sensor is a microphone, the monitoring device is provided any place within the inhaler, for example, within the airflow conduits, within the wall of the inhaler, or outside of the inhaler as a separate piece. In another example embodiment, the monitoring device can also be a detachable device that can be mountable on, or attachable to a dry powder inhaler. In yet another example embodiment, the monitoring device provides a graphical display which is a real-time graphical representation of an inhalation.

In another example embodiment, the sound signal is an amplitude of sound signal, a frequency of sound signal or combinations thereof. In yet other example embodiments, the sensor further measures at least one sound signal at different frequencies. In another example embodiment, the dry powder inhalers further comprise a cartridge and the cartridge can comprise a dry powder for pulmonary delivery. Further still, the dry powder can comprise diketopiperazine microparticles and at least one active ingredient. In still another embodiment, at least one medicament comprises insulin, GLP-1, parathyroid hormone, calcitonin, analogues thereof, or combinations thereof.

In a further embodiment, the sensing and/or monitoring device is configured to detect signals from a dose being delivered. In this embodiment, the sensing and monitoring system can detect movement of powder particles within the inhaler and a cartridge system in use from initiation of powder delivery from the cartridge to the end of delivery of the powder particles, wherein the sensor detects variations in the intrinsic characteristics of inhaler sound and powder particle sound emanating from the inhalation system. Data obtained from the detection recordations can be analyzed and correlated to the amount of dose emitted or delivered out of the inhalation system, the time that elapsed for dose delivery, and the performance of the inhalation system.

In another example embodiment, the sensing and monitoring apparatus can be provided as an adaptable, detachable device such as a jacket or saddle structure to a dry powder inhaler. In this embodiment, the removable device facilitates use of the inhalation system, since the structure or configuration of the dry powder inhaler is not modified. Therefore, the same inhaler can be used without the jacket once the characteristic performance of the inhaler has been determined and the subject can properly use it. In embodiments herein, the sensor such as a small microphone, can be advantageously placed in any area of the jacket, including, for example, embedded in the wall of the jacket or adaptor, or extending from the walls of the jacket. In this embodiment, the sensing and monitoring apparatus offers greater resolution of sound characteristics emanating from the dry powder inhaler and cartridge system in use.

In one example embodiment, methods are described for measuring pressure differential during an inhalation maneuver, the methods comprise: providing an inhaler to a subject wherein the inhaler comprises a sensor configured to detect at least one amplitude of sound signal, at least one frequency of sound signal or combinations thereof generated from the inhaler, having the subject inhale for at least one second; analyzing the at least one amplitude of sound signal, said at least one frequency of sound signal, or combinations thereof using an algorithm provided with a microprocessor in a computer system to generate a data set; and displaying, printing, or storing the data set as a function of time and pressure.

In further embodiments described herein are monitoring systems for a dry powder inhalers comprising: a monitoring device comprising at least one sensor; an analog to digital converter; a data storage medium, the data storage medium including a set of machine-readable instructions that are executable by a processing device to implement an algorithm, the algorithm comprising instructions for manipulating the data including the steps of: receiving the data from the at least one sensor; filtering the data; transforming the data; analyzing the data; and monitoring a patient using the data.

Even further still, in one embodiment described herein are methods for measuring pressure differential during an inhalation maneuver, comprising: providing an inhaler to a subject wherein the inhaler comprises a sensor configured to detect at least one amplitude of sound signal, at least one frequency of sound signal or combinations thereof generated from the inhaler, having the subject inhale for at least one second; analyzing the at least one amplitude of sound signal, the at least one frequency of sound signal, or combinations thereof using an algorithm provided with a computer system to generate a data set; and displaying, printing, or storing the data set as a function of time and pressure.

In other embodiments described herein are interactive dry powder inhalation systems for monitoring an inhalation performed by a user, comprising: a dry powder inhaler comprising a cartridge and having a resistance to flow values between 0.065 ($\sqrt{kPa}$)/liter per minute and 0.200 ($\sqrt{kPa}$)/liter per minute; a transducer configured to detect a signal generated from the inhaler in use, and a display device configured to display in real-time an inhalation maneuver performed by a user. In another embodiment, the transducer senses and measures a pressure differential within the inhaler. Further still, the transducer can be a flow meter configured to sense and measure flow rate through air conduits of the dry powder inhaler. The transducer can be, for example, a microphone configured to sense and measure a sound signal generated from within the inhaler.

In still other embodiments described herein are sensing and monitoring devices for adapting to a dry powder inhaler, comprising: a detachable device structurally configured to adapt to a dry powder inhaler; said detachable device comprising a microphone for detecting sound generated in said dry powder inhaler; and wherein the dry powder inhaler has a resistance to flow value between 0.065 ($\sqrt{kPa}$)/liter per minute and 0.200 ($\sqrt{kPa}$)/liter per minute.

Further, in one embodiment, sensing and monitoring devices are described for a dry powder inhalation system, wherein the dry powder inhalation system comprises a dry powder inhaler and a cartridge and the sensing and monitoring device comprises a microphone configured to detect sound signals generated from a dry powder formulation emitted from the dry powder inhalation system.

DETAILED DESCRIPTION

Disclosed herein are apparatus and/or devices with an interactive system and methods for measuring or monitoring real-time changes in pressure or pressure drop and/or flow from a subject during an inhalation maneuver. The devices can be used for training a subject to maximize efficiency of their respiratory maneuvers in conjunction with an inhalation device, and can also be used for monitoring inspiration during delivery a medicament, to detect proper dose delivery, timing of dose delivery and proper performance of the inhalation system in use. In one example embodiment, the sensing and monitoring apparatus can be applied in conjunction with a high resistance inhaler.

The apparatus comprise a transducer or sensor which can convert at least one measurand, including, pressure, air flow, air volume, humidity, and temperature, to an electrical signal. The device further includes appropriate signal conditioning circuitry, such as signal filtering, amplification and analog to digital conversion, and processing circuitry such as a microprocessor, wired or wireless communication interface and the like to transfer the generated signal in real-time to a receiving computer or personal data assistant (PDA) for display of the signal. In one embodiment, the output display can be and interactive display so that the display device provides a visual aid for teaching a subject to perform repeatable inhalation maneuvers in real-time, thereby facilitating proper inhalation delivery of medicament. In another example embodiment, the data can be stored to be analyzed at a later date.

FIGS. 1 through 4 illustrate an example dry powder inhaler training device. The training devices interactive systems described herein have been adapted to a high resistance dry powder inhaler as disclosed in U.S. Pat. Nos. 7,305,986 and 7,464,706, U.S. patent application Ser. No. 11/934,643 (US 2008/0053437), Ser. No. 11/949,707 (US 2008/0127970), Ser. No. 12/102,625; and other high resistance dry powder inhalers are disclosed in U.S. patent application Ser. Nos. 12/413,405; 12/484,125, the disclosures of which are incorporated herein by reference herein for all they disclose regarding dry powder inhalers.

Figure 1:
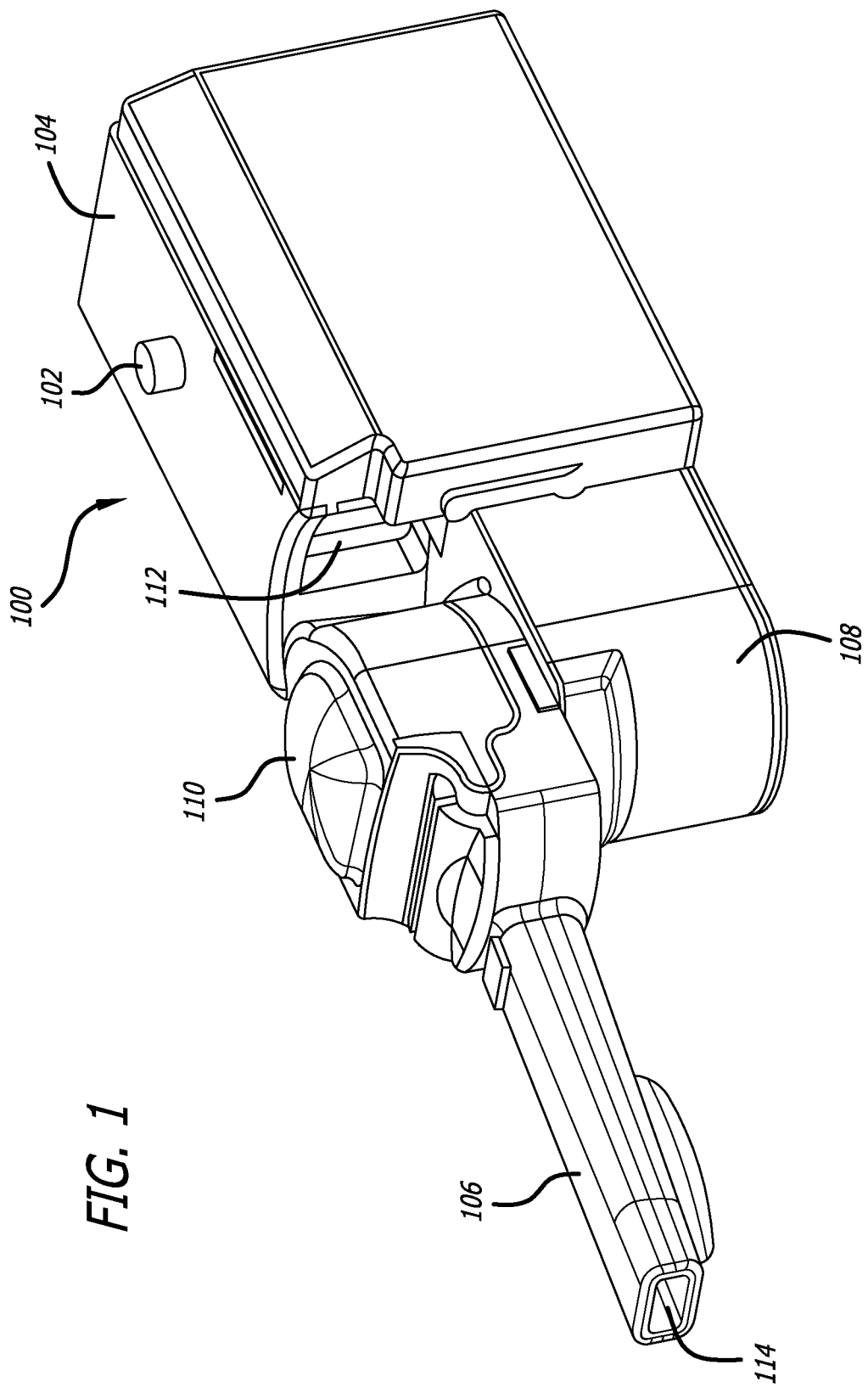
FIG. 1 illustrates an isometric view of the right side of an embodiment of a dry powder inhaler training apparatus.
Figure 2:
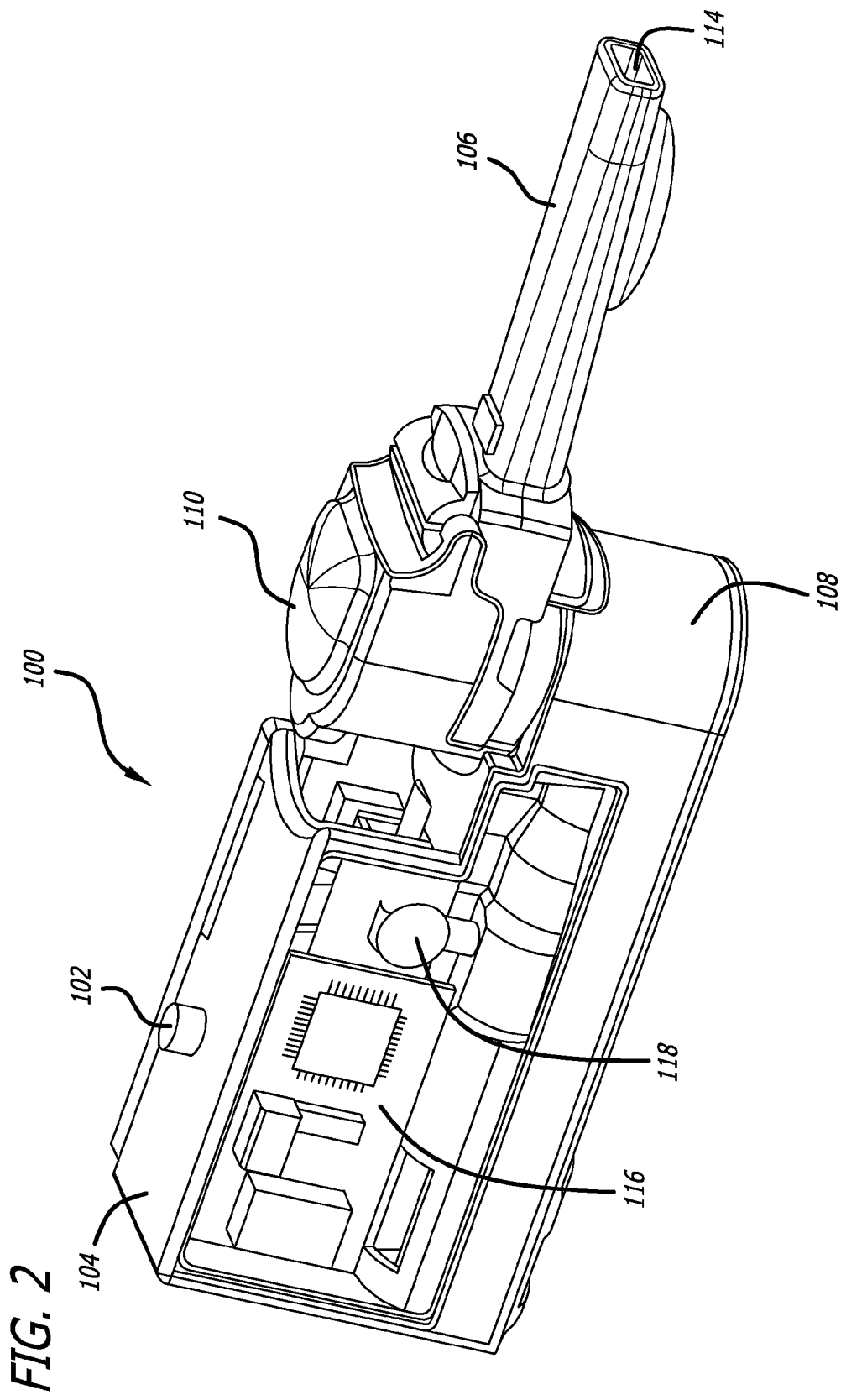
FIG. 2 illustrates an isometric view of the left side of the embodiment of FIG. 1, wherein part of the housing has been removed to show internal component parts of the dry powder inhaler training device.
Figure 3:
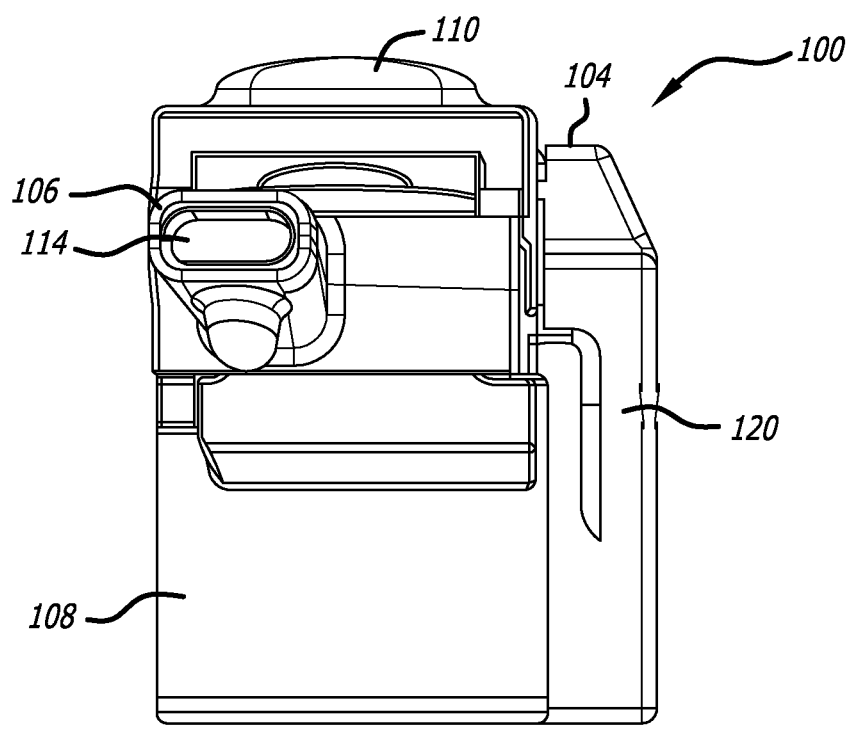
FIG. 3 illustrates a back view of the embodiment of FIG. 1.

Training device 100 comprises activator button 102, housing 104, mouthpiece 106, mixing section 108, a cap or lid 110 over mixing section 108, air inlet port 112 and air outlet port 114. An air conduit is established between air inlet port 112 and air outlet port 114. FIG. 2 illustrates training device 100 with left panel (not shown) of housing 104 removed showing the position of signal processing/interface board 116 and sensor 118 within housing 104. FIG. 3 illustrates a back view of training device 100 showing housing 104 having a compartment with cover 120 on the right side for accommodating a power source.

Figure 4:
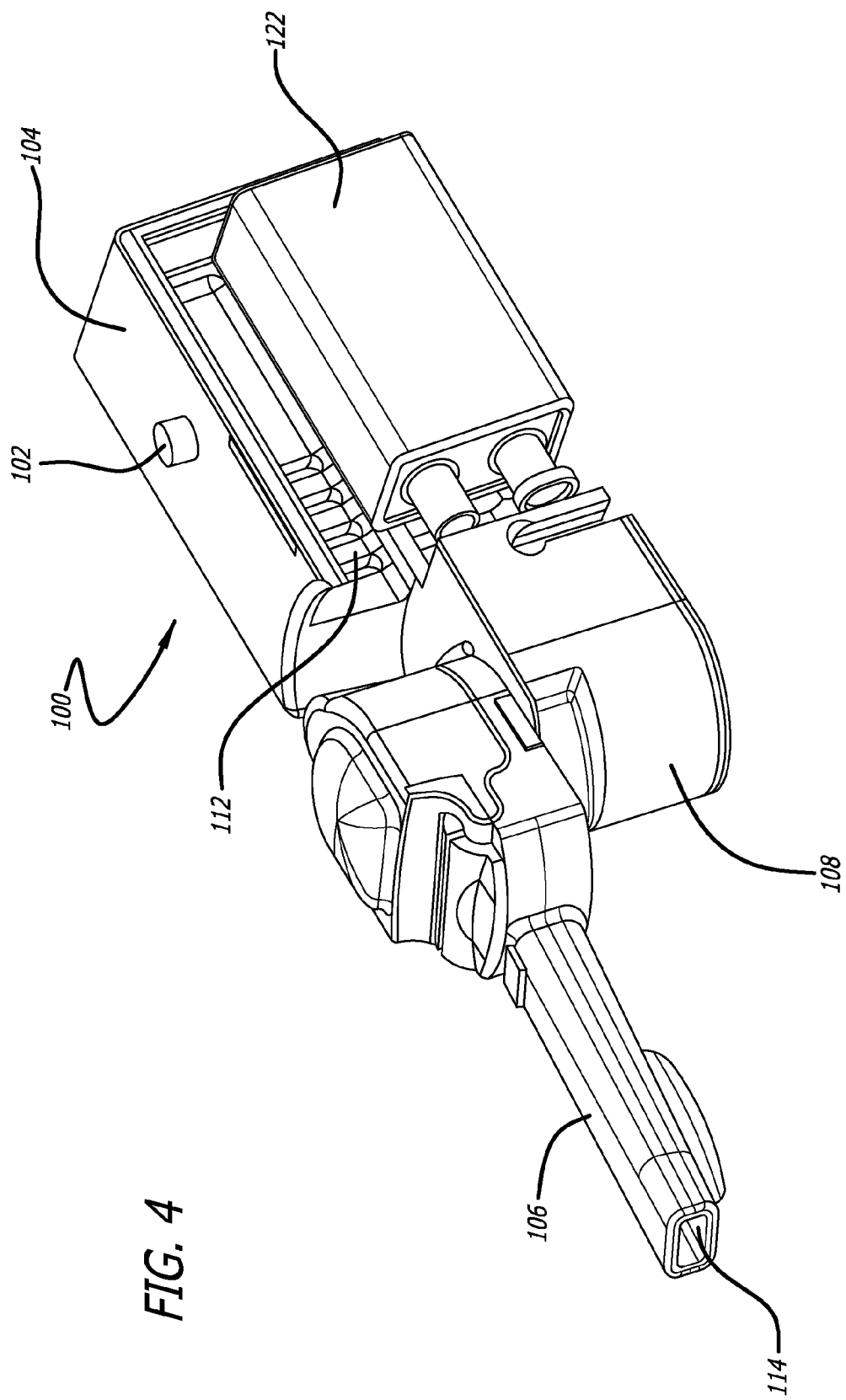
FIG. 4 illustrates an isometric view of the right side of the embodiment of FIG. 1 with the device cover removed to show additional component parts in the interior of the device.

In one example embodiment, sensor 118, in an analogue form, is placed within housing 104 and detects pressure differential from training device 100 when training device 100 is turned on by depressing activator button 102 which is connected to a power source, such battery 122 illustrated in FIG. 4, that also provides power to the system. Sensor 118 can be placed at any point within the air conduit of training device 100. In some example embodiments, sensor 118 can be placed in the air conduit within housing 104. In other example embodiments, sensor 118 can be placed within the mixing chamber (not shown) or the air conduit of mouthpiece 106.

Figure 5:
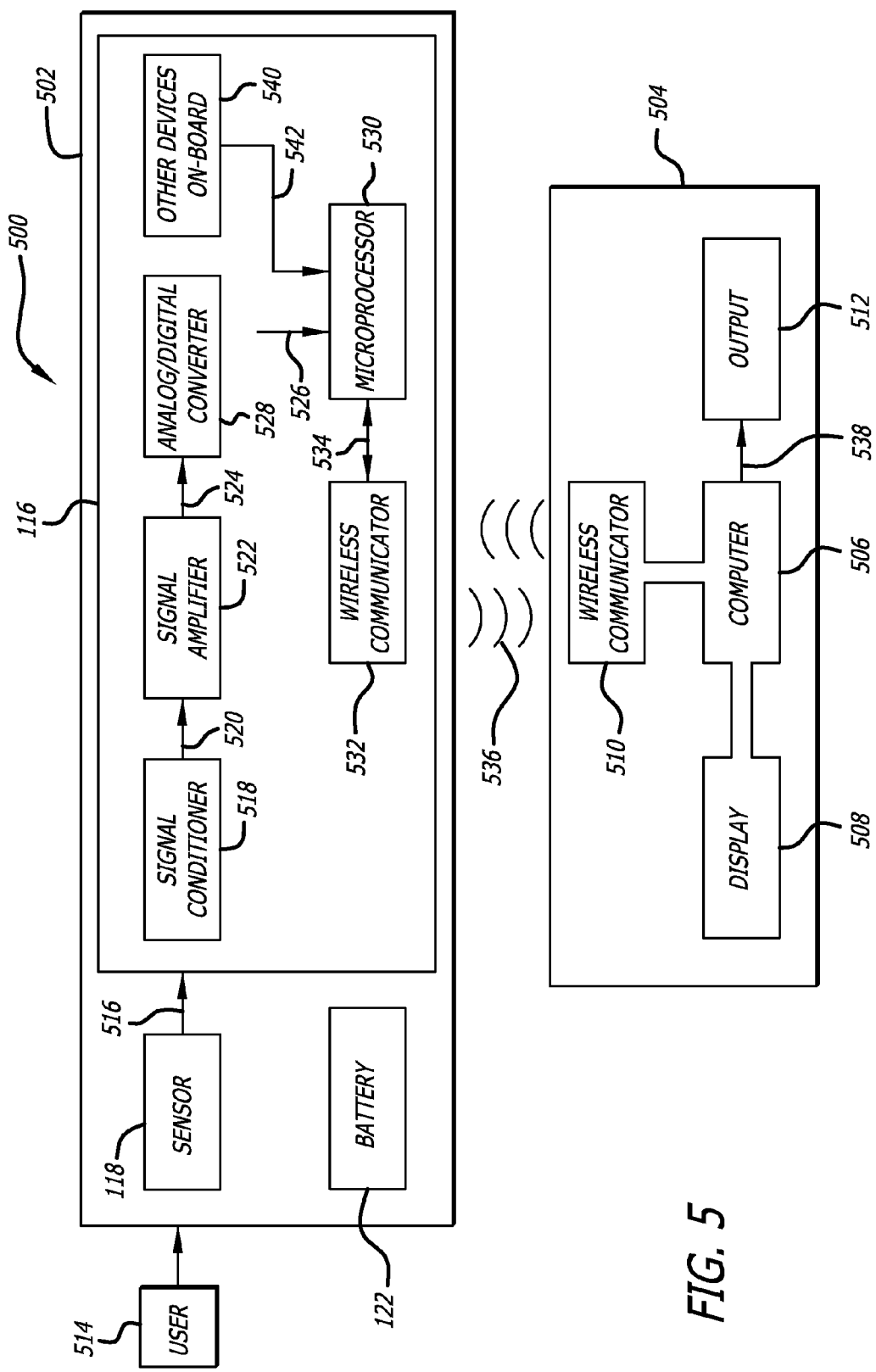
FIG. 5 illustrates a block diagram of the overall training system disclosed herein.

FIG. 5 illustrates a block diagram for an inhaler training device, such as training device 100, showing its various operational component parts. In FIG. 5, system 500 comprises two components, inhaler training device 502 and processing system 504. Processing system 504 can include a PDA or computer 506, display 508, wireless communicator 510 and output 512 which can be in the form of digital storage, a web interface, a print out or the like. In this example embodiment, a user can activate inhaler training device 502 by depressing a power button, for example button 102 on training device 100, with processing system 504 also activated. When the software program integrated with computer 506 is ready, a start signal appears on display 508. With the system activated, inhalation 514 generates a pressure drop in inhaler training device 502 which is transduced to an electrical signal by sensor 118. In this embodiment, the sensor 118 can be a pressure, flow, sound, optical, gas, humidity, or temperature transducer that is either analogue or digital. Electrical signal 516 from sensor 118 is then transmitted to signal conditioner 518 to remove unwanted signals, such as signal noise. Conditioned electrical signal 520 is then transmitted to signal amplifier 522 wherein conditioned electrical signal 518 can be amplified to a predetermined voltage range, and transmitted as amplified signal 524. Amplified signal 524 is then converted to digital signal 526 through analog to digital converter 528. Digital signal 526 then passes through microprocessor 530 and into second wireless communicator 532 through connection 534 for transmission to computer 506, having wireless communicator 510 for receiving wireless signal 536. A software program built into/programmed into microprocessor 530 or computer 506 converts electrical signal 516 to a pressure value which can be displayed graphically. In certain embodiments, a baseline curve for inhaler training device 502 is provided as a reference standard to guide the user's inhalation maneuver. Therefore, during an inhalation, a user can visually compare his/her inhalation maneuver to the baseline standard. In this manner, the user can alter his/her inhalation effort to conform to the requirements of the standard. The displayed data for each inhalation performed by a subject can be saved via second connection 538 to output 512 wherein the data can be stored or transferred accordingly. For example, output 512 can be in the form of a flash drive or printer, or transmitted via email to a physician for review or further training as needed. In one embodiment, signals from the inhalation training device can be transmitted to the computer/PDA and signals from the computer/PDA can be received by the inhalation training device, thereby establishing a two way communication between the two components.

Further, other on-board devices 540 can send and receive data from microprocessor 530 through one or more cable 542. For example, other on-board devices can include digital output sensors, temperature sensors, light emitting diodes (LEDs), sound warning devices, and other on-board sensors.

Other configurations of block diagram 500 can also be configured, for example, following the signal amplification amplified signal 524 can be directly sent to computer 506 via second wireless communicator 532 and the computer can do the analog to digital conversion and other required analysis steps.

Figure 6:
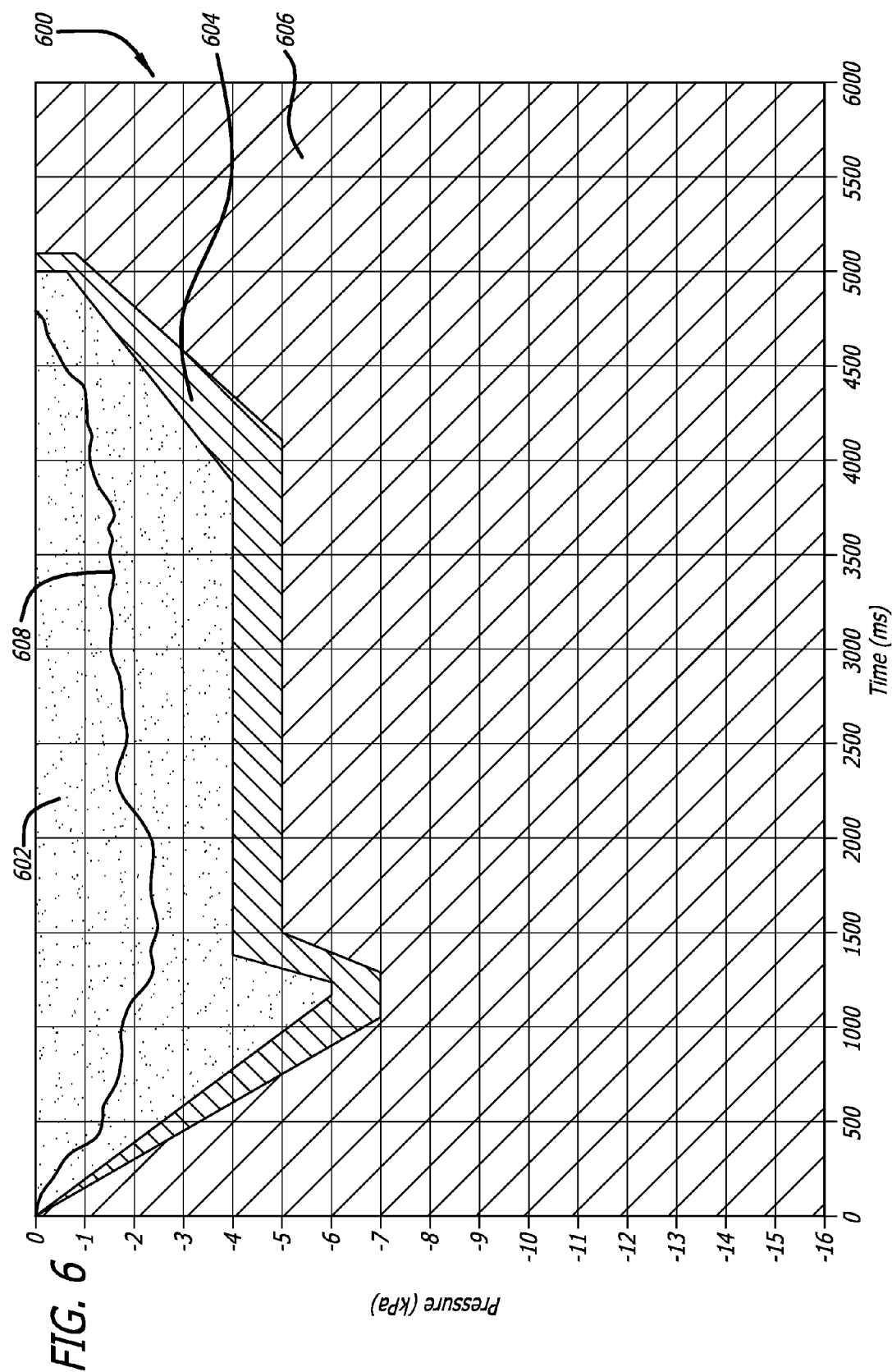
FIG. 6 graphically illustrates an inhalation maneuver performed by a subject without coaching.
Figure 7:
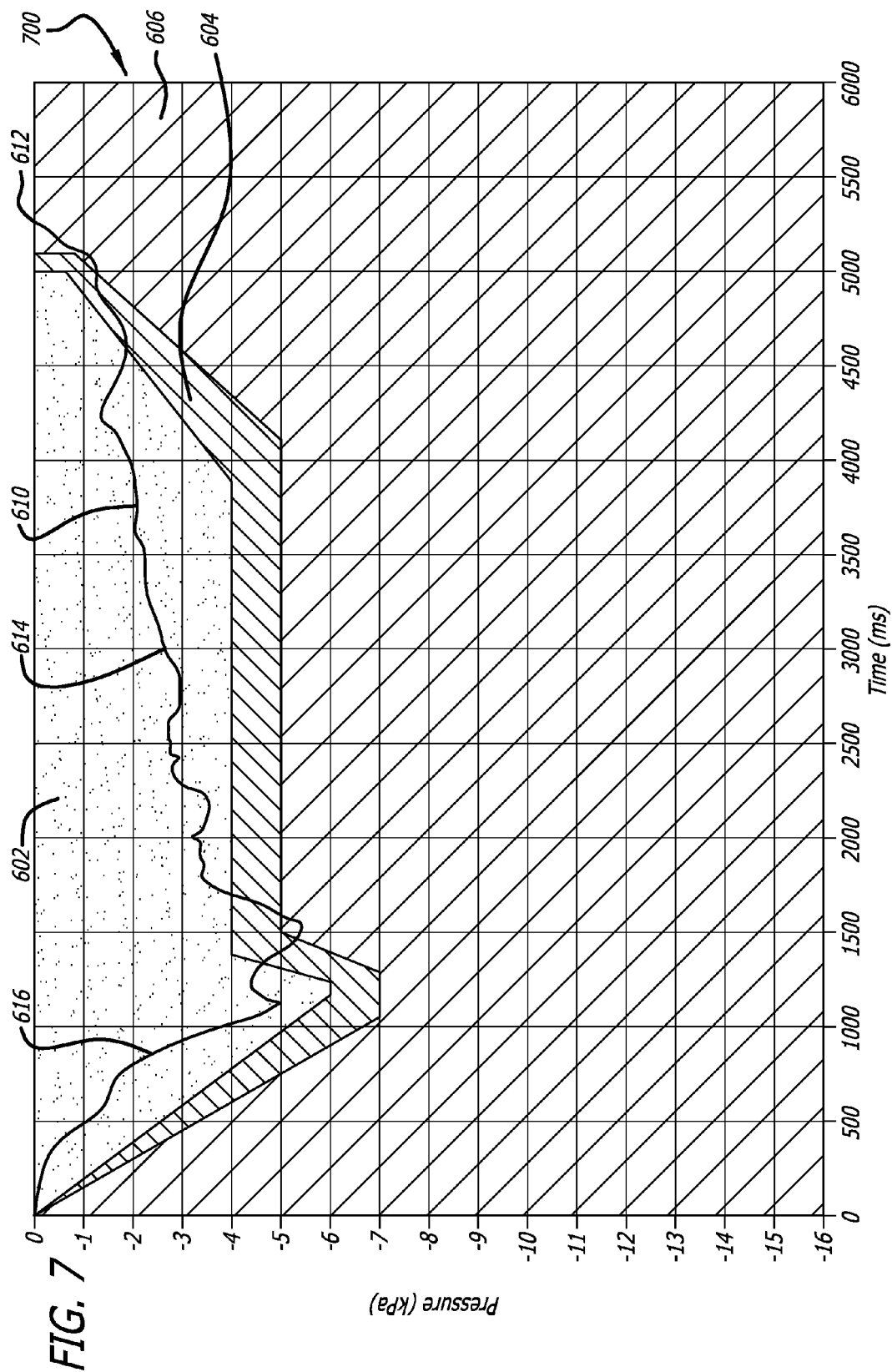
FIG. 7 graphically illustrates an inhalation maneuver performed by a subject only coached to take a deep breath.
Figure 8:
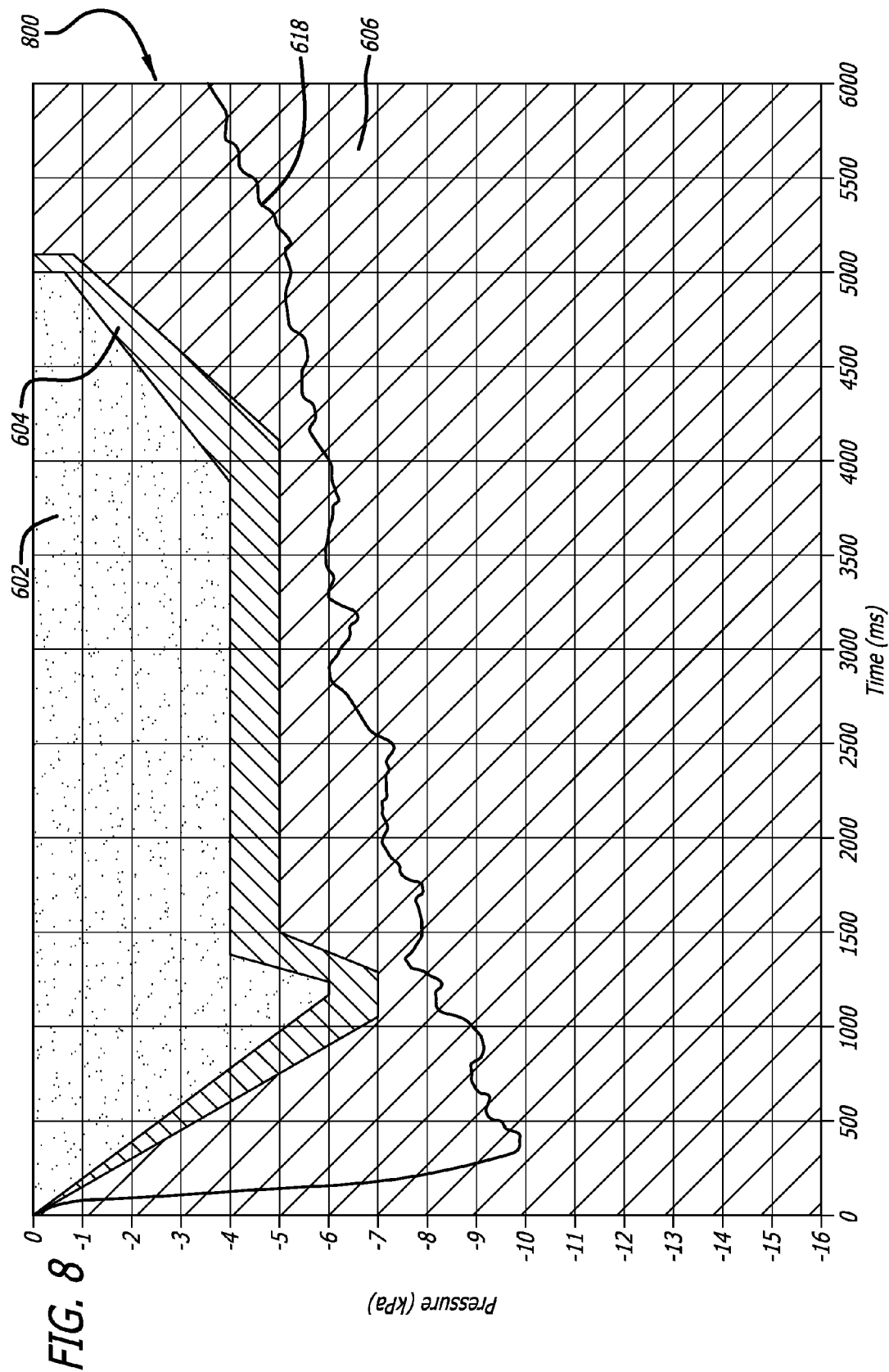
FIG. 8 graphically illustrates an inhalation maneuver performed by a subject properly trained to use a dry powder inhaler using the training device.

Exemplary data from training sessions with a subject are illustrated in FIGS. 6 through 8. Each figure depicts a graph (600, 700, 800) of data displayed by the training systems described herein after an inhalation maneuver. The graphs are plotted as pressure in kPa on the y-axis and time in milliseconds on the x-axis. A baseline inhalation performance standard for training device 100 is shown as region 602 which is bordered by a warning region 604 and an acceptable or preferred region 606. Regions 602, 604 and 606 can be provided in different colors to facilitate discernment of regions in monitoring an individual's performance during an inhalation. Region 602 can be, for example, depicted in red, indicating that the inhalation maneuver did not meet the baseline requirement; therefore, the delivery system would not be optimal to deliver a medicament effectively. Warning region 604 can be depicted in yellow indicating a warning that the inhalation maneuver is nearing the unacceptable performance effort. Preferred region 606 can be depicted in green indicating that the inhalation performance is in the acceptable efforts to effectively deliver a medicament.

FIG. 6 graphically illustrates an example of an inhalation maneuver performed by a subject who has received no training and is not allowed to see the screen display of the computer during the inhalation maneuver. The results of this inhalation are plotted as curve 608. As graphically illustrated in FIG. 6, the inhalation effort by the subject falls in the unacceptable region 602 during the entire inhalation procedure.

FIG. 7 graphically illustrates results of an inhalation maneuver of a subject who has received some guidance on the use of a device and is allowed to look at a computer screen displaying the inhalation effort during the maneuver. In this maneuver and as shown by curve 610, the subject inhaled for an acceptable period of time, as indicated by end point 612 falling within preferred region 606, but did not inhale quickly enough or with enough effort to attain acceptable values, as indicated by regions 614 and 616 which fall within region 602.

FIG. 8 graphically illustrates an example of an inhalation maneuver performed by a subject who has received complete training and is allowed to see the display screen on a computer while performing the inhalation. As can be seen by curve 618, the subject performed entirely within acceptable values in region 606.

The graphs illustrated in FIGS. 6-9 and 19 can be incorporated into a computer program and captured as a screenshot therefrom. Other features of the devices and systems described herein can be controlled using a computer or microprocessor and visualized through an onscreen display.

In some example embodiments disclosed herein, one or more key parameters can define an acceptable inhalation maneuver, including, total inhalation time, peak inspiratory pressure, time to peak inspiratory pressure and average pressure from peak to about 75% of the total inhalation time. In certain embodiments, the total inhalation time can be greater than 5 seconds, the peak inspiratory pressure can be greater than about 6 kPa, time to peak inspiratory pressure can be less than about 1.1 seconds and the average pressure from peak inhalation to 75% of total inhalation time is about 4 kPa. These values are representative of values for training device 100, and can be modified for alternate inhaler training devices, depending on the performance parameters required for optimal delivery of the medicament of the inhaler, including resistance.

Figure 9A:
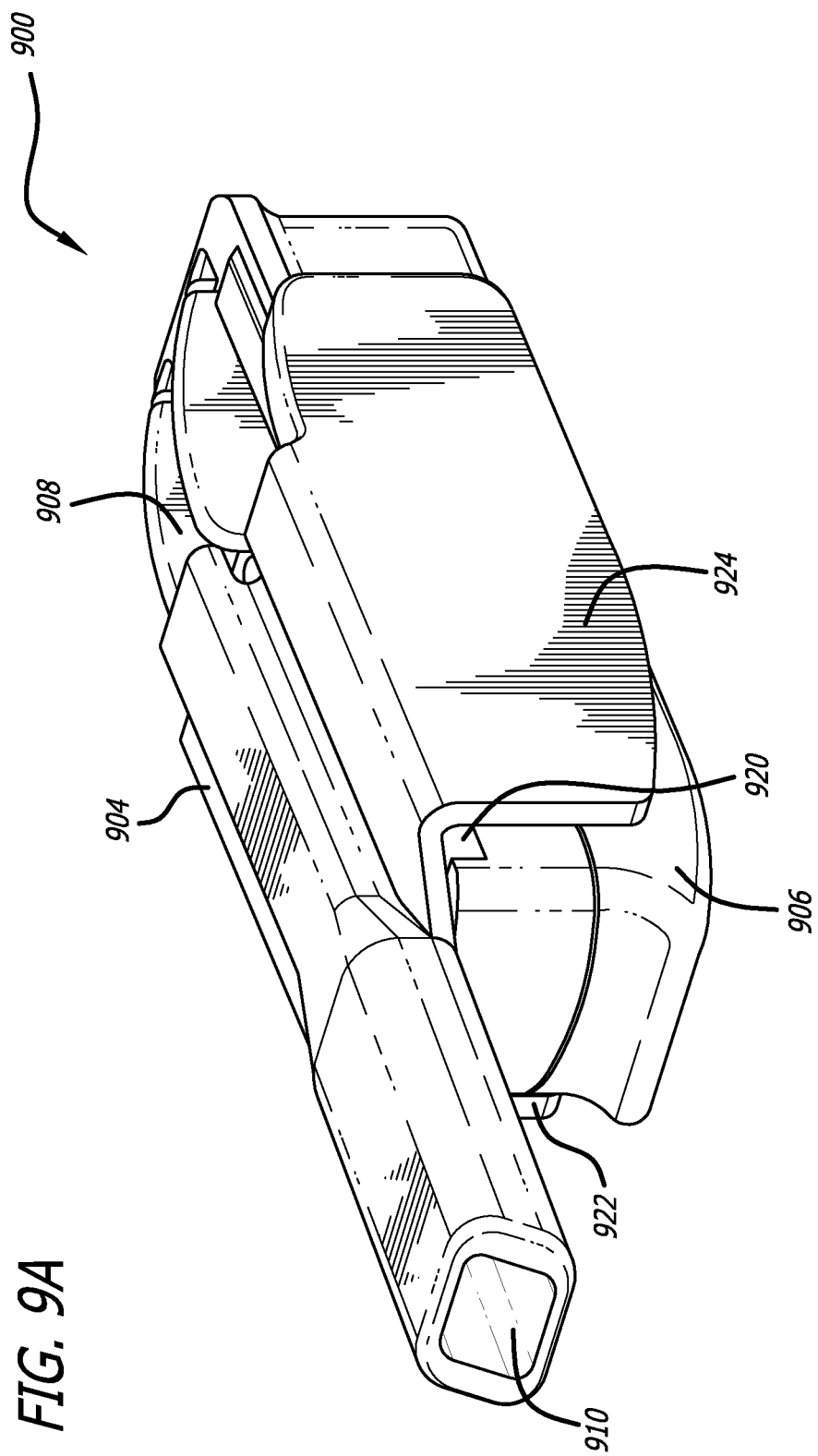
FIGS. 9A and 9B illustrate isometric views of an alternate embodiment of an inhaler with (9B) and without (9A) an integrated sensing and monitoring device.
Figure 9B:
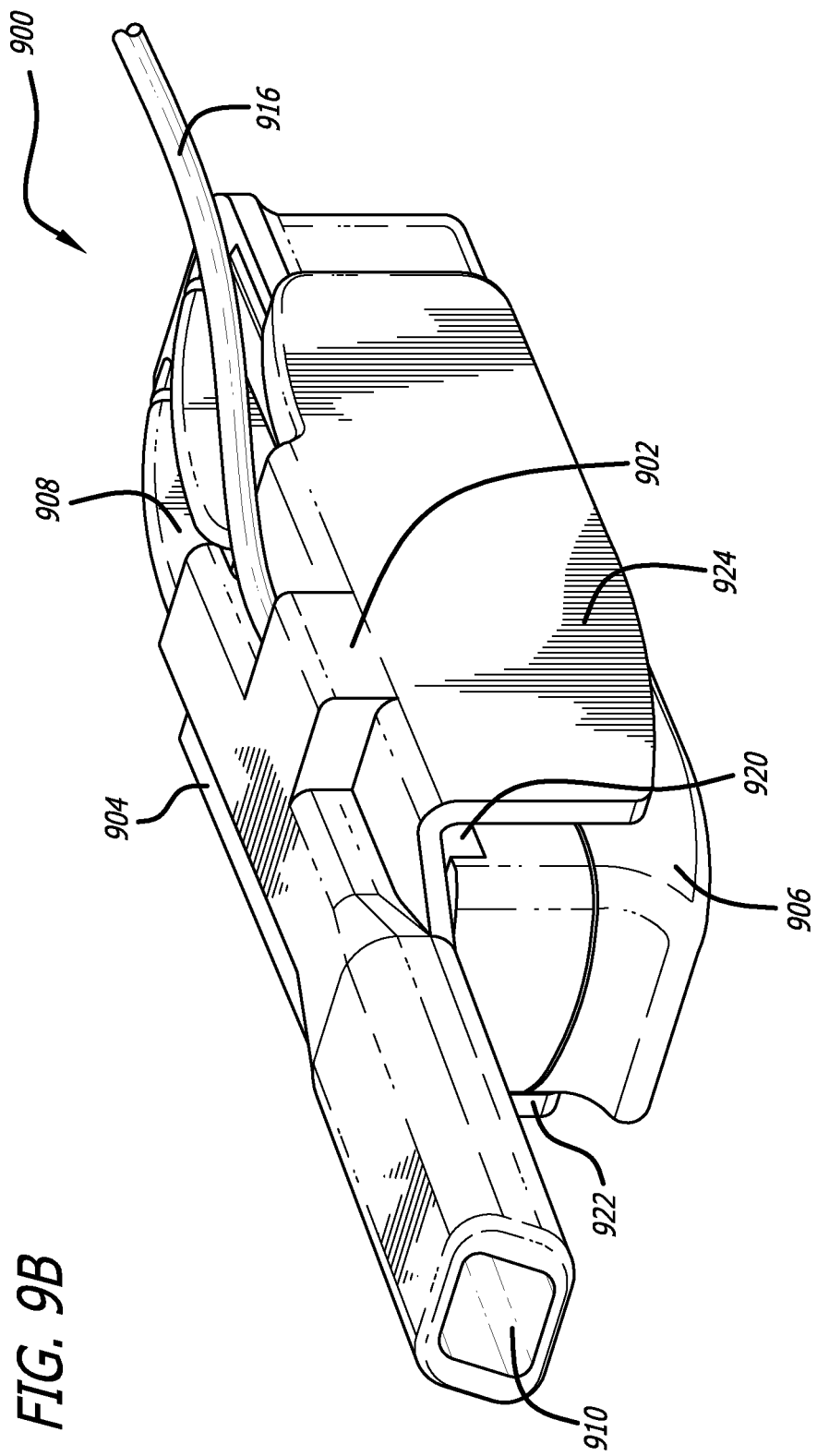
Figure 10:
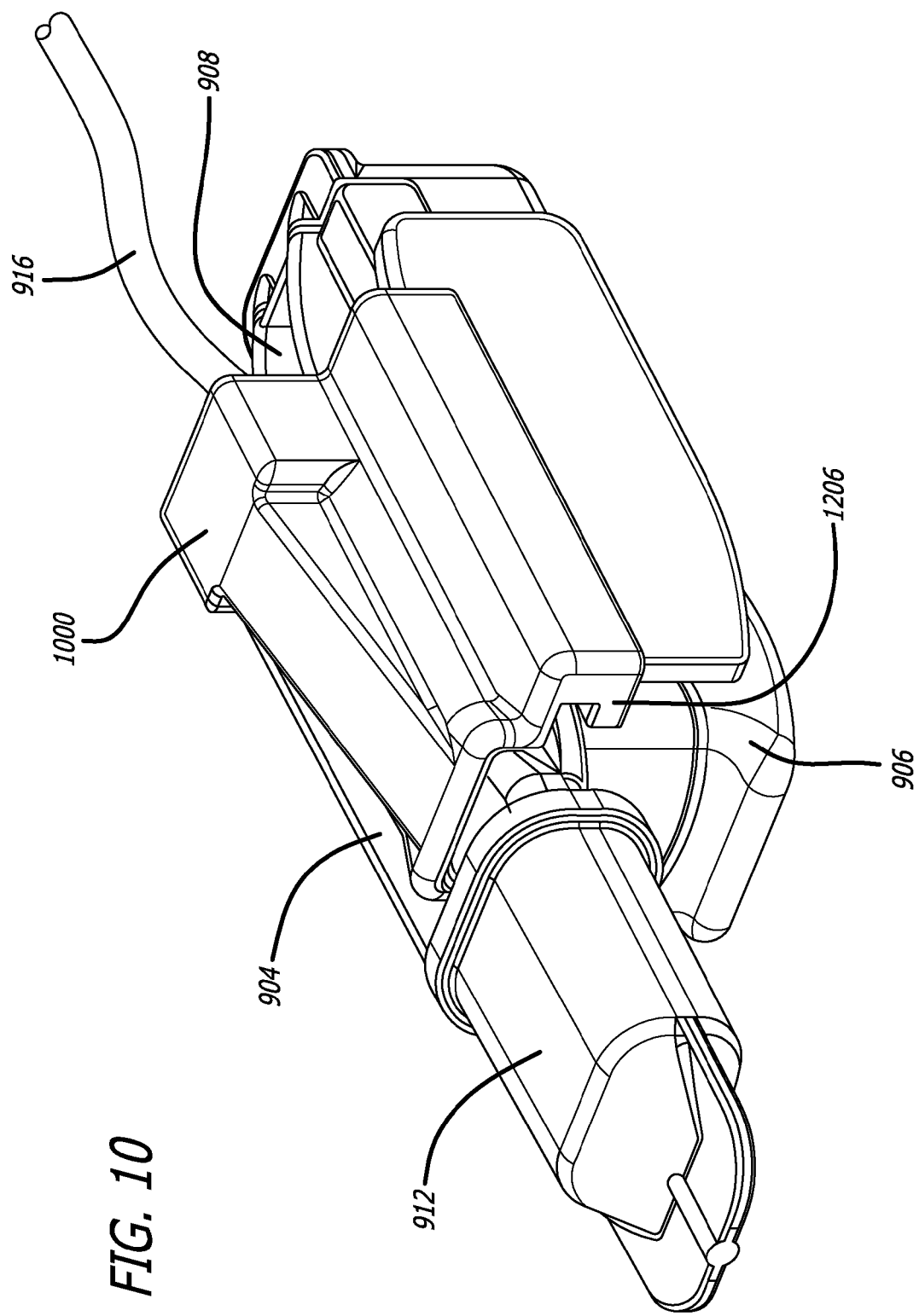
FIG. 10 illustrates an isometric view of yet an alternate embodiment of a sensing and/or monitoring device provided as part of a jacket adapted to a dry powder inhaler.

In another example embodiment illustrated in FIGS. 9A and B, dry powder inhaler 900 can be provided with a sensing and/or monitoring device 902 which can monitor and/or sense signals generated by or within dry powder inhaler 900 during an inhalation maneuver by a patient. FIG. 9A illustrates dry powder inhaler 900 without a sensor device either integrated into the device or attached thereto. Alternatively, in an example embodiment depicted in FIG. 9B, monitoring device 902 can be provided as an integral part of dry powder inhaler 900 on mouthpiece 904 or housing 906 as desired. Dry powder inhaler 900, as depicted in FIG. 9B, has monitoring device 902 adapted within the inhaler, which comprises mouthpiece 904 and housing 906. In one embodiment, the sensor can be integrated within the component walls of inhaler 900, including the mouthpiece, housing, sled or to project into one of the flow pathways of the inhaler. Dry powder inhaler 900 comprises an air conduit with an air inlet 908, air outlet 910 and optional mouthpiece cover 912 (FIG. 10). Monitoring device 902 including a small or miniature microphone is provided within dry powder inhaler 900 configured with mouthpiece 904 and is provided with leads 914 (FIG. 13), which can be connected to an analog to digital converter, a display device, and/or a computer.

Figure 11:
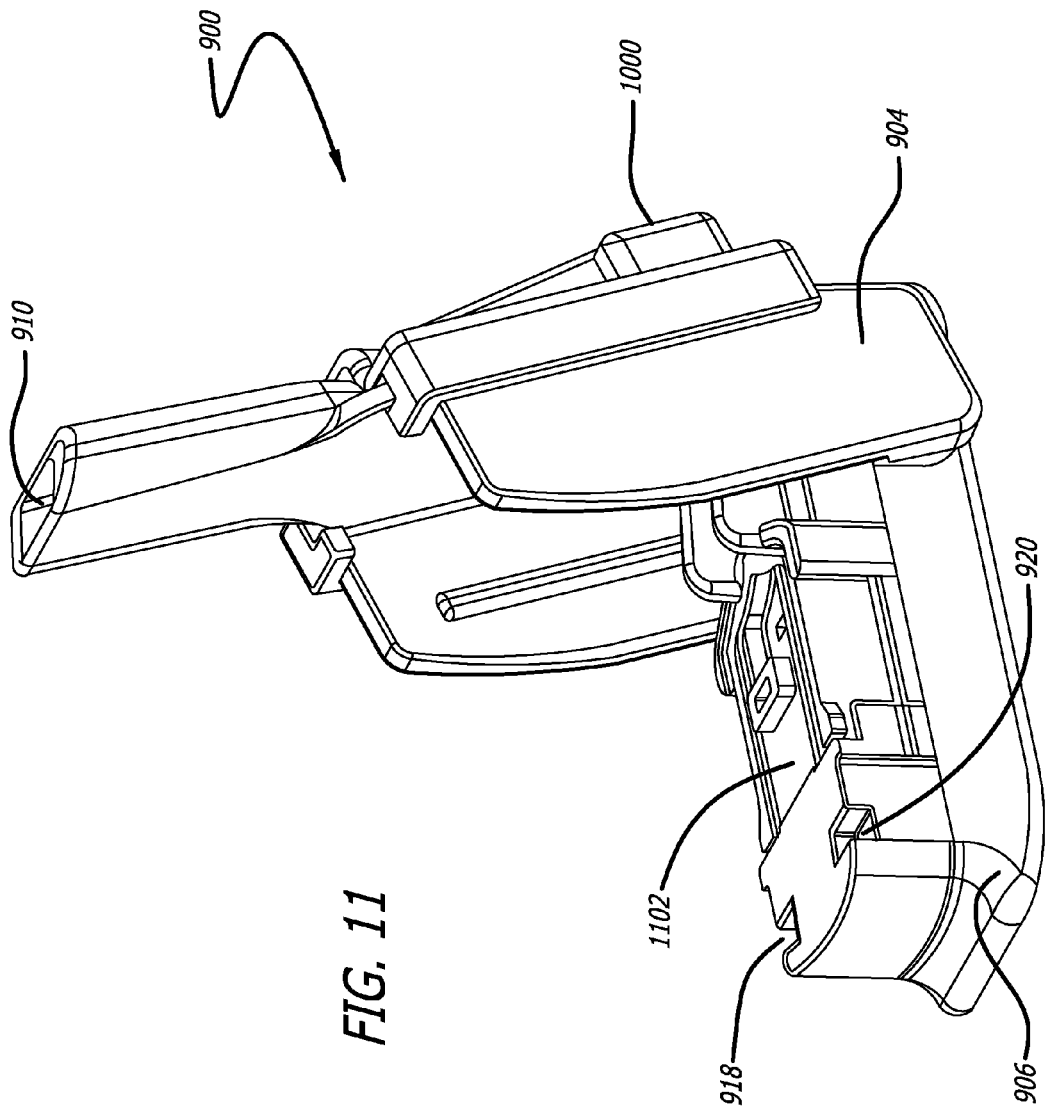
FIG. 11 illustrates an isometric view of the sensing and/or monitoring device illustrated in FIG. 10, wherein a dry powder inhaler system is depicted in an open configuration.
Figure 12:
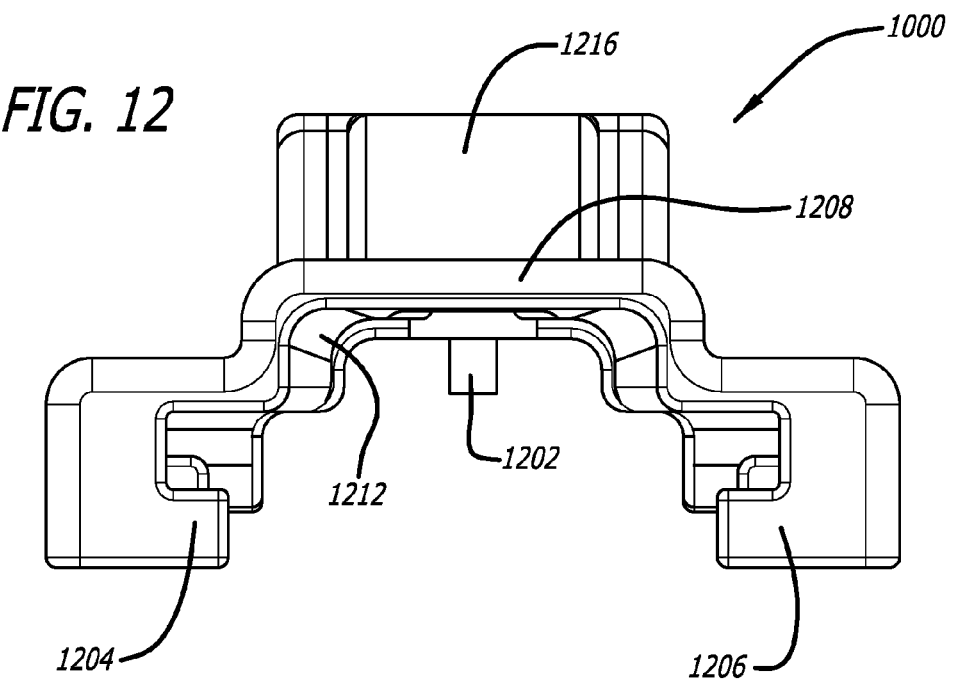
FIG. 12 illustrates a back view of the sensing and/or monitor device shown mounted onto a dry powder inhaler as shown in FIGS. 10 and 11.

FIGS. 10-16 depict alternate embodiments, wherein dry powder inhaler 900 includes detachable sensing and monitoring device 1000 presented as a jacket or cap, wherein detachable sensing and monitoring device 1000 can be provided as a detachable part that can adapt to a dry powder inhaler. In this embodiment, the jacket is manufactured as a separate, detachable device comprising sensors, for example, a microphone which can detect signals and being capable of storing, transmitting or displaying the signals. In one embodiment, the sensor is placed in the bottom portion of the jacket as depicted in FIG. 12 so that the sensor is placed in an air conduit of the inhaler. In other example embodiments, a wireless device can also be provided in connection with the sensor. Sound waves emanating from the inhaler in use with or without a dry powder are detected by the microphone and the signals can be analyzed and correlated to time of powder discharge in the presence of a dry powder, airflow rate, end of powder discharge during an inhalation maneuver, temperature within the inhaler pathway, and the like, depending on the type of sensor used. For example, an increase in sound can be correlated to an increase in flow rate through the device, and/or powder particles collisions in the air stream during delivery.

A sensor such as a microphone, as a result of its small size, can be placed anywhere in the inhaler. In embodiments wherein the sensor is a pressure transducer, the sensor can be placed within an air conduit passing through one of the inhaler compartments. The sensors can be provided, for example, in an air conduit on or within the inhaler or provided as a separate, detachable part as an accessory to the inhaler with a shape or configuration that can be adapted to the inhaler to which is to be adapted, and can include a cap, a jacket, sleeve or a saddle-like configuration that can be adapted or mounted to the inhaler. For the detachable embodiments, the sensing and monitoring apparatus is easy and inexpensive to manufacture and can be made from plastics, and works well with high resistance dry powder inhalers. In the embodiment illustrated in FIG. 10, for example, sensor 1202, depicted in FIG. 12, is provided within the air conduit of mouthpiece 904. The sensor can be any sensor, for example, a thermocouple wire, a pressure transducer, an analog sensor, a microphone, an optical sensor, a gas sensor, or any sensor that can detect signals generated within an inhaler. Sensor 1202, for example is a microphone. The sensors described herein can be adapted to communicate or transmit signals with a wireless device or the signals can be transmitted or stored using wire connection 916 to an analog to digital converter.

Alternatively, an analog to digital converter is provided within the inhaler device and resulting digital data is transferred out of the device directly. The signals provided by the sensors described herein can be in the form of sound generated in an inhaler by airflow passing through the air conduits and/or powder particles collisions entrained in the air flow pathway. Signals generated from the inhaler can be detected by the sensors and stored, transmitted or displayed. Data can be generated from the signals and qualitatively and/or quantitatively analyzed. In this manner, measurements can be made including time of dose release, FIG. 11 depicts an isometric view of the sensing and/or monitoring device illustrated in FIG. 10, wherein dry powder inhaler 900 is depicted in an open configuration. Dry powder inhaler 900 comprises mouthpiece 904, housing 906, and a hinge mechanism, including a gear, for opening and closing dry powder inhaler 900. Movement of mouthpiece 904 to an open configuration as shown in FIG. 11 permits mounting of cartridge 1102 for dosing. Movement of mouthpiece 904 onto housing 906 into a closed or dosing position, as illustrated in FIG. 9, of dry powder inhaler 900 which comprises a slide tray attached to the hinge mechanism, reconfigures cartridge 1102 to a dosing position forming an air pathway through cartridge 1102 and mouthpiece 904.

In one example embodiment, detachable sensing and monitoring device 1000 (FIGS. 12, 13, and 16) can be used as needed by a patient or a health provider in training or gathering information from the patient's inhalation maneuvers and then removed from dry powder inhaler 900, at which point dry powder inhaler 900 remains functional. FIG. 11 depicts an example embodiment wherein detachable sensing and monitoring device 1000 is adapted to mouthpiece 904 so that it fits securely and cannot move during loading or unloading cartridge 1102 with repeated use. Detachable sensing and monitoring device 1000 can be removed after use and remounted onto another inhaler as needed. In this embodiment, the detachable system provides a simple device that does not interfere with, or affect with the characteristic resistance values of the inhalation system.

FIG. 12 illustrates a back view of detachable sensing and monitoring device 1000 shown mounted onto dry powder inhaler 900 in FIGS. 10 and 11, removed from an inhaler. As illustrated in FIG. 12, detachable sensing and monitoring device 1000 is configured to have first flange 1204 and second flange 1206 both of which can engage mouthpiece 904 so that a secure fit can be obtained and can clear housing 906 by sitting within corresponding first groove 918 and second groove 920 on dry powder inhaler 900 when in a closed position. In such an example embodiment, dry powder inhaler 900 can comprise wire connection 916 or at least one lead which can couple to an analog to digital converter so that signals detected by sensor 1202 on traversing portion 1208 of detachable sensing and monitoring device 1000 can be transformed into data. In an alternate example embodiment, detachable sensing and monitoring device 1000 can be adapted to a wireless transmitter to send measured signals to a receiver.

Figure 13:
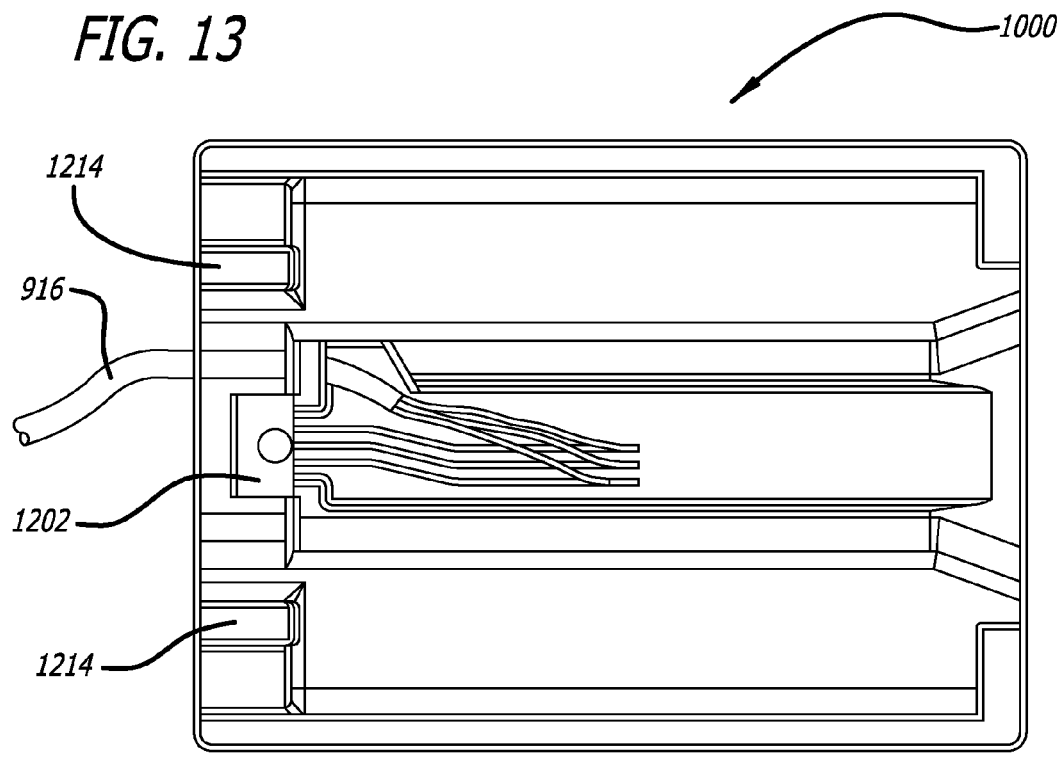
FIG. 13 illustrates a bottom view of the sensing and/or monitor device illustrated in FIG. 12.
Figure 16:
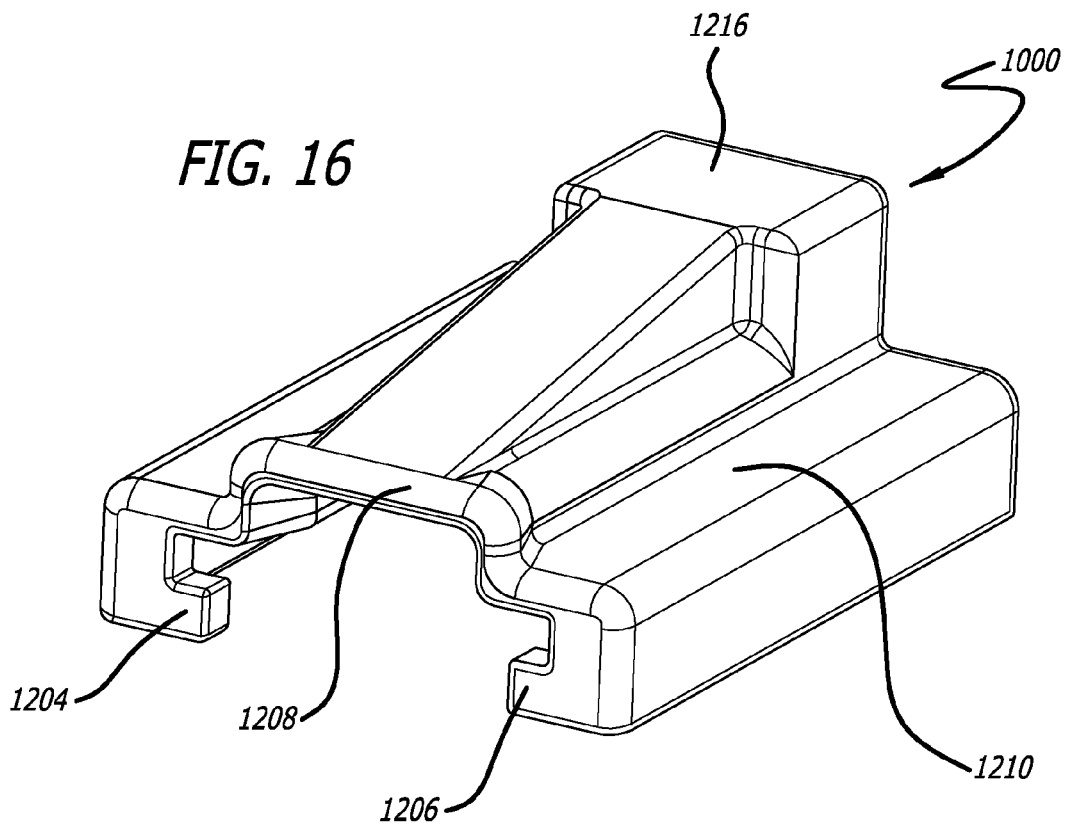
FIG. 16 illustrates an isometric view of the embodiment of the sensing and/or monitoring device depicted in FIGS. 10-15.

FIGS. 12 and 16 illustrate detachable sensing and monitoring device 1000 configured in the shape of a saddle to correspond to different dry powder inhaler configurations. Detachable sensing and monitoring device 1000 has top surface 1210, bottom surface 1212 and sensor 1202 configured on bottom surface 1212 of detachable sensing and monitoring device 1000 in a mid-longitudinal axis. Detachable sensing and monitoring device 1000 can also comprise at least one detent or at least one protrusion 1214 in addition to first flange 1204 and second flange 1206 to engage and adapt to dry powder inhaler 900. In one example embodiment, detachable sensing and monitoring device 1000 comprises a raised area 1216 with a hollow undersurface configured to hold sensor wires 1302 so as to avoid any obstruction of airflow in the air conduit of dry powder inhaler 900. FIG. 13 depicts a bottom view of detachable sensing and monitoring device 1000 illustrating sensor 1202 coupled to sensor wires 1302 and wire connection 916 for connecting to a digital to analogue converter.

Figure 14:
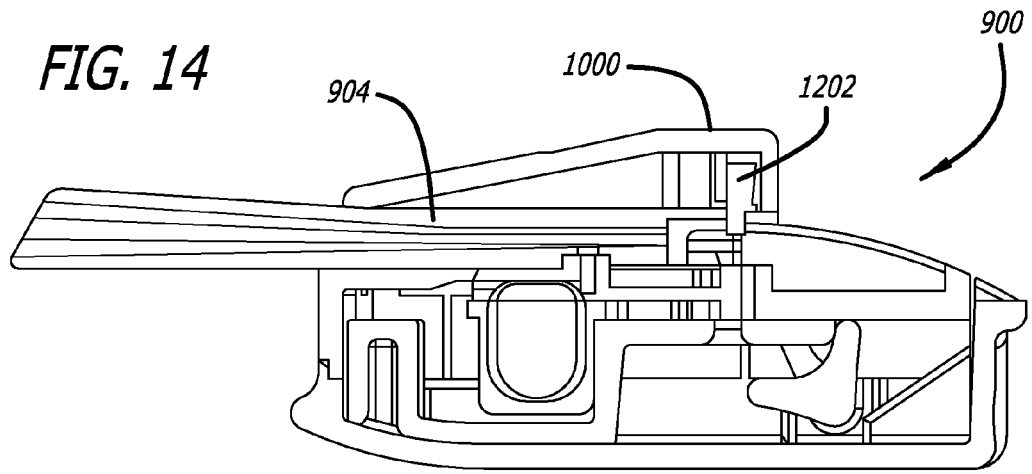
FIG. 14 illustrates a side view of a dry powder inhaler in cross-section through its mid-longitudinal line with a cartridge in place and equipped with a sensing and/or monitoring device.
Figure 15:
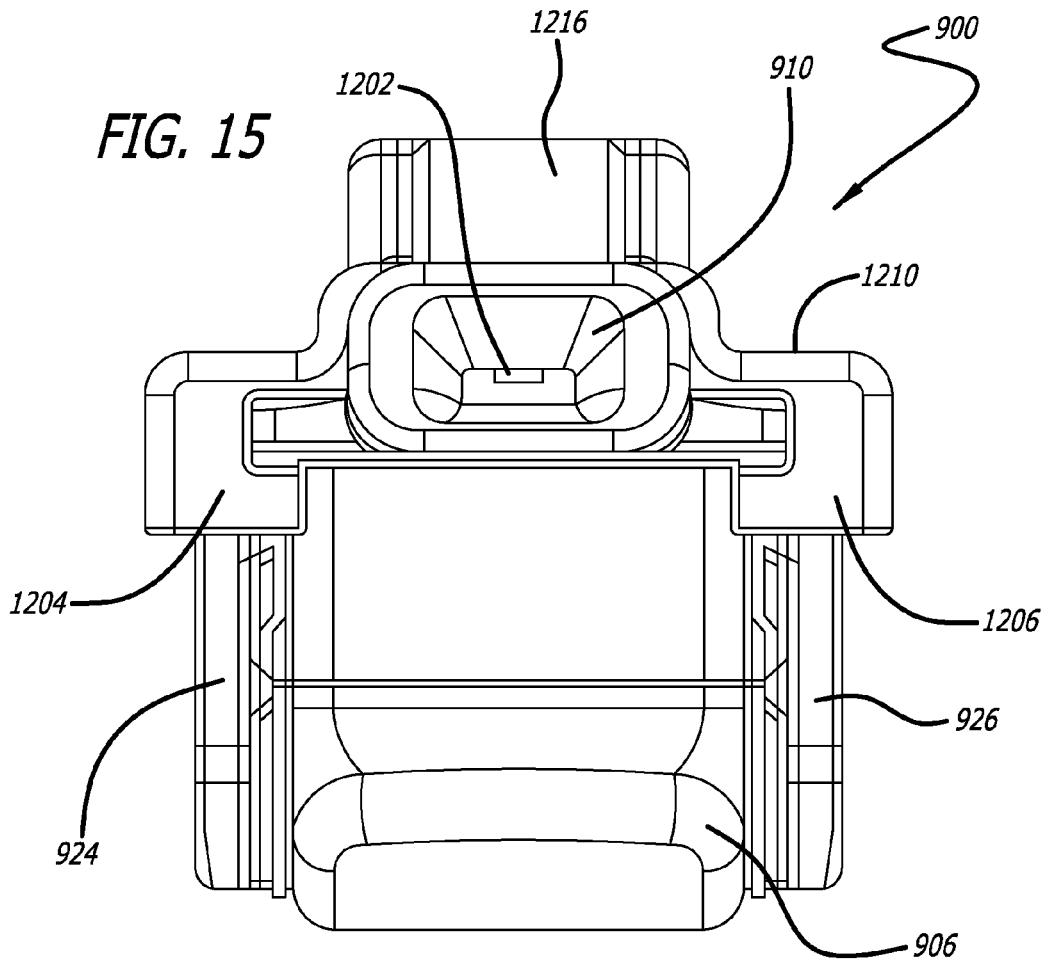
FIG. 15 illustrates a proximal view of a dry powder inhaler equipped with a sensing and/or monitoring device.

FIG. 14 illustrates a cross-sectional side view of dry powder inhaler 900 equipped with detachable sensing and monitoring device 1000 shown in FIG. 11. The cross-section is through its mid-longitudinal line with cartridge 1102 in place and showing the position of sensor 1202 within the jacket. FIGS. 14 and 15 also show the position of sensor 1202, for example a microphone, in the air pathway of mouthpiece 904. In some embodiments, the sensor within the jacket for adapting to an inhaler's air pathways can be configured in different places depending on the inhaler. In this manner, the jacket can be configured to have the sensor integrated so when adapted to the inhaler it is position upstream, downstream or in the middle of the inhaler's air conduit so that the sound signals or vibrations can be detected through the wall of the inhaler or directly on the air pathway.

Figure 17:
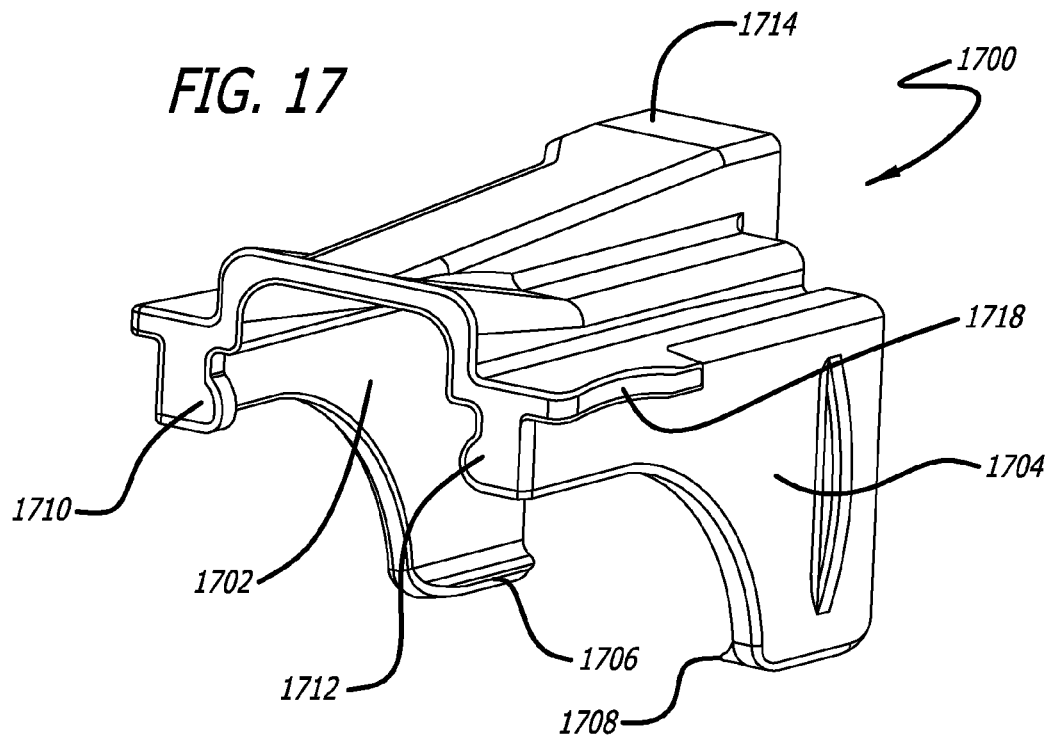
FIG. 17 illustrates an isometric view of an alternate embodiment of a sensing and/or monitoring device for adapting to a dry powder inhaler.

FIG. 17 depicts an isometric view of alternate detachable monitoring device 1700 configured to be adapted to a dry powder inhaler such as dry powder inhaler 900. In this example embodiment, first side panel 1702 and second side panel 1704 can adapt to first inhaler side panel 922 and second inhaler side panel 924 of mouthpiece 904 to form a tight fit with dry powder inhaler 900. Alternate detachable monitoring device 1700 further comprises first bottom flange 1706, second bottom flange 1708, first front flange 1710 and second front flange 1712 used to engage with dry powder inhaler 900. First bottom flange 1706 and second bottom flange 1708 grasp the bottoms of first inhaler side panel 922 and second inhaler side panel 924 while first front flange 1710 and second front flange 1712 grasp the sides of mouthpiece 904 and fit within first groove 918 and second groove 920 on dry powder inhaler 900. Alternate detachable monitoring device 1700 further includes raised area 1714 for housing a sensor and accompanying wires (not illustrated) in its undersurface. Grasping area 1718 facilitates handling of the jacket.

Figure 18:
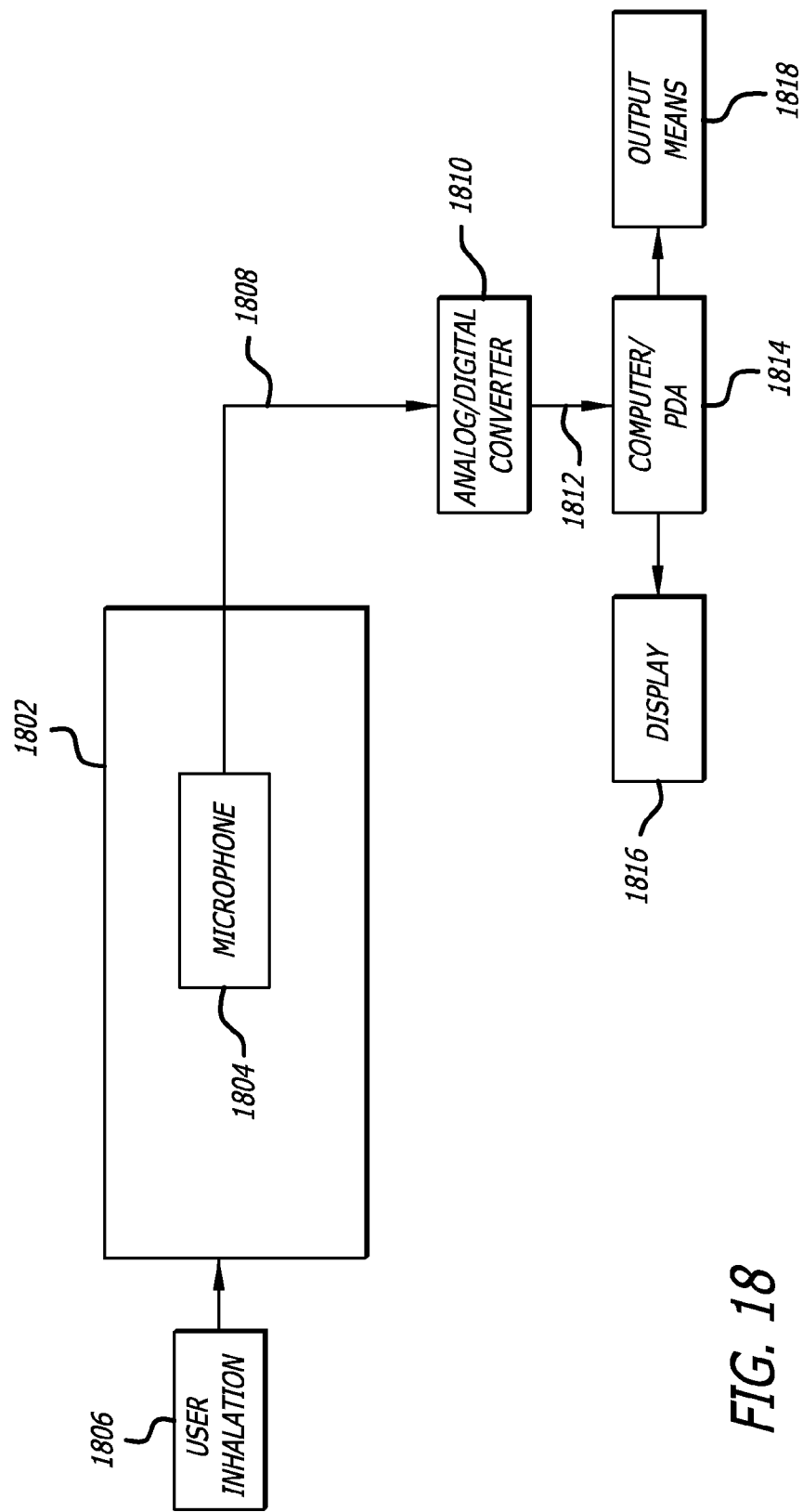
FIG. 18 illustrates a block diagram of the overall exemplary sensing and/or monitoring system disclosed herein.

FIG. 18 illustrates block diagram 1800 for an exemplary configuration of an overall sensing and/or monitoring device and system as disclosed herein. In such an example embodiment, inhaler 1802 comprises microphone 1804 to detect user inhalation 1806 and provide analog signal 1808. During user inhalation 1806, sound waves generated by the airflow as it enters the air conduits of inhaler 1802 are detected by microphone 1804. Microphone 1804 can detect sound signals generated from alteration in pressure, stress, particle displacement and particle velocity of an inhaler in use, the range from 15 to 20,000 Hertz. Microphone 1804 uses the signal pattern resulting from the changing or variations in frequency emissions intrinsically being generated from the inhaler in use with and without powder to determine the flow rate or pressure within the device that when analyzed can be correlated to user and/or device performance. These vibratory signals in microphone 1804 are then converted into analog signal 1808 (e.g. voltage) and transmitted to analog to digital converter 1810. Signals from the analog/digital converter 1812 are communicated to computer/PDA 1814 provided with a microprocessor which uses an algorithm for analyzing the signals received from the analog/digital converter 1812. The processed data is presented with frequency, time and amplitude parameters, and provided on display 1816 or provided to an output means 1818 for storage for future use, communication to a web based digital storage, and/or printing out. In such an example embodiment, by monitoring the signal frequency versus time, the amplitude of analog signal 1808 can be determined. Each dry powder inhaler type can have a typical acoustical pattern, or fingerprint, which develops for the inhaler in use, and the pattern can then be detected and converted to specific signals, analyzed and stored or displayed in a display device such as a computer monitor.

In one example embodiment, a sensing and monitoring system for an inhaler includes a sensing and/or monitoring device structurally configured to be adapted to an inhaler; an analog to digital converter; and a data storage medium. The data storage medium includes a disc drive, a CD-ROM, a server, a flash card or drive, memory card, and the like and includes a set of machine-readable instructions that are executable by a microprocessor or other processing device to implement an algorithm. The algorithm, when run, initiates the steps of generating a logical sub-system generation number derived from detected signals; saving the logical sub-system generation number to a data track within a logical sub-system, wherein the logical sub-system generation number and a cluster generation number in the processing device are compared; and storing and/or displaying information from the algorithm as the results from an inhalation maneuver.

Figure 19:
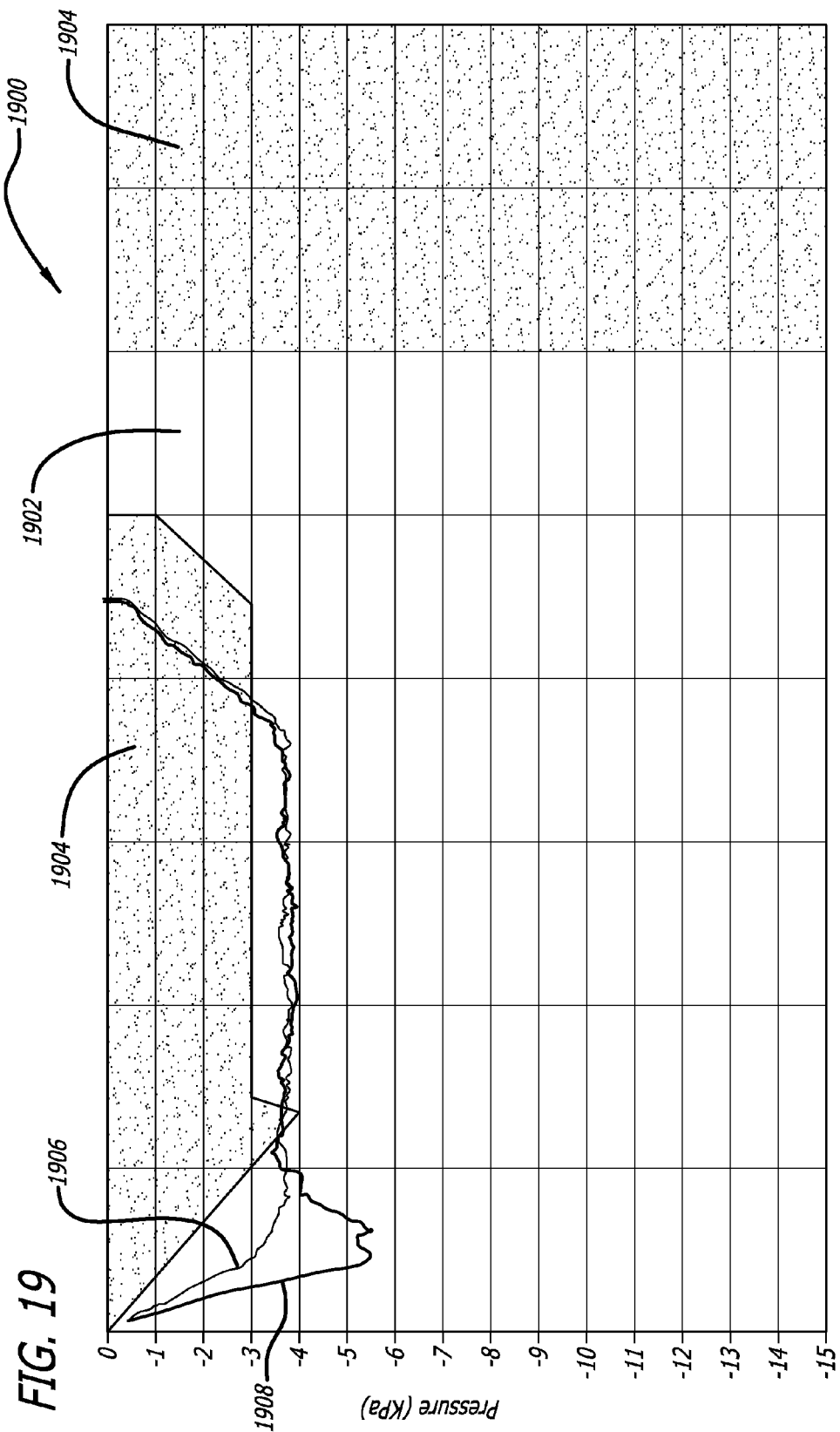
FIG. 19 graphically illustrates an inhalation maneuver performed by a subject trained to take a deep breath and illustrating profiles with and without a dry powder dose tested at the same pressure differential.

FIG. 19 illustrates an exemplary graphic display 1900 of an inhalation maneuver performed using a dry powder inhaler system in response to a pressure differential, wherein the dry powder inhaler system comprised a microphone sensor. Similar to FIGS. 6-9, graphic display 1900 has acceptable region 1902 and unacceptable region 1904. These regions can be colored red and green or any other combination of colors that aid in learning the inhalation maneuver. The subject is coached to take a deep breath with the inhaler for about a period of 4 to 5 seconds and allowed to exhale normally. The graph illustrates inspiratory profiles from the subject showing measurements using a sensing and monitor device described in FIGS. 10-16. FIG. 19 illustrates the data as time in the x-axis and pressure differential in the y-axis.

The inhalations maneuvers were performed using the inhaler with a cartridge without a dry powder formulation, depicted by first curve 1906, and with a dry powder formulation, depicted by second curve 1908. The results show that the sensing and monitoring device can detect the presence of powder emitted from the system, the time of powder emission and the amount of powder emitted from the system. Curve 1906 is the signal produced by the microphone during an inhalation without powder in the system and curve 1908 is the signal produced by the microphone during the same inhalation with powder in the system. The difference of the curves 1908 and 1906 represents the presence and magnitude of powder emitted from the system and time of emission. The data in FIG. 19 illustrate that the sensing and monitoring device is effective for measuring the amount of dose emitted from the inhaler cartridge system.

Example 1

Using an Integrated Training Device

A 57 year old Type II diabetic is instructed to receive inhaled insulin from a dry powder inhalation system, because she has an elevated hemoglobin A1c and is considered out of control. The patient is trained for inhalation using a device as illustrated in FIG. 9B with an integrated sensor. The patient is given the device and asked to take a deep rapid breath in using the training device.

The data is collected on a computer and the patient is able to view the data in real-time on a display screen. The patient's first inhalation attempt is too slow and is indicated on-screen as entering a red "unacceptable region." The patient is instructed to take another rapid breath in that is slightly faster than the previous attempt. Upon completion of the inhalation, the graph illustrates that the patient's inhalation maneuver was acceptable and entirely in the green region of the graph. Upon being comfortable with the training, the patient is clear for use of a similar device.

The patient is prescribed a dry powder inhaler similar to the type that illustrated in FIG. 9A and cartridges filled with an inhalable insulin for treatment of the patient's diabetes. Six months after prescribing the inhaled insulin, the patient's diabetes is diagnosed as under control.

Example 2

Using an Attachable Training Device

A 59 year old Type II diabetic is instructed to receive inhaled insulin from a dry powder inhalation system. The patient has requested the inhalation system for convenience reasons. The patient is trained for inhalation using a device as illustrated in FIG. 9A. The patient is given the device fitted with an attachable sensor similar to that if FIG. 12 and asked to take a deep rapid breath in using the training device.

The data is collected on a computer and the patient is able to view the data in real-time on a display screen. The patient's first attempt is acceptable as indicated by the software. Upon being comfortable with the training, the patient is clear for use of the device.

The patient attachable sensor is removed from the dry powder inhaler. The patient is given the dry powder inhaler and cartridges filled with inhalable insulin for treatment of the patient's diabetes. Six months after prescribing the inhaled insulin, the patient's diabetes is diagnosed as under control and the patient comments on the great convenience of the device.

The preceding disclosures are illustrative embodiments. It should be appreciated by those of skill in the art that the techniques disclosed herein elucidate representative techniques that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A dry powder inhalation detection system comprising:
   a dry powder inhaler
   a unit dose cartridge structurally configured for said dry powder inhaler, and
   a removable device comprising a sensor in communication with said dry powder inhaler, wherein said sensor detects at least one type of signal generated from said dry powder inhaler and sends said at least one signal to at least one microprocessor external to the dry powder inhaler for analysis, storage, printing or display, and further wherein said sensor is configured to transmit in real-time said signal by wire or wireless communication mode to said at least one microprocessor, and said sensor detects a sound signal,
   wherein the microprocessor is configured to execute an algorithm to measure and display concurrently the sound signal as an inhalation maneuver occurs.

2. The dry powder inhalation system of claim 1, wherein said sensor is configured within said dry powder inhalation detection system.

3. The dry powder inhalation system of claim 1, wherein the sound signal is an amplitude of the sound signal, a frequency of the sound signal or combinations thereof.

4. The dry powder inhalation system of claim 1, wherein said sensor is a microphone.

5. The dry powder inhalation system of claim 1, wherein said cartridge comprises a dry powder for pulmonary delivery.

6. The dry powder inhalation system of claim 5, wherein the dry powder comprises diketopiperazine microparticles.

7. The dry powder inhalation system of claim 5, wherein the dry powder comprises at least one active ingredient.

8. The dry powder inhalation system of claim 7, wherein said at least one active ingredient comprises insulin, GLP-1, or analogues thereof.

9. The dry powder inhalation system of claim 1, wherein said dry powder inhaler has a resistance value between about 0.065 ($\sqrt{kPa}$)/liter per minute and about 0.200 ($\sqrt{kPa}$)/liter per minute.

10. The dry powder inhalation system of claim 1, wherein an analog to digital converter communicates said at least one sound signal to a microprocessor configured to analyze and process said at least one sound signal.

11. The dry powder inhalation system of claim 1, wherein display device is a computer monitor.

12. A monitoring system for a dry powder inhaler comprising:
    a detachable monitoring device attached to said dry powder inhaler having a unit dose cartridge and comprising a sound sensor configured to transmit in real-time data by wire or wireless communication mode to an external microprocessor including an analog to digital converter and a data storage medium, said data storage medium including a set of machine-readable instructions that are executable by a processing device to implement an algorithm, said algorithm comprising instructions for manipulating said data including the steps of:
    receiving said data from said sound sensor, filtering said data; transforming said data; analyzing said data;
    providing a graphical display in real-time of an inhalation maneuver through the dry powder inhaler; and
    monitoring a patient in real time using said data.

13. The monitoring system of claim 12, wherein said at least one sensor is a microphone.

14. The monitoring system of claim 12, wherein said detachable monitoring device is mountable on an inhaler.

15. The monitoring system of claim 12, wherein said monitoring device provides a graphical display which is a real-time graphical representation of an inhalation.

16. A method for measuring pressure differential during an inhalation maneuver, comprising:
    providing a dry powder inhaler to a subject wherein said dry powder inhaler comprises a unit dose cartridge and a removable device comprising a sensor configured to detect at least one amplitude of sound signal, at least one frequency of sound signal or combinations thereof generated from said dry powder inhaler, and further wherein said sensor is configured to transmit in real-time said signals by wire or wireless communication mode,
    having said subject inhale for at least one second;
    analyzing said at least one amplitude of sound signal, said at least one frequency of sound signal, or combinations thereof in real time using an algorithm provided with a computer system to generate a data set; and
    displaying in real-time said data set as a graphical representation of time and pressure.

17. An interactive dry powder inhalation system for monitoring an inhalation performed by a user, comprising:
- a dry powder inhaler comprising a cartridge and having a resistance to flow values between 0.065 ($\sqrt{kPa}$)/liter per minute and 0.200 ($\sqrt{kPa}$)/liter per minute;
- a removable device comprising a transducer configured to detect a signal generated from the inhaler in use, and
- an external device including a display device configured to display in real-time a graphical representation of an inhalation maneuver performed by a user, wherein said transducer is configured to transmit in real-time said signal to the external device by wire or wireless communication mode.

18. The interactive dry powder inhalation system of claim 17, wherein the transducer senses and measures a pressure differential within the inhaler.

19. The interactive dry powder inhalation system of claim 17, wherein the transducer is a flow meter configured to sense and measure flow rate through air conduits of the dry powder inhaler.

20. The interactive dry powder inhalation system of claim 17, wherein the transducer is a microphone configured to sense and measure a sound signal generated from within the inhaler.

21. The interactive dry powder inhalation system of claim 17, wherein the inhalation maneuver is displayed on a display device as a graph of pressure versus time.

22. The interactive dry powder inhalation system of claim 17, further comprising a microprocessor which communicates with the transducer by wire connections or wireless.

23. A sensing and monitoring device for adapting to a dry powder inhaler, comprising:
- a detachable device structurally configured to adapt to a dry powder inhaler; said detachable device comprising a microphone for detecting sound generated in said dry powder inhaler and said detachable device is configured to transmit in real-time a signal by wire or wireless communication mode; and wherein the dry powder inhaler has a resistance to flow value between 0.065 ($\sqrt{kPa}$)/liter per minute and 0.200 ($\sqrt{kPa}$)/liter per minute,
- wherein the signal is received by an external device configured to execute an algorithm to measure an inhalation maneuver.

24. The sensing and monitoring device of claim 23, wherein the detachable device communicates signals to an analog to digital converter configured to communicate signals to a microprocessor and/or a display device.

25. A removable sensing and monitoring device for a dry powder inhalation system comprising a dry powder inhaler having a unit dose cartridge and a dry powder formulation, wherein the sensing and monitoring device comprises a microphone configured to detect sound signals generated from the dry powder formulation emitted from the dry powder inhalation system during an inhalation maneuver by a subject, and further wherein said sensing and monitoring device is configured to transmit data signals generated by the sensing and monitoring device in real-time by wire or wireless communication mode to at least one external computing device configured to execute an algorithm to measure and display concurrently the inhalation maneuver.

\* \* \* \* \*